United States Patent
Shaughnessy, Jr. et al.

(10) Patent No.: US 9,714,451 B2
(45) Date of Patent: Jul. 25, 2017

(54) DIAGNOSIS, PROGNOSIS AND IDENTIFICATION OF POTENTIAL THERAPEUTIC TARGETS OF MULTIPLE MYELOMA BASED ON GENE EXPRESSION PROFILING

(71) Applicant: Board of Trustees of the University of Arkansas, Little Rock, AR (US)

(72) Inventors: John D. Shaughnessy, Jr., Roland, AR (US); Bart Barlogie, Little Rock, AR (US); Fenghuang Zhan, Salt Lake City, UT (US)

(73) Assignee: BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 855 days.

(21) Appl. No.: 14/039,728

(22) Filed: Sep. 27, 2013

(65) Prior Publication Data

US 2014/0179545 A1    Jun. 26, 2014

Related U.S. Application Data

(63) Continuation of application No. 13/900,393, filed on May 22, 2013, now Pat. No. 9,574,238, which is a continuation of application No. 12/587,383, filed on Oct. 6, 2009, now Pat. No. 8,954,283, which is a continuation-in-part of application No. 11/110,209, filed on Apr. 20, 2005, now Pat. No. 7,935,679.

(51) Int. Cl.
| | |
|---|---|
| *G01N 33/50* | (2006.01) |
| *C12Q 1/68* | (2006.01) |
| *G06F 19/24* | (2011.01) |
| *G06F 19/18* | (2011.01) |
| *G06F 19/20* | (2011.01) |

(52) U.S. Cl.
CPC ......... *C12Q 1/6883* (2013.01); *C12Q 1/6886* (2013.01); *G06F 19/18* (2013.01); *G06F 19/24* (2013.01); *C12Q 1/6841* (2013.01); *C12Q 2600/106* (2013.01); *C12Q 2600/112* (2013.01); *C12Q 2600/118* (2013.01); *C12Q 2600/136* (2013.01); *C12Q 2600/158* (2013.01); *G06F 19/20* (2013.01)

(58) Field of Classification Search
None
See application file for complete search history.

(56) References Cited

U.S. PATENT DOCUMENTS

| | | |
|---|---|---|
| 7,308,364 B2 | 12/2007 | Shaughnessy et al. |
| 7,371,736 B2 | 5/2008 | Shaughnessy et al. |
| 7,668,659 B2 | 2/2010 | Shaughnessy et al. |
| 7,894,992 B2 | 2/2011 | Shaughnessy et al. |
| 7,935,679 B2 | 5/2011 | Shaughnessy et al. |
| 7,983,850 B2 | 7/2011 | Shaughnessy et al. |
| 8,954,283 B2 | 2/2015 | Shaughnessy et al. |
| 2004/0038860 A1 | 2/2004 | Allen et al. |
| 2008/0234139 A1 | 9/2008 | Shaughnessy et al. |
| 2011/0319470 A1 | 12/2011 | Shaughnessy et al. |
| 2013/0345080 A1 | 12/2013 | Shaughnessy et al. |

FOREIGN PATENT DOCUMENTS

| | | |
|---|---|---|
| WO | WO-03/053215 A2 | 7/2003 |
| WO | WO-2006/028867 A2 | 3/2006 |
| WO | WO-2011/043809 A2 | 4/2011 |

OTHER PUBLICATIONS

Alers, J.C. et al. (2000) "Identification of Genetic Markers for Prostatic Cancer Progression," Lab Invest 80:931-942.
Boyden, L.M. et al. (2002) "High Bone Density Due to a Mutation in LDL-Receptor-Related Protein 5," The New England Journal of Medicine, 346(20):1513-1521.
Claudio, J.O. et al. (2002) "A molecular compendium of genes expressed in multiple myeloma," Blood 100:2175-2186.
Darnell, J. et al. (1986) "Protein Synthesis: The Three Roles of RNA," Molecular Cell Biology 107-108.
De Vos, J. et al. (2001) "Identifying intercellular signaling genes expressed in malignant plasma cells by using complementary DNA arrays," Blood 98:771-780.
Dhodapkar, M.V. et al. (1999) "Syndecan-1 (CD 138) in Myeloma and Lymphoid Malignancies: A Multifunctional Regulator of Cell Behavior Within the Tumor Microenvironment," Leukemia and Lymphoma 34(1-2):35-43.
Dorland's Medical Dictionary (2008) Definition for "ex vivo" from http://www.mercksource.com/pp/us/cns/cns_hl_dorlands_split.jsp?pg=/ppdocs/us/common/dorlands/dorland/three/000038060.htm.
Duggan, D.J. et al. (1999) "Expression profiling using cDNA microarrays," Nature Genetics Supplement 21:10-14.
Eisen, M.B. et al. (1998) "Cluster analysis and display of genome-wide expression patterns," Proc. Natl. Acad. Sci. USA 95:14863-14868.
Gabrea, A. et al. (2006) "Distinguishing primary and secondary translocations in multiple myeloma," DNA Repair 5(9-10):1225-1233.
Gygi, S.P. et al. (1999) "Correlation between Protein and mRNA Abundance in Yeast," Molecular and Cellular Biology 19(3):1720-1730.

(Continued)

Primary Examiner — Jason Sims
(74) Attorney, Agent, or Firm — Foley & Lardner LLP

(57) ABSTRACT

Gene expression profiling is a powerful tool that has varied utility. It enables classification of multiple myeloma into subtypes and identifying genes directly involved in disease pathogensis and clinical manifestation. The present invention used gene expression profiling in large uniformly treated population of patients with myeloma to identify genes associated with poor prognosis. It also demonstrated that over-expression of CKS1B gene, mainly due to gene amplification that was determined by Fluorescent in-situ hybridization to impart a poor prognosis in multiple myeloma. It is further contemplated that therapeutic strategies that directly target CKS1B or related pathways may represent novel, and more specific means of treating high risk myeloma and may prevent its secondary evolution.

4 Claims, 67 Drawing Sheets
(52 of 67 Drawing Sheet(s) Filed in Color)

(56) References Cited

OTHER PUBLICATIONS

Kuehl, W.M. et al. (2005) "Early Genetic Events Provide the Basis for a Clinical Classification of Multiple Myeloma," Hematology 1:346-352.
Little, R.D. et al. (2002) "A Mutation in the LDL Receptor-Related Protein 5 Gene Results in the Autosomal Dominant High-Bone-Mass Trait," Am J. Hum. Genet. 70:11-19.
Loguinov, A.V. et al. (2001) "Gene expression following acute morphine administration," Physiol Genomics 6:169-181.
Ng, R.T. et al. (2001) "Hierarchical Cluster Analysis of SAGE Data for Cancer Profiling," BIODKK01: Workshop on Data Mining in Bioinformatics, San Francisco, CA:65-72.
Shaughnessy, J.D. et al. (2002) "Integrating Cytogenetics and Gene Expression Profiling in the Molecular Analysis of Multiple Myeloma," International Journal of Hematology, Supplement II 76:59-64.
Weber-Mangal, S. et al. (2003) "Breast cancer in young women (<35 years): Genomic aberrations detected by comparative genomic hybridization," International Journal of Cancer 107(4):583-592.
Zhang, Y. et al. (2004) "The LRP5 High-Bone-Mass G171V Mutation Disrupts LRP5 Interaction with Mesd," Molecular and Cellular Biology 24(11):4677-4684.
Restriction Requirement in U.S. Appl. No. 10/289,746, mailed Jun. 13, 2005, 21 pages.
Non-Final Office Action in U.S. Appl. No. 10/289,746, mailed Dec. 23, 2005, 16 pages.
Non-Final Office Action in U.S. Appl. No. 10/289,746, mailed Dec. 21, 2006, 13 pages.
Non-Final Office Action in U.S. Appl. No. 10/289,746, mailed Aug. 31, 2007, 10 pages.
Advisory Action in U.S. Appl. No. 10/289,746, mailed Feb. 12, 2008, 4 pages.
Non-Final Office Action in U.S. Appl. No. 10/289,746, mailed May 15, 2008, 13 pages.
Final Office Action in U.S. Appl. No. 10/289,746, mailed Mar. 6, 2009, 11 pages.
Advisory Action in U.S. Appl. No. 10/289,746, mailed Sep. 4, 2009, 3 pages.
Notice of Allowance in U.S. Appl. No. 10/289,746, mailed Oct. 5, 2009, 7 pages.
Restriction Requirement in U.S. Appl. No. 10/409,004, mailed Sep. 26, 2005, 14 pages.
Non-Final Office Action in U.S. Appl. No. 10/409,004, mailed Dec. 29, 2005, 15 pages.
Final Office Action in U.S. Appl. No. 10/409,004, mailed Nov. 2, 2006, 11 pages.
Advisory Action in U.S. Appl. No. 10/409,004, mailed Feb. 20, 2007, 11 pages.
Non-Final Office Action in U.S. Appl. No. 10/409,004, mailed Jul. 31, 2007, 10 pages.
Final Office Action in U.S. Appl. No. 10/409,004, mailed Aug. 19, 2008, 11 pages.
Advisory Action in U.S. Appl. No. 10/409,004, mailed Jan. 16, 2009, 3 pages.
Non-Final Office Action in U.S. Appl. No. 10/409,004, mailed Apr. 15, 2009, 9 pages.
Non-Final Office Action in U.S. Appl. No. 10/409,004, mailed Nov. 24, 2009, 7 pages.
Final Office Action in U.S. Appl. No. 10/409,004, mailed Apr. 27, 2010, 7 pages.
Notice of Allowance in U.S. Appl. No. 10/409,004, mailed Sep. 24, 2010, 10 pages.
Restriction Requirement in U.S. Appl. No. 10/454,263, mailed Dec. 2, 2005, 34 pages.
Non-Final Office Action in U.S. Appl. No. 10/454,263, mailed Jun. 15, 2006, 10 pages.
Final Office Action in U.S. Appl. No. 10/454,263, mailed Feb. 8, 2007, 15 pages.
Notice of Allowance in U.S. Appl. No. 10/454,263, mailed Jul. 25, 2007, 6 pages.
Restriction Requirement in U.S. Appl. No. 10/931,780, mailed Jan. 31, 2006, 7 pages.
Non-Final Office Action in U.S. Appl. No. 10/931,780, mailed Oct. 12, 2006, 9 pages.
Final Office Action in U.S. Appl. No. 10/931,780, mailed Jun. 18, 2007, 10 pages.
Notice of Allowance in U.S. Appl. No. 10/931,780, mailed Dec. 12, 2007, 4 pages.
Restriction Requirement in U.S. Appl. No. 11/110,209, mailed Aug. 1, 2006, 7 pages.
Non-Final Office Action in U.S. Appl. No. 11/110,209, mailed Oct. 11, 2006, 9 pages.
Final Office Action in U.S. Appl. No. 11/110,209, mailed Dec. 13, 2007, 10 pages.
Non-Final Office Action in U.S. Appl. No. 11/110,209, mailed Aug. 19, 2008, 10 pages.
Final Office Action in U.S. Appl. No. 11/110,209, mailed Mar. 17, 2009, 11 pages.
Advisory Action in U.S. Appl. No. 11/110,209, mailed Jul. 30, 2009, 3 pages.
Non-Final Office Action in U.S. Appl. No. 11/110,209, mailed Sep. 15, 2009, 7 pages.
Final Office Action in U.S. Appl. No. 11/110,209, mailed May 26, 2010, 8 pages.
Notice of Allowance in U.S. Appl. No. 11/110,209, mailed Oct. 7, 2010, 9 pages.
Restriction Requirement in U.S. Appl. No. 12/001,110, mailed Sep. 3, 2009, 8 pages.
Non-Final Office Action in U.S. Appl. No. 12/001,110, mailed Jan. 22, 2010, 9 pages.
Restriction Requirement in U.S. Appl. No. 12/012,302, mailed Sep. 29, 2009, 8 pages.
Non-Final Office Action in U.S. Appl. No. 12/012,302, mailed Mar. 4, 2010, 10 pages.
Final Office Action in U.S. Appl. No. 12/012,302, mailed Aug. 3, 2010, 9 pages.
Advisory Action in U.S. Appl. No. 12/012,302, mailed Dec. 15, 2010, 3 pages.
Notice of Allowance in U.S. Appl. No. 12/012,302, mailed Mar. 3, 2011, 9 pages.
Restriction Requirement in U.S. Appl. No. 12/587,383, mailed Nov. 29, 2011, 7 pages.
Non-Final Office Action in U.S. Appl. No. 12/587,383, mailed Apr. 4, 2012, 11 pages.
Final Office Action in U.S. Appl. No. 12/587,383, mailed Nov. 6, 2012, 10 pages.
Advisory Action in U.S. Appl. No. 12/587,383, mailed Apr. 26, 2013, 3 pages.
Notice of Allowance in U.S. Appl. No. 12/587,383, mailed Aug. 27, 2014, 7 pages.
Restriction Requirement in U.S. Appl. No. 13/135,574, mailed Oct. 31, 2012, 5 pages.
Restriction Requirement in U.S. Appl. No. 13/900,393, mailed Oct. 7, 2015, 6 pages.
International Search Report of the International Searching Authority (ISA/US) for International Application No. PCT/US2002/035724, mailed Jun. 16, 2004.
International Preliminary Report on Patentability of the International Searching Authority (ISA/US) for International Application No. PCT/US2002/035724, mailed Feb. 16, 2005.
International Search Report and Written Opinion of the International Searching Authority (ISA/US) for International Application No. PCT/US2005/031038, mailed Aug. 29, 2006.
Written Opinion of the International Searching Authority (ISA/KR) for International Application No. PCT/US2010/002697, mailed Jun. 1, 2011.
Cole, K.A. et al. (1999) "The genetics of cancer—a 3D model," Nature 21:38-41.
Lockhart, D.J. et al. (2000) "Genomics, gene expression and DNA arrays," Nature 405:827-836.
Zhan, F. et al. (2002) "Global gene expression profiling of multiple myeloma, monoclonal gammopathy of undetermined significance, and normal bone marrow plasma cells," Blood 99(5):1745-1757.

(56) References Cited

OTHER PUBLICATIONS

Non-Final Office Action in U.S. Appl. No. 13/900,393, mailed Jan. 13, 2016.
Notice of Allowance in U.S. Appl. No. 13/900,393, mailed Oct. 14, 2016.

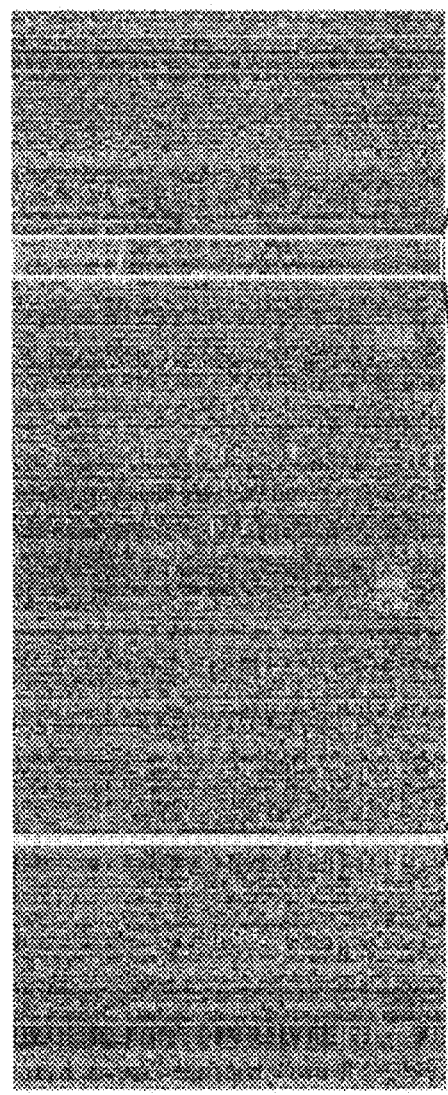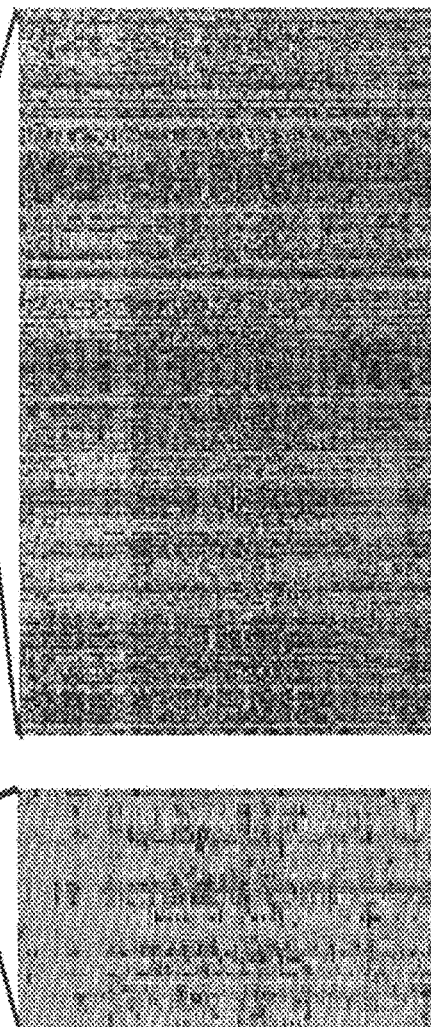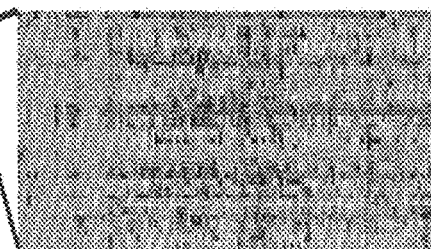
Fig. 1A
Fig. 1B
Fig. 1C
expression greater than mean
expression less than mean
greater magnitude of deviation from mean

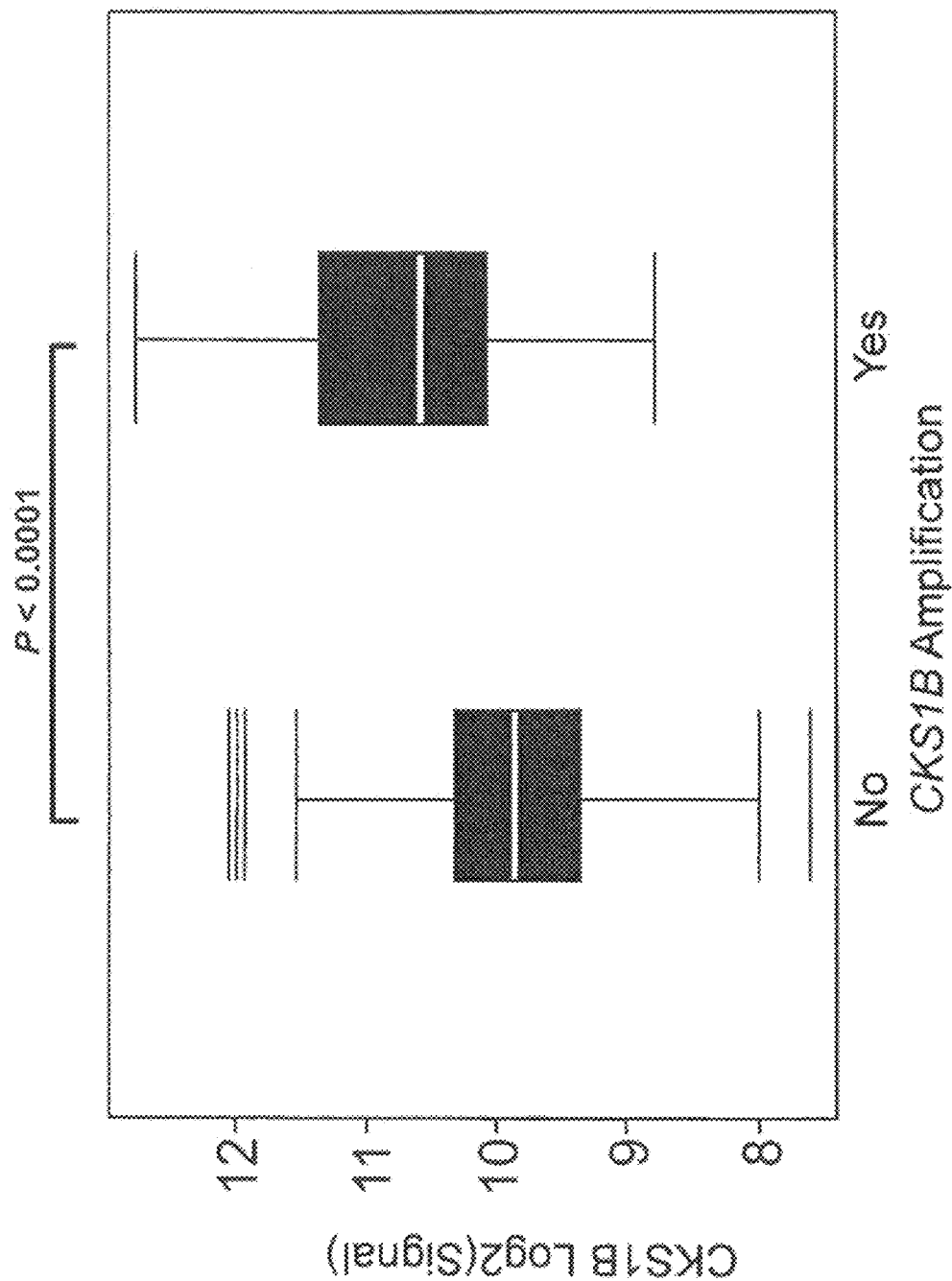

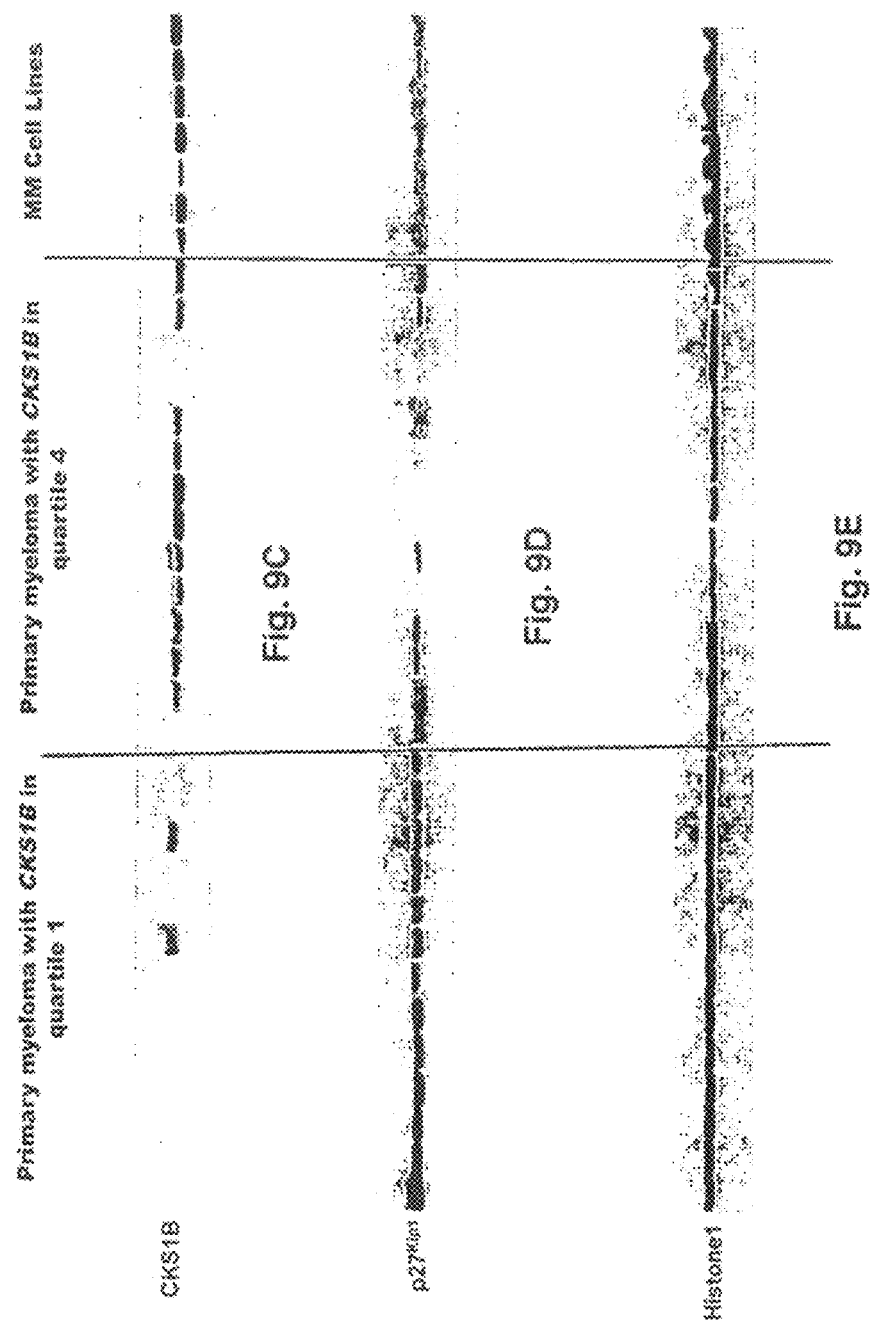

17A

17B

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: primer for IGJH2 gene

<400> SEQUENCE: 1
caatggtcac cgtctcttca                                           20

<210> SEQ ID NO 2
<211> LENGTH: 22
<212> TYPE: DNA

```
<213> ORGANISM: Artificial Sequence
<220> FEATURE:
<223> OTHER INFORMATION: primer for MMSET gene

<400> SEQUENCE: 2
cctcaatttc ctgaaattgg tt                                              22
```

DIAGNOSIS, PROGNOSIS AND IDENTIFICATION OF POTENTIAL THERAPEUTIC TARGETS OF MULTIPLE MYELOMA BASED ON GENE EXPRESSION PROFILING

RELATED APPLICATIONS

This application is a continuation of U.S. application Ser. No. 13/900,393, filed May 22, 2013, which is a continuation of patent application U.S. Ser. No. 12/587,383 filed Oct. 6, 2009, which is a continuation-in-part of patent application U.S. Ser. No. 11/110,209, filed Apr. 20, 2005, now U.S. Pat. No. 7,935,679. The entire teachings of U.S. Ser. Nos. 12/587,383 and 13/900,393 are incorporated herein by reference.

GOVERNMENT SUPPORT

This invention was made with government support under grants CA097513 and CA055819 awarded by the National Institutes of Health. The government has certain rights in the invention.

INCORPORATION BY REFERENCE OF MATERIAL IN ASCII TEXT FILE

This application incorporates by reference the Sequence Listing contained in the following ASCII text file being submitted concurrently herewith:

File name: 46411000016SeqList.txt; created Sep. 27, 2013, 860 bytes in size.

BACKGROUND OF THE INVENTION

Field of the Invention

The present invention relates generally to the field of cancer research. More specifically, the present invention relates to gene expression profiling of a large, uniformly-treated population of patients with myeloma to identify genes associated with poor prognosis.

Description of the Related Art

Multiple myeloma (MM) is a uniformly fatal tumor of terminally differentiated plasma cells (PCs) that home to and expand in the bone marrow. Although initial transformation events leading to the development of multiple myeloma are thought to occur at a post-germinal center stage of development as suggested by the presence of somatic hypermutation of IGV genes, progress in understanding the biology and genetics of multiple myeloma has been slow.

Multiple myeloma cells are endowed with a multiplicity of anti-apoptotic signaling mechanisms that account for their resistance to current chemotherapy and thus the ultimately fatal outcome for most patients. While aneuploidy by interphase fluorescence in situ hybridization (FISH) and DNA flow cytometry are observed in >90% of cases, cytogenetic abnormalities in this typically hypoproliferative tumor are informative in only about 30% of cases and are typically complex, involving on average 7 different chromosomes. Given this "genetic chaos" it has been difficult to establish correlations between genetic abnormalities and clinical outcomes. Only recently has chromosome 13 deletion been identified as a distinct clinical entity with a grave prognosis. However, even with the most comprehensive analysis of laboratory parameters, such as β2-microglobulin (β2M), C-reactive protein (CRP), plasma cell labeling index (PCLI), metaphase karyotyping, and FISH, the clinical course of patients afflicted with multiple myeloma can only be approximated because no more than 20% of clinical heterogeneity can be accounted for. Thus, there are distinct clinical subgroups of multiple myeloma, and modern molecular tests may provide help in identifying these entities.

Monoclonal gammopathy of undetermined significance (MGUS) and multiple myeloma are the most frequent forms of monoclonal gammopathies. Monoclonal gammopathy of undetermined significance is the most common plasma cell dyscrasia with an incidence of up to 10% of population over age 75. The molecular basis of monoclonal gammopathy of undetermined significance and multiple myeloma are not very well understood and it is not easy to differentiate these two disorders. Diagnosis of multiple myeloma or monoclonal gammopathy of undetermined significance is identical in ⅔ of cases using classification systems that are based on a combination of clinical criteria such as the amount of bone marrow plasmocytosis, the concentration of monoclonal immunoglobulin in urine or serum, and the presence of bone lesions. Especially in early phases of multiple myeloma, differential diagnosis is associated with a certain degree of uncertainty.

Furthermore, in the diagnosis of multiple myeloma, clinician must exclude other disorders in which a plasma cell reaction may occur. These other disorders include rheumatoid arthritis, connective tissue disorders, and metastatic carcinoma where the patient may have osteolytic lesions associated with bone metastases. Therefore, given that multiple myeloma is thought to have an extended latency and clinical features are recognized many years after development of the malignancy, new molecular diagnostic techniques are needed for differential diagnosis of multiple myeloma, e.g., monoclonal gammopathy of undetermined significance versus multiple myeloma, or recognition of various subtypes of multiple myeloma.

Additionally, although this malignancy of B-cell origin initially resides in the bone marrow, it can transform into an aggressive disease with an abnormal karyotype, increased proliferation, elevated LDH and extra-medullary manifestations (Barlogie, B et al., 2001). Specific molecular genetic lesions and tumor cell-stroma interaction influence the clinical course and response to therapy (Kuehl, W. M. et al., 2002; Shaughnessy, J et al., 2003; Hideshima, T et al., 2004; Fonseca, R. et al., 2004). Although complete responses can be obtained in more than 40% of patients with high-dose therapy, survival varies widely from few months to more than 15 years (Attal, M. et al., 2003; Barlogie, B. et al., 2004). High-risk disease is best captured by abnormal metaphase cytogentics, present in one-third of newly diagnosed patients and reflecting high proliferative capacity of the malignant disease (Shaughnessy, J. et al., 2003).

Global gene expression profiling has emerged as a powerful tool for classifying disease subtypes and developing robust prognostic models in leukemia and lyphoma (Shipp, M. A. et al., 2002; Yeoh, E. J. et al., 2002; Rosenwald, A. et al., 2002; Bullinger, L. et al., 2004; Valk, P. J. et al., 2004). In myeloma, this technology helped identify genes directly involved in disease pathogenesis and clinical manifestation (Zhan, F et al., 2002; Zhan, F. et al., 2003; Tarte, K et al., 2003; Tian, E. et al., 2003).

Thus, the prior art is deficient in methods for identifying genes associated with poor prognosis in patients with myeloma. The present invention fulfills this long-standing need and desire in the art.

SUMMARY OF THE INVENTION

Bone marrow plasma cells from 74 patients with newly diagnosed multiple myeloma, 5 patients with monoclonal gammopathy of undetermined significance (MGUS), and 31 normal volunteers (normal plasma cells) were purified by CD138+ selection. Gene expression of purified plasma cells and 7 multiple myeloma cell lines were profiled using high-density oligonucleotide microarrays interrogating ~6,800 genes. Using hierarchical clustering analysis, normal and multiple myeloma plasma cells were differentiated and four distinct subgroups of multiple myeloma (MM1, MM2, MM3 and MM4) were identified. The gene expression patterns of MM1 were similar to that of normal plasma cells and monoclonal gammopathy of undetermined significance, whereas MM4 was similar to multiple myeloma cell lines. Clinical parameters linked to poor prognosis such as abnormal karyotype (p=0.0003) and high serum β2-microglobulin levels (p=0.0004) were most prevalent in MM4. Genes involved in DNA metabolism and cell cycle control were overexpressed in MM4 as compared to MM1.

Using chi square and Wilcoxon rank sum tests, 120 novel candidate disease genes that discriminated between normal and malignant plasma cells (p<0.0001) were identified. Many of these candidate genes are involved in adhesion, apoptosis, cell cycle, drug resistance, growth arrest, oncogenesis, signaling and transcription. In addition, a total of 156 genes, including FGFR3 and CCND1, exhibited highly elevated ("spiked") expression in at least 4 of the 74 multiple myeloma cases (range of spikes: 4 to 25). Elevated expression of FGFR3 and CCND1 were caused by translocation t(4; 14)(p16;q32) or t(11; 14)(q13;q32).

Additionally, multivariate stepwise discriminant analysis was used to identify a minimum subset of genes whose expression was intimately associated with malignant features of multiple myeloma. Fourteen genes were defined as predictors that were able to differentiate plasma cells of multiple myeloma patients from normal plasma cells with a high degree of accuracy, and 24 genes were identified as predictors that are able to differentiate distinct subgroups of multiple myeloma (MM1, MM2, MM3 and MM4) described herein.

Furthermore, it was also demonstrated that multiple myeloma could be placed into a developmental schema parallel to that of normal plasma cell differentiation. Based on gene expression profiling, the MM4, MM3 and MM2 subgroups described above were found to have similarity with tonsil B cells, tonsil plasma cells and bone marrow plasma cells respectively. These data suggested that the enigmatic multiple myeloma is amendable to a gene expression/development stage-based classification system.

Thus, gene expression profiling using DNA microarray and hierarchical clustering analysis could be used to classify subgroups of multiple myeloma, identify genes with differential expression in subsets of multiple myeloma patients, and identify potential therapeutic targets for multiple myeloma. For example, multiple myeloma or subgroups of multiple myeloma can be diagnosed based on the expression of a group of 14 genes or a group of 24 genes respectively. Additionally, multiple myeloma can be diagnosed based on the expression levels of 15 genes that classify patients into 7 subgroups of myeloma.

In another aspect of the present invention, multiple myeloma can be treated using methods that involve inhibiting or enhancing expression of genes that are found to be over-expressed or down-regulated respectively in multiple myeloma patients as disclosed herein. Additionally, multiple myeloma can be classified based on developmental stage by comparing gene expression profiling between multiple myeloma cells and normal B or plasma cells.

In one aspect of the present invention, there is provided a method of identifying genes associated with a phenotype of interest in a population. This method comprises isolating plasma cells from individuals within the population. Subsequently, oligonucleotide microarrays may be used to profile gene expression in the cells. Further, the gene expression profiles in the cells are correlated with the phenotype of interest. Thus, the genes associated with the phenotype of interest in the population are identified. The present invention provides a method of diagnosing an individual with myeloma. This method comprises (a) obtaining a bone marrow sample from the individual and (b) determining an amplification of a gene on chromosome 1q21 or a deletion of chromosome 13 in the sample, thereby diagnosing the individual with myeloma. The present invention further provides a method of identifying an individual having high-risk myeloma. This method comprises (a) obtaining a bone marrow sample from the individual and (b) determining an amplification of a gene on chromosome 1q21, where the amplification of the gene increases the risk of developing myeloma, thereby identifying the individual having high-risk myeloma. The present invention also provides a method of screening drugs useful in treating high-risk myeloma. Such a method comprises contacting a sample comprising CKS1B with a drug and determining the inhibitory effect of the drug on amplification, over-expression or activity of CKS1B gene, thereby screening for drugs useful in treating high-risk myeloma.

An alternative approach to the method of screening drugs useful in treating high-risk myleoma would comprise contacting a sample comprising CKS1B with a drug and determining the inhibitory effect of the drug on amplification, over-expression or activity of CKS1B protein. The present invention still further provides a method of treating an individual having high-risk myeloma. Such a method comprises administering to the individual a compound that inhibits amplification, over-expression or activity of CKS1B gene. An alternative approach to the method of treating an individual having high-risk myeloma would comprise administering to the individual a compound that inhibits amplification, over-expression or activity of CKS1B protein.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A shows cluster-ordered data table. The clustering is presented graphically as a colored image. Along the vertical axis, the analyzed genes are arranged as ordered by the clustering algorithm. The genes with the most similar patterns of expression are placed adjacent to each other. Likewise, along the horizontal axis, experimental samples are arranged; those with the most similar patterns of expression across all genes are placed adjacent to each other. Both sample and gene groupings can be further described by following the solid lines (branches) that connect the individual components with the larger groups. The color of each cell in the tabular image represents the expression level of each gene, with red representing an expression greater than the mean, green representing an expression less than the mean, and the deeper color intensity representing a greater magnitude of deviation from the mean. FIG. 1B shows amplified gene cluster showing genes downregulated in MM. Most of the characterized and sequence-verified cDNA-encoded genes are known to be immunoglobulins. FIG. 1C shows cluster enriched with genes whose expression level was correlated with tumorigenesis, cell cycle, and proliferation rate. Many of these genes were also statistically significantly upregulated in multiple myeloma ($\chi^2$ and WRS test) (see Table 5).

FIG. 6A shows box plots of log base 2-transformed Affymetric signal plotted on the y-axis with respect to 351 cases according to the quartile expression levels (x-axis). FIG. 6B shows Kaplan-Meier plots of overall survival that revealed inferior outcome among the 88 patients with $4^{th}$ quartile expression levels of CKS1B compared to the remaining 263 patients with quartile 1-3 expression levels.

FIG. 7A-D show that increased CKS1B expression is related to CKS1B DNA copy number and degree of DNA amplification is linked to poor survival. FIG. 7A shows metaphase fluorescence in situ hybridization analysis of CKS1B at 1q21 (red signal) and ASPM at 1q31 (green signal) performed on plasma cells from a patient with myeloma. The tandem duplications of CKS1B (arrows) and the greater degree of amplification of 1q21 were compared to 1q31. FIG. 7B shows box plots of log base 2-transformed Affymetrix signal (y-axis) by CKS1B amplification (N=197). In box plots, the top, bottom and middle lines of each box correspond to the $75^{th}$ percentile (top quartile), $25^{th}$ percentile (bottom quartile) and $50^{th}$ percentile (median) respectively and. the whiskers extend to the nearest point not beyond 1.5 times the inter-quartile range, with observations beyond these indicated by individual lines. A Wilcoxon rank sum test was used to compare Signal across copy number categories. FIG. 7C shows Kaplan-Meier plot of overall survival in the validation cohort that depicts inferior outcomes among the 89 patients with CKS1B amplification compared to the remaining 135, as determined by interphase fluorescence in situ hybridization. FIG. 7D shows the Kaplan-Meier plot as shown in 28C for the combined sample of 421 patients.

FIGS. 9A-E show that CKS1B mRNA is correlated with nuclear protein levels and inversely correlated with p27$^{Kip1}$. FIG. 9A shows CKS1B and FIG. 9B shows CDKN1B (p27$^{Kip1}$) gene expression signal in 1000 unit increments plotted on the y-axis. Primary myelomas with CKS1B expression in quartile 1 (n=13) and quartile 4 (n=14) and myeloma cell lines (n=7) were grouped and plotted from left to right along the X-axis. Each bar represents a sample and the height indicates the level of gene expression in the sample. FIGS. 9C-E show Western Blot analysis of nuclear protein extracts for CKS1B (FIG. 9C), phos-thr-187-p27$^{Kip1}$ (FIG. 9D) and Histone 1A (FIG. 9E) (loading control) respectively from aliquots of same plasma cells used in FIG. 9A and FIG. 9B. Samples are ordered from left to right in the exact same order in all panels. There is a high degree of correlation between CKS1B gene expression and protein expression. CDKN1B (p27$^{Kip1}$) gene expression is not correlated with CKS1B gene expression, protein levels or p27$^{Kip1}$ protein levels. However, there is a strong inverse correlation between CKS1B protein levels and p27$^{Kip1}$ protein levels. Uniform histone 1A protein levels indicate equal protein loading across all samples.

FIG. 12A show for all treatment protocols. FIG. 12B show for Total Therapy 3 (TT3). FIG. 12C show for Total Therapy 2 (TT2) without thalidomide. FIG. 12D show for Total Therapy 2 (TT2) with thalidomide.

FIG. 13A show for all treatment protocols. FIG. 13B show for Total Therapy 3 (TT3). FIG. 13C show for Total Therapy 2 (TT2) without thalidomide. FIG. 13D show for Total Therapy 2 (TT2) with thalidomide.

FIG. 14A show for all treatment protocols. FIG. 14B show for Total Therapy 3 (TT3). FIG. 14C show for Total Therapy 2 (TT2) without thalidomide. FIG. 14D show for Total Therapy 2 (TT2) with thalidomide.

FIG. 15A show for all treatment protocols. FIG. 15B show for Total Therapy 3 (TT3). FIG. 15C show for Total Therapy 2 (TT2) without thalidomide. FIG. 15D show for Total Therapy 2 (TT2) with thalidomide.

FIG. 16A show for all treatment protocols. FIG. 16B show for Total Therapy 3 (TT3). FIG. 16C show for Total Therapy 2 (TT2) without thalidomide. FIG. 16D show for Total Therapy 2 (TT2) with thalidomide.

FIG. 17A show for all treatment protocols. FIG. 17B show for Total Therapy 3 (TT3). FIG. 17C show for Total Therapy 2 (TT2) without thalidomide. FIG. 17D show for Total Therapy 2 (TT2) with thalidomide.

FIG. 18A shows for all treatment protocols. FIG. 18B shows for Total Therapy 3 (TT3). FIG. 18C shows for Total Therapy 2 (TT2) without thalidomide. FIG. 18D shows for Total Therapy 2 (TT2) with thalidomide.

FIG. 19A shows for all treatment protocols. FIG. 19B shows for Total Therapy 3 (TT3). FIG. 19C shows for Total Therapy 2 (TT2) without thalidomide. FIG. 19D shows for Total Therapy 2 (TT2) with thalidomide.

FIG. 20A shows for all treatment protocols. FIG. 20B shows for Total Therapy 3 (TT3). FIG. 20C shows for Total Therapy 2 (TT2) without thalidomide. FIG. 20D shows for Total Therapy 2 (TT2) with thalidomide.

FIG. 21A shows for all treatment protocols. FIG. 21B shows for Total Therapy 3 (TT3). FIG. 21C shows for Total Therapy 2 (TT2) without thalidomide. FIG. 21D shows for Total Therapy 2 (TT2) with thalidomide.

FIG. 22A-C show overall survival rates. FIG. 22D-F show event free survival rates.

FIGS. 23A-C show overall survivability rates. FIG. 23D-F show event free survivability rates.

FIG. 24A-C show overall survivability rates. FIGS. 24D-F show event free survivability rates.

FIG. 25A-C show overall survivability rates. FIG. 25D-F show event free survivability rates.

FIG. 26A show the combined overall survivability rates for TT2 and TT3. FIG. 26B show the combined event free survivability rates for TT2 and TT3.

FIG. 27A show the combined overall survivability rates for TT2 and TT3. FIG. 27B show the combined overall survivability rates for TT2 and TT3.

FIG. 28A show the overall survivability rates for TT2 and TT3. FIG. 28B show the overall survivability rates for TT2 and TT3.

FIG. 29A show combined overall survivability rates for TT2 and TT3. FIG. 29B show combined event free survivability rates for TT2 and TT3.

DETAILED DESCRIPTION OF THE INVENTION

Figure 1D:
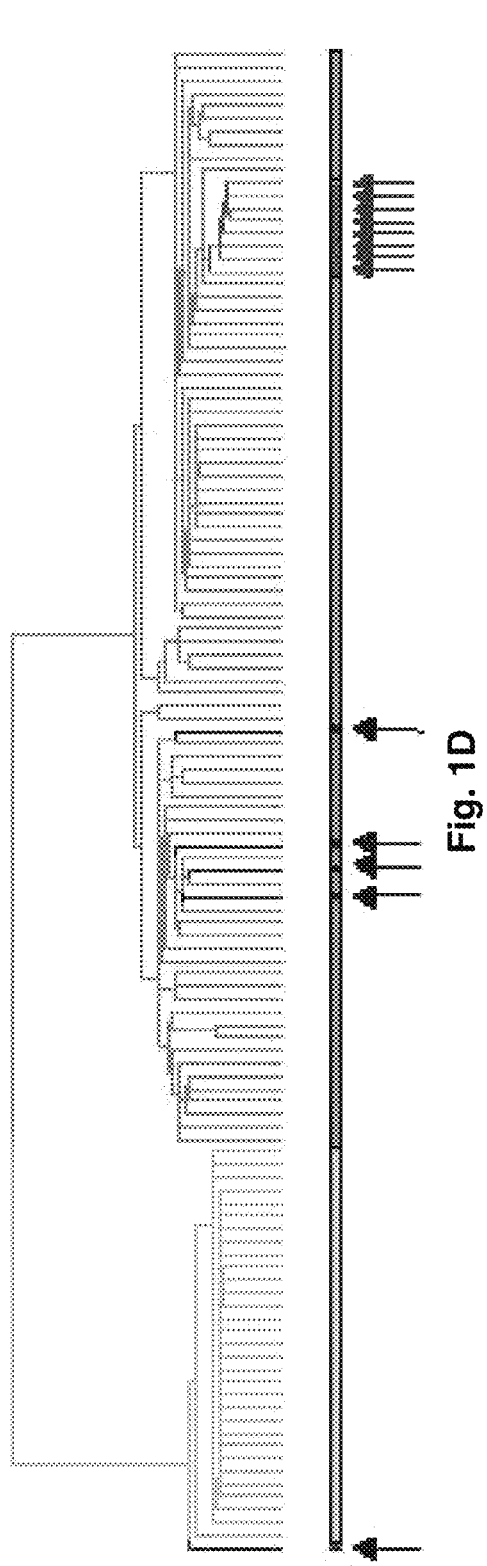
FIG. 1D shows dendrogram of hierarchical cluster. 74 cases of newly diagnosed untreated multiple myeloma, 5 monoclonal gammopathy of undetermined significance, 8 multiple myeloma cell lines, and 31 normal bone marrow plasma cell samples clustered based on the correlation of 5,483 genes (probe sets). Different-colored branches represent normal plasma cell (green), monoclonal gammopathy of undetermined significance (blue arrow), multiple myeloma (tan) and multiple myeloma cell lines (brown arrow).

There is now strong evidence that global gene expression profiling can reveal molecular heterogeneity of similar or related hematopoietic malignancies that have been difficult to distinguish. Genes exhibiting significant differential expression between normal and malignant cells can be used in the development of clinically relevant diagnostics as well as provide clues into the basic mechanisms of cellular transformation. In fact, these profiles might even be used to identify malignant cells even in the absence of any clinical manifestations. In addition, biochemical pathways in which the products of these genes act may be targeted by novel therapeutics.

Both normal and malignant plasma cells were purified to homogeneity from bone marrow aspirates using anti-CD138-based immunomagnetic bead-positive selection.

Using these cells, the present invention provided the first comprehensive global gene expression profiling of newly diagnosed multiple myeloma patients and contrasted these expression patterns with those of normal plasma cells. Novel candidate multiple myeloma disease genes were identified and this profiling led to development of a gene-based classification system for multiple myeloma.

Results from hierarchical cluster analysis on multiple myeloma plasma cells and normal plasma cells, as well as the benign plasma cell dyscrasia monoclonal gammopathy of undetermined significance and end-stage-like multiple myeloma cell lines revealed normal plasma cells are unique and that primary multiple myeloma is either like monoclonal gammopathy of undetermined significance or multiple myeloma cell lines. In addition, multiple myeloma cell line gene expression was homogeneous as evidenced by tight clustering in the hierarchical analysis. Similarity of multiple myeloma cell line expression patterns to primary newly diagnosed forms of multiple myeloma support the validity of using multiple myeloma cell lines as models for multiple myeloma.

Four distinct clinical multiple myeloma subgroups (MM1 to MM4) were distinguished upon hierarchical clustering of multiple myeloma. The MM1 subgroup contained samples that were more like monoclonal gammopathy of undetermined significance, whereas the MM4 subgroup contained samples more like multiple myeloma cell lines. The most significant gene expression patterns differentiating MM1 and MM4 were cell cycle control and DNA metabolism genes, and the MM4 subgroup was more likely to have abnormal cytogenetics, elevated serum β2M, elevated creatinine, and deletions of chromosome 13. These are important variables that historically have been linked to poor prognosis.

Gene Expression Changes in Multiple Myeloma

The most significant gene expression changes differentiating the MM1 and MM4 subgroups code for activities that clearly implicate MM4 as having a more proliferative and autonomous phenotype. The most significantly altered gene in the comparison, TYMS (thymidylate synthase), which functions in the prymidine biosynthetic pathway, has been linked to resistance to fluoropyrimidine chemotherapy and also poor prognosis in colorectal carcinomas. Other notable genes upregulated in MM4 were the CAAX farnesyltransferase gene, FTNA. Farnesyltransferase prenylates RAS, a post translational modification required to allow RAS to attach to the plasma membrane. These data suggest that farnesyltransferase inhibitors may be effective in treating patients with high levels of FTNA expression.

Two other genes coding for components of the proteasome pathway, POH1 (26S proteasome-associated pad1 homolog) and UBL1 (ubiquitin-like protein 1) were also overexpressed in MM4. Overexpression of POH1 confers P-glycoprotein-independent, pleotropic drug resistance to mammalian cells. UBL1, also known as sentrin, is involved in many processes including associating with RAD51, RAD52, and p53 proteins in the double-strand repair pathway; conjugating with RANGAP1 involved in nuclear protein import; and importantly for multiple myeloma, protecting against both Fas/Apo-1 (TNFRSF6) or TNFR1-induced apoptosis. In contrast to normal plasma cells, more than 75% of multiple myeloma plasma cells express abundant mRNA for the multidrug resistance gene, lung-resistance-related protein (MVP). These data are consistent with previous reports showing expression of MVP in multiple myeloma is a poor prognostic factor. Given the uniform development of chemotherapy resistance in multiple myeloma, the combined overexpression of POH1 and MVP may have profound influences on this phenotype. The deregulated expression of many genes whose products function in the proteasome pathway may be used in pharmacogenomic analysis in determining the efficacy of proteasome inhibitors like PS-341 (Millennium Pharmaceuticals, Cambridge, Mass.).

Another significantly upregulated gene in MM4 was the single stranded DNA-dependent ATP-dependent helicase (G22P1), which is also known as Ku70 autoantigen. The DNA helicase II complex, made up of p70 and p80, binds preferentially to fork-like ends of double-stranded DNA in a cell cycle-dependent manner. Binding to DNA is thought to be mediated by p70 and dimerization with p80 forms the ATP-dependent DNA-unwinding enzyme (helicase II) and acts as the regulatory component of a DNA-dependent protein kinase (DNPK) which was also significantly upregulated in MM4. The involvement of helicase II complex in DNA double-strand break repair, V(D)J recombination, and notably chromosomal translocations has been proposed. Another upregulated gene was the DNA fragmentation factor (DFFA). Caspase-3 cleaves DFFA-encoded 45 kD subunit at two sites to generate an active factor that produces DNA fragmentation during apoptosis signaling. In light of the many blocks to apoptosis in multiple myeloma, DFFA activation could result in DNA fragmentation, which in turn would activate the helicase II complex that may facilitate chromosomal translocations. It is of note that abnormal karyotypes, and thus chromosomal translocations, are associated with the MM4 subgroup which tended to overexpress these two genes.

Hence, it was demonstrated that direct comparison of gene expression patterns in multiple myeloma and normal plasma cells identified novel genes that could represent fundamental changes associated with malignant transformation of plasma cells.

Progression of multiple myeloma as a hypoproliferative tumor is thought to be linked to a defect in programmed cell death rather than rapid cell replication. Two genes, prohibitin (PHB) and quiescin Q6 (QSCN6), overexpressed in multiple myeloma are involved in growth arrest. Overexpression of these genes may be responsible for the typically low proliferation indices seen in multiple myeloma. It is hence conceivable that therapeutic downregulation of these genes that results in enhanced proliferation could render multiple myeloma cells more susceptible to cell cycle-active chemotherapeutic agents.

The gene coding for CD27, TNFRSF7, the second most significantly underexpressed gene in multiple myeloma, is a member of the tumor necrosis factor receptor (TNFR) superfamily that provides co-stimulatory signals for T and B cell proliferation, B cell immunoglobulin production and apoptosis. Anti-CD27 significantly inhibits induction of Blimp-1 and J-chain transcripts which are turned on in cells committed to plasma cell differentiation, suggesting that ligation of CD27 on B cells may prevent terminal differentiation. CD27 ligand (CD70) prevents IL-10-mediated apoptosis and directs differentiation of $CD27^+$ memory B cells toward plasma cells in cooperation with IL-10. Thus, it is possible that downregulation of CD27 gene expression in multiple myeloma may block an apoptotic program.

Overexpression of CD47 in multiple myeloma may be related to escape of multiple myeloma cells from immune surveillance. Studies have shown that cells lacking CD47 are rapidly cleared from the bloodstream by splenic red pulp macrophages and CD47 on normal red blood cells prevents this elimination.

The gene product of DNA methyltransferase 1, DNMT1, overexpressed in multiple myeloma is responsible for cytosine methylation in mammals and has an important role in epigenetic gene silencing. In fact, aberrant hypermethylation of tumor suppressor genes plays an important role in the development of many tumors. De novo methylation of p16/INK4a is a frequent finding in primary multiple myeloma. Also, recent studies have shown that upregulated expression of DNMTs may contribute to the pathogenesis of leukemia by inducing aberrant regional hypermethylation. DNA methylation represses genes partly by recruitment of the methyl-CpG-binding protein MeCP2, which in turn recruits a histone deacetylase activity. It has been shown that the process of DNA methylation mediated by Dnmt1 may depend on or generate an altered chromatin state via histone deacetylase activity. It is potentially significant that multiple myeloma cases also demonstrate significant overexpression of metastasis-associated 1 (MTA1) gene. MTA1 was originally identified as being highly expressed in metastatic cells. MTA1 has more recently been discovered to be one subunit of the NURD (NUcleosome Remodeling and histone Deacetylation) complex which contains not only ATP-dependent nucleosome disruption activity, but also histone deacetylase activity. Thus, over expression of DNMT1 and MTA1 may have dramatic effects on repressing gene expression in multiple myeloma.

Oncogenes activated in multiple myeloma included ABL and MYC. Although it is not clear whether ABL tyrosine kinase activity is present in multiple myeloma, it is important to note that overexpression of abl and c-myc results in accelerated development of mouse plasmacytomas. Thus, it may be more than a coincidence that multiple myeloma cells significantly overexpresses MYC and ABL.

Chromosomal translocations involving the MYC oncogene and IGH and IGL genes that result in dysregulated MYC expression are hallmarks of Burkitt's lymphoma and experimentally induced mouse plasmacytomas; however, MYC/IGH-associated translocations are rare in multiple myeloma. Although high MYC expression was a common feature in our panel of multiple myeloma, it was quite variable, ranging from little or no expression to highly elevated expression. It is also of note that the MAZ gene whose product is known to bind to and activate MYC expression was significantly upregulated in the MM4 subgroup. Given the important role of MYC in B cell neoplasia, it is speculated that overexpression of MYC, and possibly ABL, in multiple myeloma may have biological and possibly prognostic significance.

EXT1 and EXT2, which are tumor suppressor genes involved in hereditary multiple exostoses, heterodimerize and are critical in the synthesis and display of cell surface heparan sulfate glycosaminoglycans (GAGs). EXT1 is expressed in both multiple myeloma and normal plasma cells. EXT2L was overexpressed in multiple myeloma, suggesting that a functional glycosyltransferase could be created in multiple myeloma. It is of note that syndecan-1 (CD138/SDC1), a transmembrane heparan sulfate proteoglycan, is abundantly expressed on multiple myeloma cells and, when shed into the serum, is a negative prognostic factor. Thus, abnormal GAG-modified SDC1 may be important in multiple myeloma biology. The link of SDC1 to multiple myeloma biology is further confirmed by the recent association of SDC1 in the signaling cascade induced by WNT proto-oncogene products. It has been showed that syndecan-1 (SDC1) is required for Wnt-1-induced mammary tumorigenesis. Data disclosed herein indicated a significant downregulation of WNT10B in primary multiple myeloma cases. It is also of note that the WNT5A gene and the FRZB gene, which codes for a decoy WNT receptor, were also marginally upregulated in newly diagnosed multiple myeloma. Given that WNTs represent a novel class of B cell regulators, deregulating the expression of these growth factors (WNT5A, WNT10B) and their receptors (e.g., FRZB) and genes products that modulate receptor signaling (e.g., SDC1) may be important in the genesis of multiple myeloma.

Genes identified by the present invention that show significantly up-regulated or down-regulated expression in multiple myeloma are potential therapeutic targets for multiple myeloma. Over-expressed genes may be targets for small molecules or inhibitors that decrease their expression. Methods and materials that can be used to inhibit gene expression, e.g. small drug molecules, anti-sense oligo, or antibody would be readily apparent to a person having ordinary skill in this art. On the other hand, under-expressed genes can be replaced by gene therapy or induced by drugs.

Gene Profiles Defining Disease Subgroups

A multivariate stepwise discriminant analysis was used to identify a minimum subset of genes whose expression was intimately associated with malignant features of multiple myeloma. By applying linear regression analysis to the top 50 differentially expressed genes, 14 genes were defined as predictors that are able to differentiate multiple myeloma from normal plasma cells with a high degree of accuracy. When the model was applied to a validation group consisting of 118 multiple myeloma, 6 normal plasma cells and 7 cases of monoclonal gammopathy of undetermined significance (MGUS), an accuracy of classification of more than 99% was achieved. Importantly, 6 of the 7 MGUS cases were classified as multiple myeloma, indicating that MGUS has gene expression features of malignancy. Thus the altered expression of 14 genes out of over 6,000 genes interrogated are capable of defining multiple myeloma. Similar multivariate discriminant analysis also identified a set of 24 genes that can distinguish between the four multiple myeloma subgroups described above.

In addition to identifying genes that were statistically different between normal plasma cells and multiple myeloma plasma cells, the present invention also identified genes, like FGFR3 and CCND1, that demonstrate highly elevated "spiked" expression in subsets of multiple myelomas. Patients with elevated expression of these genes can have significant distribution differences among the four gene expression cluster subgroups. For example, FGFR3 spikes are found in MM1 and MM2 whereas spikes of IFI27 are more likely to be found in MM3 and MM4. Highly elevated expression of the interferon-induced gene IFI27 may be indicative of viral infection, either systemic or specifically within the plasma cells from these patients. Correlation analysis has shown that IFI27 spikes are significantly linked (Pearson correlation coefficient values of 0.77 to 0.60) to elevated expression of 14 interferon-induced genes, including MX1, MX2, OAS1, OAS2, IFIT1, IFIT4, PLSCR1, and STAT1. More recent analysis of a large population of multiple myeloma patients (N=280) indicated that nearly 25% of all patients had spikes of the IFI27 gene. It is of interest to determine whether or not the IFI27 spike patients who cluster in the MM4 subgroup are more likely to have a poor clinical course and to identify the suspected viral infection causing upregulation of this class of genes. In conclusion, spiked gene expression may also be used in the development of clinically relevant prognostic groups.

Finally, the 100% coincidence of spiked FGFR3 or CCND1 gene expression with the presence of t(4; 14)(p14;

q32) or t(11; 14)(q13;q32) translocations, as well as the strong correlations between protein expression and gene expression represent important validations of the accuracy of gene expression profiling and suggests gene expression profiling may eventually supplant the labor intensive and expensive clinical laboratory procedures, such as cell surface marker immunophenotyping and molecular and cellular cytogenetics.

In another embodiment, a feature-subset selection was used to extract genes relevant to specific myeloma subtypes. In this regard, multivariate stepwise discriminant analysis was applied and identified 15 genes that could correctly separate tissue samples into seven subtypes. Examining the expression of the 15 genes thus identified not only would provide important new insights into the diagnosis and pathogenesis of these myeloma subtypes but also may pinpoint useful targets against which novel therapeutic agents could be developed.

Comparison of Multiple Myeloma with Normal Plasma Cell Development

Further, it was also shown that multiple myeloma could be placed into a developmental schema parallel to that of normal plasma cell differentiation. Global gene expression profiling revealed distinct changes in transcription associated with human plasma cell differentiation. Hierarchical clustering analyses with 4866 genes segregated tonsil B cells, tonsil plasma cells, and bone marrow plasma cells. Combining $\chi^2$ and Wilcoxon rank sum tests, 359 previously defined and novel genes significantly (p<0.0005) discriminated tonsil B cells from tonsil plasma cells, and 500 genes significantly discriminated tonsil plasma cells from bone marrow plasma cells. Genes that were differentially expressed in the tonsil B cell to tonsil plasma cell transition were referred as "early differentiation genes" (EDGs) and those differentially expressed in the tonsil plasma cell to bone marrow plasma cell transition were referred as "late differentiation genes" (LDGs). One-way ANOVA was then applied to EDGs and LDGs to identify statistically significant expression differences between multiple myeloma (MM) and tonsil B cells (EDG-MM), tonsil plasma cells (LDG-MM1), or bone marrow plasma cells (LDG-MM2).

Hierarchical cluster analysis revealed that 13/18 (p=0.00005) MM4 cases (a putative poor-prognosis subtype) clustered tightly with tonsil B cells. The other groups (MM1, 2 and 3) failed to show such associations. In contrast, there was tight clustering between tonsil plasma cells and 14/15 (p=0.00001) MM3, and significant similarities were found between bone marrow plasma cells and 14/20 (p=0.00009) MM2 cases. MM1 showed no significant linkage with the normal cell types studied. In addition, XBP1, a transcription factor essential for plasma cell differentiation, exhibited a significant, progressive reduction in expression from MM1 to MM4, consistent with developmental-stage relationships. Therefore, global gene expression patterns linked to late-stage B cell differentiation confirmed and extended a global gene expression-defined classification system of multiple myeloma, suggesting that multiple myeloma represents a constellation of subtypes of disease with unique origins.

Identification of Genes that could be Useful as Diagnostic, Prognostic and Targets in Myeloma The present invention also identified genes that could be useful as diagnostic, prognostic and potential targets in myeloma. 70 genes whose expression was significantly correlated with disease-related survival was identified by performing gene expression analysis of highly purified plasma cells from newly diagnosed myeloma patients; 30% of these genes mapped to chromosome 1. Increased expression of 1q genes and reduced expression of 1p genes were consistent with cytogenetic data of frequent 1q gains and 1p loses in myeloma karyotypes (Nilsson et al., 2003; Gutierrez et al., 2004). Tandem duplications and jumping translocations involving 1q21, caused by decondensation of pericentromeric heterochromatin are features of end stage disease (Sawyer et al., 2005; Sawyer et al., 1998; Le Baccon et al., 2001).

Over expression and amplification of CKS1B, mapping to 1q21 was linked to poor prognosis in newly diagnosed myeloma. Its role in controlling $SCF^{Skp2}$-mediated ubiquitinylation and proteasomal degradation of the cyclin-dependent kinase inhibitor $p27^{Kip1}$ made it an attractive candidate gene. CKS1B protein levels were correlated with gene expression and both inversely correlated with $p27^{Kip1}$ protein levels. Investigations in S. cerevisiae demonstrated an essential role of cks1 in promoting mitosis by modulating the transcriptional activation of CDC20 (Morris et al., 2003). A strong correlation between CKS1B and CDC20 expression (r=0.78; p<0.0001) was observed in the present invention, consistent with CKS1B promoting mitosis by regulating CDC20 expression in human cells. Therefore, the results obtained in the present invention demonstrate that gene dosage-related increase in CKS1B expression led to enhanced degradation of $p27^{Kip1}$ and possibly activation of CDC20.

In context of the recently recognized prognostically relevant genetic subgroups, CKS1B hyper-activation was less frequent in cases with hyperdiploid and normal karyotypes; one-third of those with CCND1-translocations had high CKS1B levels and upto two-thirds of high-risk entities, MAF, MAFB and hyperdiploidy displayed CKS1B hyperactivation (Table 6A). In addition to conferring a poor prognosis among newly diagnosed patients, CKS1B overexpression and amplification were common at relapse in patients lacking these features at diagnosis. Hence, it will be important to determine whether CKS1B amplification emerges in all subgroups and when present, portends rapid disease progression and death.

CKS1B gene amplification along with abnormal metaphase cytogenetics and chromosome 13 deletion accounted for almost 40% of the observed survival variability, underscored that myeloma risk was best assessed by studying molecular and cellular genetics. It is therefore recommended to routinely apply such studies, performed on a single bone marrow sample for appropriate patient stratification in therapeutic trial design.

The impact of new agents such as bortezomib and thalidomide and its derivatives will be profound if their clinical efficacy is extended to genetically defined high-risk myeloma. Since CKS1B directly or indirectly interacts with ubiquitin ligases and/or the proteasome to regulate multiple cell cycle checkpoints (Pagano and Benmaamar, 2003), it is contemplated that new therapeutic strategies that directly target CKS1B or related pathways might represent novel and more specific means of treating de novo high-risk myeloma and might prevent its secondary evolution.

Further, fluorescence in-situ hybridization (FISH) tests for 1q21 amplification and 13 deletion represented a better test for risk assessment that existed. Since the expression of CKS1B highly correlated with the gene copy number and the risk of death increased with the increase in gene copy number, this test could also be used to stage patients at diagnosis, detect residual diseases, predict recurrence and progression of the disease.

In summary, the method of gene expression profiling for multiple myeloma comprises applying nucleic acid samples of isolated plasma cells derived from individuals with or without multiple myeloma to a DNA microarray, and performing hierarchical clustering analysis on data obtained from the microarray to classify the individuals into distinct subgroups such as the MM1, MM2, MM3 and MM4 subgroups disclosed herein. Gene expression profiling will also identify genes with elevated expression in subsets of multiple myeloma patients or genes with significantly different levels of expression in multiple myeloma patients as compared to normal individuals. These genes are potential therapeutic targets for multiple myeloma.

In another embodiment, a group of genes will be identified that can distinguish between normal plasma cells and plasma cells of multiple myeloma. Nucleic acid samples of isolated plasma cells derived from individuals with or without multiple myeloma were applied to a DNA microarray, and hierarchical clustering analysis was performed on data obtained from the microarray. Genes with statistically significant differential expression patterns were identified, and linear regression analysis was used to identify a group of genes that is capable of accurate discrimination between normal plasma cells and plasma cells of multiple myeloma. This analysis can also identify a group of genes that is capable of accurate discrimination between subgroups of multiple myeloma.

The expression levels of a group of 14 genes thus identified could be used for diagnosis of multiple myeloma. Significant differential expression of these genes would indicate that such individual has multiple myeloma or a subgroup of multiple myeloma. Gene expression levels can be examined at nucleic acid level or protein level according to methods well known to one of skill in the art.

An another embodiment, comprises a method of diagnosis for multiple myeloma based on examining the expression levels of a group of genes comprising CST6, RAB7L1, MAP4K3, HRASLS2, TRAIL, IG, FGL2, GNG11, MCM2, FLJ10709, CCND1, MAF, MAFB, FGFR3, and MMSET. CCND1, MAF, MAFB, FGFR3, and MMSET expression can be determined by and are correlated with chromosomal translocation such as t(4; 14)(p21;q32), t(14; 16)(q32;q23), t(14; 20)(q32;q13), and t(11; 14)(q13;q32). Gene expression levels of this group of genes would classify an individual into one of 7 groups of myeloma (groups 1-7). Individual in myeloma groups 1, 2, 3 and 6 would have poor prognosis compared to individual in myeloma groups 4, 5 and 7. Group 1 is defined by downregulation of CST6, RAB7L1, MAP4K3, HRASLS2, GNG11, MCM2 and FLJ10709, and overexpression of TRAIL, IG and FGFL2. Group 2 is defined by downregulation of CST6, RAB7L1, MAP4K3, HRASLS2, IG, FGFL2, MCM2 and FLJ10709, and overexpression of TRAIL and GNG11. Group 3 is defined by overexpression of CCND1, or translocation t(11; 14)(q13; q32). Group 4 is defined by downregulation of CST6, RAB7L1, MAP4K3, HRASLS2, IG, FGFL2, and GNG11, and overexpression of TRAIL, MCM2 and FGFL2. Group 5 is defined by overexpression of MAF or MAFB, or translocation t(14; 16)(32;q23) or t(14; 20)(q32;q13). Group 6 is defined by overexpression of CST6, RAB7L1, MAP4K3, and HRASLS2, and downregulation of TRAIL. Group 7 is defined by overexpression of FGFR3 or MMSET, or translocation t(4; 14)(p21;q32).

In yet another embodiment are methods of treatment for multiple myeloma. Such methods involve inhibiting expression of one of the genes or increasing expression of one of the genes. Methods of inhibiting or increasing gene expression such as those using anti-sense oligonucleotide or antibody are well known to one of skill in the art. Inhibiting gene expression can be achieved through RNA interference using so called siRNA. Gene expression enhancement might be through gene therapy.

In still yet another embodiment is a method of developmental stage-based classification for multiple myeloma. Nucleic acid samples of isolated B cells and plasma cells derived from individuals with or without multiple myeloma were applied to a DNA microarray, and hierarchical clustering analysis performed on data obtained from the microarray will classify the multiple myeloma cells according to the developmental stages of normal B cells and plasma cells. In general, normal B cells and plasma cells are isolated from tonsil, bone marrow, mucoal tissue, lymph node or peripheral blood.

In another embodiment, there is a method of controlling bone loss in an individual by inhibiting the expression of the DKK1 gene (accession number NM012242). In general, DKK1 expression can be inhibited by anti-sense oligonucleotides or anti-DKK1 antibodies. In another embodiment, bone loss can be controlled by a pharmacological inhibitor of DKK1 protein. Preferably, the individual having bone loss may have multiple myeloma, osteoporosis, post-menopausal osteoporosis or malignancy-related bone loss that is caused by breast cancer metastasis or prostate cancer metastasis.

The present invention is drawn to a method of identifying genes associated with a phenotype of interest in a population, comprising: isolating cells from individuals within the population, profiling gene expression in the cells using oligonucleotide microarrays, correlating the gene expression profiles in the cells with the phenotype of interest, thereby identifying genes associated with the phenotype of interest in the population. Generally, the phenotype of interest is disease-related survival, response to a drug.

The present invention is also drawn to a method of diagnosing an individual with myeloma, comprising the steps of: (a) obtaining a bone marrow sample from the individual, and (b) determining an amplification of a gene on chromosome 1q21 or a deletion of chromosome 13 in the sample, thereby diagnosing the individual with myeloma. This method comprises predicting relapse or progression of the disease in the individual based on the extent of amplification of the gene on chromosome 1q21, where an increase in the amplification of the gene indicates relapse or progression of the disease in the individual. Specifically, the amplified gene is CKS1B.

The present invention is further drawn to a method of identifying an individual having high-risk myeloma comprising the steps of: (a) obtaining a bone marrow sample from the individual; and (b) determining an amplification of a gene on chromosome 1q21, wherein the amplification of the gene increases the risk of developing myeloma, thereby identifying the individual having high-risk myeloma. This method further comprises: predicting survival of the individual having high-risk myeloma by detecting an amplification of the gene on chromosome 1q21, where the amplification of the gene on chromosome 1q21 is associated with high-incidence of myeloma-related death. Specifically, the amplified gene is CKS1B.

The present invention is still further drawn to a method of screening for drugs useful in treating high-risk myeloma, comprising: contacting a sample comprising CKS1B with a drug, and determining the inhibitory effect of the drug on amplification, over-expression or activity of CKS1B gene, thereby screening for drugs useful in treating high-risk myeloma.

Alternatively, the present invention is also drawn to a method of screening for drugs useful in treating high-risk myeloma, comprising; contacting a sample comprising CKS1B with a drug, and determining the inhibitory effect of the drug on amplification, over-expression or activity of the CKS1B protein, thereby screening for drugs useful in treating high-risk myeloma. As is known to one skilled in the art that such a drug will also target components that are either upstream or downstream of this gene or protein in a cell cycle-related pathway.

The present invention is further drawn to a method of treating an individual having a high-risk myeloma, comprising: administering to the individual a compound that inhibits amplification, over-expression or activity of CKS1B gene. Examples of such compounds although not limited to include compounds such as a peptide nucleic acid (PNA), RNA-mediated interference. Alternatively, the present invention is also drawn to a method of treating an individual having a high-risk myeloma, comprising: administering to the individual a compound that inhibits amplification, over-expression or activity of CKS1B protein. Examples of such compounds although not limited to include compounds such as an antibody, a CKS1B antisense RNA or a small molecule inhibitor.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Cell Isolation and Analysis

Samples for the following studies included plasma cells from 74 newly diagnosed cases of multiple myeloma, 5 subjects with monoclonal gammopathy of undetermined significance, 7 samples of tonsil B lymphocytes (tonsil BCs), 11 samples of tonsil plasma cells (tonsil PCs), and 31 bone marrow PCs derived from normal healthy donor. Multiple myeloma cell lines (U266, ARP1, RPMI-8226, UUN, ANBL-6, CAG, and H929 (courtesy of P. L. Bergsagel) and an Epstein-Barr virus (EBV)-transformed B-lymphoblastoid cell line (ARH-77) were grown as recommended (ATCC, Chantilly, Va.).

Tonsils were obtained from patients undergoing tonsillectomy for chronic tonsillitis. Tonsil tissues were minced, softly teased and filtered. The mononuclear cell fraction from tonsil preparations and bone marrow aspirates were separated by a standard Ficoll-Hypaque gradient (Pharmacia Biotech, Piscataway, N.J.). The cells in the light density fraction (S.G.≤1.077) were resuspended in cell culture media and 10% fetal bovine serum, RBC lysed, and several PBS wash steps were performed. Plasma cell isolation was performed with anti-CD138 immunomagnetic bead selection as previously described (Zhan et al., 2002). B lymphocyte isolation was performed using directly conjugated monoclonal mouse anti-human CD19 antibodies and the AutoMacs automated cell sorter (Miltenyi-Biotec, Auburn, Calif.).

For cytology, approximately 40,000 purified tonsil BC and PC mononuclear cells were cytocentrifuged at 1000×g for 5 min at room temperature. For morphological studies, the cells were immediately processed by fixing and staining with DiffQuick fixative and stain (Dade Diagnostics, Aguada, PR). For immunofluorescence, slides were treated essentially as described (Shaughnessy et al., 2000). Briefly, slides were air-dried overnight, then fixed in 100% ethanol for 5 min at room temperature and baked in a dry 37° C. incubator for 6 hr. The slides were then stained with 100 µl of a 1:20 dilution of goat anti-human-kappa immunoglobulin light chain conjugated with 7-amino-4-methylcourmarin-3-acitic acid (AMCA) (Vector Laboratories, Burlingame, Calif.) for 30 min in a humidified chamber. After incubation, the slides were washed two times in 1×PBS+0.1% NP-40 (PBD). To enhance the AMCA signal, the slides were incubated with 100 µl of a 1:40 dilution of AMCA-labeled rabbit-anti-goat IgG antibody and incubated for 30 min at room temperature in a humidified chamber. Slides were washed 2 times in 1×PBD. The slides were then stained with 100 µl of a 1:100 dilution of goat anti-human-lambda immunoglobulin light chain conjugated with FITC (Vector Laboratories, Burlingame, Calif.) for 30 min in a humidified chamber; the slides were washed two times in 1×PBD. Then the slides were stained with propidium iodide at 0.1 µg/ml in 1×PBS for 5 min, washed in 1×PBD, and 10 µl anti-fade (Molecular Probes, Eugene, Oreg.) was added and coverslips were placed. Cytoplasmic immunoglobulin light chain-positive PCs were visualized using an Olympus BX60 epi-fluorescence microscope equipped with appropriate filters. The images were captured using a Quips XL genetic workstation (Vysis, Downers Grove, Ill.).

Both unpurified mononuclear cells and purified fractions from tonsil BCs, tonsil PCs, and bone marrow PCs were subjected to flow cytometric analysis of CD marker expression using a panel of antibodies directly conjugated to FITC or PE. Markers used in the analysis included FITC-labeled CD20, PE-labeled CD38, FITC-labeled or ECD-labeled CD45, PE- or PC5-labeled CD138 (Beckman Coulter, Miami, Fla.). For detection of CD138 on PCs after CD138 selection, we employed an indirect detection strategy using a FITC-labeled rabbit anti-mouse IgG antibody (Beckman Coulter) to detect the mouse monoclonal anti-CD138 antibody BB4 used in the immunomagnetic selection technique. Cells were taken after Ficoll Hypaque gradient or after cell purification, washed in PBS, and stained at 4° C. with CD antibodies or isotype-matched control G1 antibodies (Beckman Coulter). After staining, cells were resuspended in 1×PBS and analyzed using a Epics XL-MCL flow cytometry system (Beckman Coulter).

Example 2

Preparation of Labeled cRNA and Hybridization to High-Density Microarray

Total RNA was isolated with RNeasy Mini Kit (Qiagen, Valencia, Calif.). Double-stranded cDNA and biotinylated cRNA were synthesized from total RNA and hybridized to HuGeneFL GENECHIP® microarrays (Affymetrix, Santa Clara, Calif.), which were washed and scanned according to procedures developed by the manufacturer. The arrays were scanned using Hewlett Packard confocal laser scanner and visualized using Affymetrix 3.3 software (Affymetrix). Arrays were scaled to an average intensity of 1,500 and analyzed independently.

Example 3

GENECHIP® Microarray Data Analysis

To efficiently manage and mind high-density oligonucleotide DNA microarray data, a new data-handling tool was developed. GENECHIP® miroarray-derived expression data was stored on an MS SQL Server. This database was linked, via an MS Access interface called Clinical Gene-Organizer to multiple clinical parameter databases for multiple myeloma patients. This Data Mart concept allows gene expression profiles to be directly correlated with clinical parameters and clinical outcomes using standard statistical software. All data used in the present analysis were derived from Affymetrix 3.3 software. GENECHIP® microarray 3.3 output files are given (1) as an average difference (AD) that represents the difference between the intensities of the sequence-specific perfect match probe set and the mismatch probe set, or (2) as an absolute call (AC) of present or absent as determined by the GENECHIP® microarray 3.3 algorithm. Average difference calls were transformed by the natural log after substituting any sample with an average difference of <60 with the value 60 (2.5 times the average Raw Q). Statistical analysis of the data was performed with software packages SPSS 10.0 (SPSS, Chicago, Ill.), S-Plus 2000 (Insightful Corp., Seattle, Wash.), and Gene Cluster/Treeview (Eisen et al., 1998).

To differentiate four distinct subgroups of multiple myeloma (MM1, MM2, MM3 and MM4), hierarchical clustering of average linkage clustering with the centered correlation metric was employed. The clustering was done on the average difference data of 5,483 genes. Either Chi square ($\chi^2$) or Fisher's exact test was used to find significant differences between cluster groups with the AC data. To compare the expression levels, the non-parametric Wilcoxon rank sum (WRS) test was used. This test uses a null hypothesis that is based on ranks rather than on normally distributed data. Before the above tests were performed, genes that were absent (AC) across all samples were removed; 5,483 genes were used in the analyses. Genes that were significant (p<0.0001) for both the $\chi^2$ test and the WRS test were considered to be significantly differentially expressed.

Clinical parameters were tested across multiple myeloma cluster groups. ANOVA test was used to test the continuous variables, and $\chi^2$ test of independence or Fisher's exact test was applied to test discrete variables. The natural log of the average difference data was used to find genes with a "spiked profile" of expression in multiple myeloma. Genes were identified that had low to undetectable expression in the majority of patients and normal samples (no more than 4 present absolute calls [P-AC]). A total of 2,030 genes fit the criteria of this analysis. The median expression value of each of the genes across all patient samples was determined. For the $i^{th}$ gene, this value was called medgene (i). The $i^{th}$ gene was a "spiked" gene if it had at least 4 patient expression values >2.5+medgene (i). The constant 2.5 was based on the log of the average difference data. These genes that were "spiked" were further divided into subsets according to whether or not the largest spike had an average difference expression value greater than 10,000.

To determine transcriptional changes associated with human plasma cell differentiation, a total of 4866 genes were scanned across 7 cases each of tonsil B cells, tonsil plasma cells, and bone marrow plasma cells. The 4866 genes were derived from 6800 by filtering out all control genes, and genes not fulfilling the test of Max-Min<1.5 (1.5 being the natural log of the average difference). The $\chi^2$ test was used to eliminate genes with absent absolute call (AAC). For example, in the tonsil plasma cell to bone marrow plasma cell comparison, genes with $\chi^2$ values greater than 3.84 (p<0.05) or having "present" AC (PAC) in more than half of the samples in each group were retained. In the tonsil B cell to tonsil plasma cell and tonsil plasma cell to bone marrow plasma cell comparisons, 2662 and 2549 genes were retained as discriminating between the two groups, respectively. To compare gene expression levels, the non-parametric Wilcoxon Rank Sum (WRS) test was used to compare two groups using natural log transformed AD. The cutoff p value depended on the sample size, the heterogeneity of the two comparative populations (tonsil B cells, tonsil plasma cells, and bone marrow plasma cells showed a higher degree of stability in AD), and the degree of significance. In this analysis, 496 and 646 genes were found to be significantly (p<0.0005) differentially expressed in the tonsil B cell versus tonsil plasma cell and tonsil plasma cell versus bone marrow plasma cell comparisons, respectively. To define the direction of significance (expression changes being up or down in one group compared with the other), the non-parametric Spearman correlation test of the AD was employed.

Genes that were significantly differentially expressed in the tonsil B cell to tonsil plasma cell transition were referred as "early differentiation genes" (EDGs) and those differentially expressed in the tonsil plasma cell to bone marrow plasma cell transition were referred as "late differentiation genes" (LDGs). Previously defined and novel genes were identified that significantly discriminated tonsil B cells from tonsil plasma cells (359 genes) and tonsil plasma cells from bone marrow plasma cells (500 genes).

To classify multiple myeloma with respect to EDG and LDG, 74 newly diagnosed cases of multiple myeloma and 7 tonsil B cell, 7 tonsil plasma cell, and 7 bone marrow plasma cell samples were tested for variance across the 359 EDGs and 500 LDGs. The top 50 EDGs that showed the most significant variance across all samples were defined as early differentiation genes for myeloma (EDG-MM). Likewise, the top 50 LDGs showing the most significant variance across all samples were identified as late differentiation genes for myeloma-1 (LDG-MM1). Subtracting the LDG-MM1 from the 500 LDG and then applying one-way ANOVA test for variance to the remaining genes identified the top 50 genes showing similarities between bone marrow plasma cells and multiple myeloma. These genes were defined as LDG-MM2.

Hierarchical clustering was applied to all samples using 30 of the 50 EDG-MM. A total of 20 genes were filtered out with Max-Min<2.5. This filtering was performed on this group because many of the top 50 EDG-MM showed no variability across multiple myeloma and thus could not be used to distinguish multiple myeloma subgroups. A similar clustering strategy was employed to cluster the samples using the 50 LDG-MM1 and 50 LDG-MM2; however, in these cases all 50 significant genes were used in the cluster analysis.

Example 4

RT-PCR and Immunohistochemistry

RT-PCR for the FGFR3 MMSET was performed on the same cDNAs used in the microarray analysis. Briefly, cDNA was mixed with the IGJH2 (5'-CAATGGTCACCGTCTCT-TCA-3', SEQ ID No. 1) primer and the MMSET primer (5'-CCTCAATTTCCTGAAATTGGTT-3', SEQ ID No. 2). PCR reactions consisted of 30 cycles with a 58° C. annealing temperature and 1-minute extension time at 72° C. using a Perking Elmer GeneAmp 2400 thermocycler (Wellesley, Mass.). PCR products were visualized by ethidium bromide staining after agarose gel electrophoresis.

Immunohistochemical staining was performed on a Ventana ES (Ventana Medical Systems, Tucson, Ariz.) using Zenker-fixed paraffin-embedded bone marrow sections, an avidin-biotin peroxidase complex technique (Ventana Medical Systems), and the antibody L26 (CD20, Ventana Medical Systems). Heat-induced epitope retrieval was performed by microwaving the sections for 28 minutes in a 1.0-mmol/L concentration of citrate buffer at pH 6.0.

Example 5

Interphase FISH

For interphase detection of the t(11; 14)(q13;q32) translocation fusion signal, a LSI IGH/CCND1 dual-color, dual-fusion translocation probe was used (Vysis, Inc, Downers Grove, Ill.). The TRI-FISH procedure used to analyze the samples has been previously described. Briefly, at least 100 clonotypic plasma cells identified by cIg staining were counted for the presence or absence of the translocation fusion signal in all samples except one, which yielded only 35 plasma cells. A multiple myeloma sample was defined as having the translocation when >25% of the cells contained the fusion.

Example 6

Hierarchical Clustering of Plasma Cell Gene Expression Demonstrates Class Distinction As a result of 656,000 measurements of gene expression in 118 plasma cell samples, altered gene expression in the multiple myeloma samples was identified. Two-dimensional hierarchical clustering differentiated cell types by gene expression when performed on 5,483 genes that were expressed in at least one of the 118 samples (FIG. 1A). The sample dendrogram derived two major branches (FIGS. 1A and 1D). One branch contained all 31 normal samples and a single monoclonal gammopathy of undetermined significance case whereas the second branch contained all 74 multiple myeloma and 4 monoclonal gammopathy of undetermined significance cases and the 8 cell lines. The multiple myeloma-containing branch was further divided into two sub-branches, one containing the 4 monoclonal gammopathy of undetermined significance and the other the 8 multiple myeloma cell lines. The cell lines were all clustered next to one another, thus showing a high degree of similarity in gene expression among the cell lines. This suggested that multiple myeloma could be differentiated from normal plasma cells and that at least two different classes of multiple myeloma could be identified, one more similar to monoclonal gammopathy of undetermined significance and the other similar to multiple myeloma cell lines.

Hierarchical clustering analysis with all 118 samples together with duplicate samples from 12 patients (plasma cells taken 24 hr or 48 hr after initial sample) were repeated to show reproducibility of the technique and analysis. All samples from the 12 patients studied longitudinally were found to cluster adjacent to one another. This indicated that gene expression in samples from the same patient were more similar to each other than they were to all other samples (data not shown).

In addition to the demonstration of reproducibility of clustering noted above, three microarray analyses were also performed on a single source of RNA from one patient. When included in the cluster analysis, the three samples clustered adjacent to one another. Consistent with the manufacturer's specification, an analysis of the fold changes seen in the samples showed that <2% of all genes had a >2-fold difference. Hence, these data indicated reproducibility for same samples.

The clustergram (FIG. 1A) showed that genes of unrelated sequence but similar function clustered tightly together along the vertical axis. For example, a particular cluster of 22 genes, primarily those encoding immunoglobulin molecules and major histocompatibility genes, had relatively low expression in multiple myeloma plasma cells and high expression in normal plasma cells (FIG. 1B). This was anticipated, given that the plasma cells isolated from multiple myeloma are clonal and hence only express single immunoglobulin light-chain and heavy-chain variable and constant region genes, whereas plasma cells from normal donors are polyclonal and express many different genes of these two classes. Another cluster of 195 genes was highly enriched for numerous oncogenes/growth-related genes (e.g., MYC, ABU, PHB, and EXT2), cell cycle-related genes (e.g., CDC37, CDK4, and CKS2), and translation machinery genes (EIF2, EIF3, HTF4A, and TFIIA) (FIG. 1C). These genes were all highly expressed in MM, especially in multiple myeloma cell lines, but had low expression levels in normal plasma cells.

Example 7

Figure 1E:
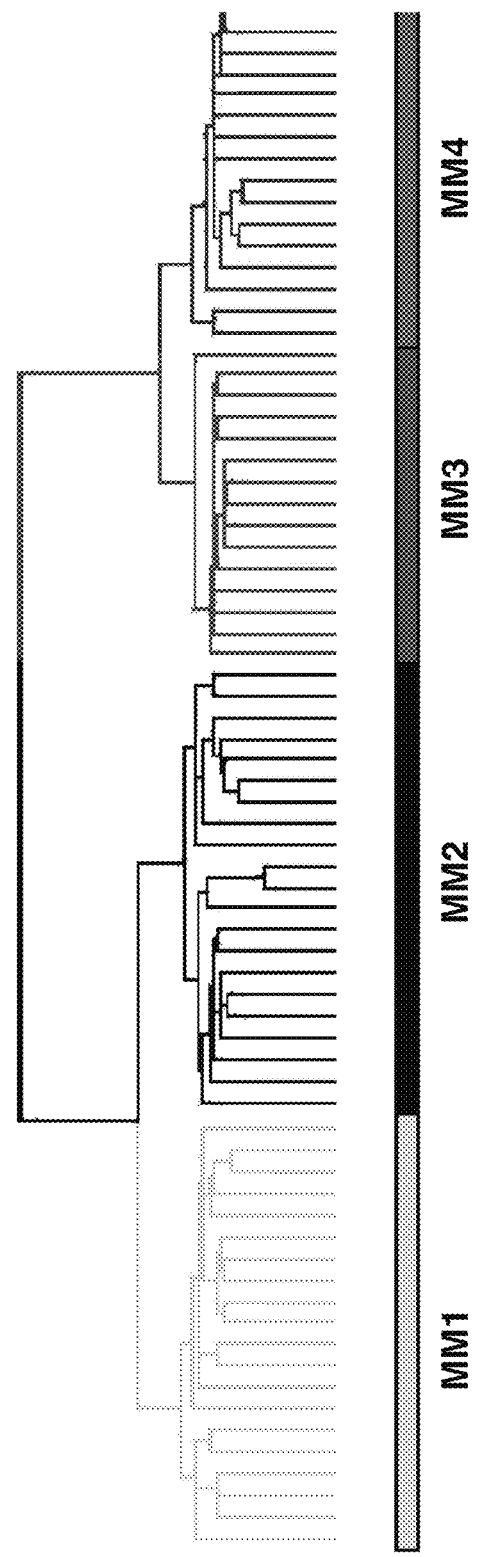
FIG. 1E shows dendrogram of a hierarchical cluster analysis of 74 cases of newly diagnosed untreated multiple myeloma alone (clustergram note shown). Two major branches contained two distinct cluster groups. The subgroups under the right branch, designated MM1 (light blue) and MM2 (blue) were more related to the monoclonal gammopathy of undetermined significance cases in FIG. 1D. The two subgroups under the left branch, designated MM3 (violet) and MM4 (red) represent samples that were more related to the multiple myeloma cell lines in FIG. 1D.

Hierarchical Clustering of Newly Diagnosed Multiple Myeloma Identifies Four Distinct Subgroups Two-dimensional cluster analysis was performed on the 74 multiple myeloma cases alone. The sample dendrogram identified two major branches with two distinct subgroups within each branch (FIG. 1E). The four subgroups were designated MM1, MM2, MM3, and MM4 containing 20, 21, 15, and 18 patients respectively. The MM1 subgroup represented the patients whose plasma cells were most closely related to the monoclonal gammopathy of undetermined significance plasma cells and MM4 were most like the multiple myeloma cell lines (see FIG. 1D). These data suggested that the four gene expression subgroups were authentic and might represent four distinct clinical entities.

Differences in gene expression across the four subgroups were then examined using the $\chi^2$ and WRS tests (Table 1). As expected the largest difference was between MM1 and MM4 (205 genes) and the smallest difference was between MM1 and MM2 (24 genes). Next, the top 30 genes turned on or upregulated in MM4 as compared with MM1 were examined (Table 2). The data demonstrated that 13 of 30 most significant genes (10 of the top 15 genes) were involved in DNA replication/repair or cell cycle control. Thymidylate synthase (TYMS), which was present in all 18 samples comprising the MM4 subgroup, was only present in 3 of the 20 MM1 samples and represented the most significant gene in the $\chi^2$ test. The DNA mismatch repair gene, mutS (*E. coli*) homolog 2 (MSH2) with a WRS p value of $2.8\times10^{-6}$ was the most significant gene in the WRS test. Other notable genes in the list included the CAAX farnesyltransferase (FNTA), the transcription factors enhancer of zeste homolog 2 (EZH2) and MYC-associated zinc finger protein (MAZ), eukaryotic translation initiation factors (EIF2S1 and EIF2B1), as well as the mitochondrial translation initiation factor 2 (MTIF2), the chaperone (CCT4), the UDP-glucose pyrophosphorylase 2 (IUGP2), and the 26S proteasome-associated pad1 homolog (POH1).

To assess the validity of the clusters with respect to clinical features, correlations of various clinical parameters across the 4 subgroups were analyzed (Table 3). Of 17 clinical variables tested, the presence of an abnormal karyotype (p=0.0003) and serum β2M levels (p=0.0005) were significantly different among the four subgroups and increased creatinine (p=0.06) and cytogenetic deletion of chromosome 13 (p=0.09) were marginally significant. The trend was to have higher β2M and creatinine as well as an abnormal karyotype and chromosome 13 deletion in the MM4 subgroup as compared with the other 3 subgroups.

TABLE 1

Differences In Gene Expression Among Multiple Myeloma Subgroups

| Comparison | Range of WRS* p Values | Number of Genes |
|---|---|---|
| MM1 vs MM4 | .00097 to $9.58 \times 10^{-7}$ | 205 |
| MM2 vs MM4 | .00095 to $1.0410^{-6}$ | 162 |
| MM3 vs MM4 | .00098 to $3.7510^{-6}$ | 119 |
| MM1 vs MM3 | .00091 to $6.2710^{-6}$ | 68 |
| MM2 vs MM3 | .00097 to $1.9810^{-5}$ | 44 |
| MM1 vs MM2 | .00083 to $2.9310^{-5}$ | 24 |

*Wilcoxon rank sum test. Comparisons are ordered based on the number of significant genes. Comparisons have a WRS p value < 0.001.

TABLE 3

Clinical Parameters Linked To Multiple Myeloma Subgroups

| | Multiple Myeloma Subgroups | | | | |
|---|---|---|---|---|---|
| Clinical Parameter | 1 | 2 | 3 | 4 | p value |
| Abnormal cytogenetics | 40.0% | 5.3% | 53.3% | 72.2% | .00028 |
| Average β2-microglobulin (mg/L) | 2.81 | 2.73 | 4.62 | 8.81 | .00047 |

ANOVA, Chi square, and Fisher's exact tests were used to determine significance.

Example 8

Figure 2:
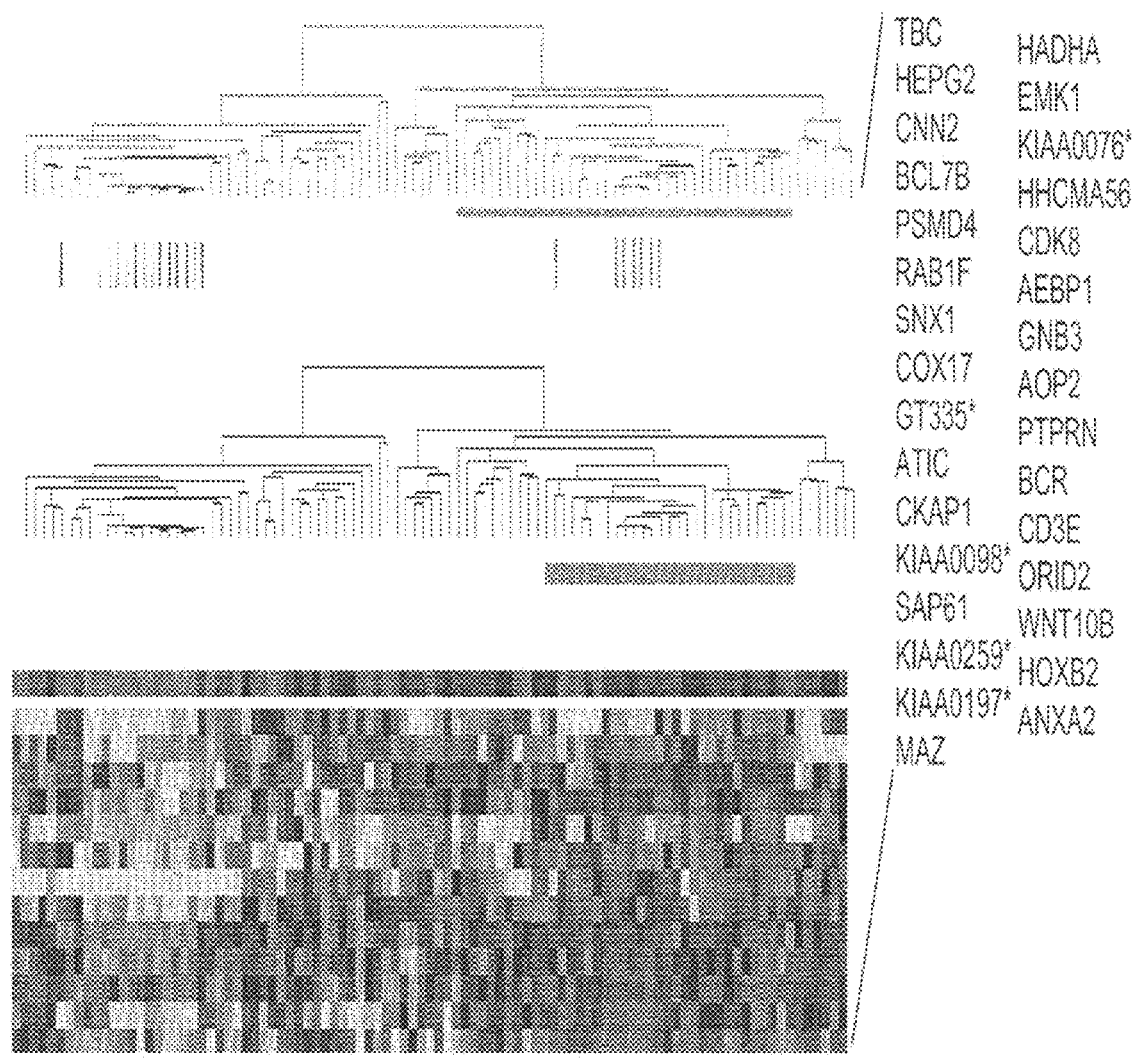
FIG. 2 shows two-dimensional hierarchical cluster analysis of experimental expression profiles and gene behavior of 30 EDG-MM. B cells, tonsil and bone marrow plasma cells, and multiple myeloma (MM) samples were analyzed using a cluster-ordered data table. The tonsil B cell, tonsil plasma cell, bone marrow plasma cell samples are indicated by red, blue, and golden bars respectively. The nomenclature for the 74 MM samples is as indicated in Zhan et al. (2002a). Along the vertical axis, the analyzed genes are arranged as ordered by the clustering algorithm. The genes with the most similar patterns of expression are placed adjacent to each other. Both sample and gene groupings can be further described by following the solid lines (branches) that connect the individual components with the larger groups. The tonsil B cell cluster is identified by the horizontal red bar. The color of each cell in the tabular image represents the expression level of each gene, with red representing an expression greater than the mean, green representing an expression less than the mean, and the deeper color intensity representing a greater magnitude of deviation from the mean.
Figure 3:
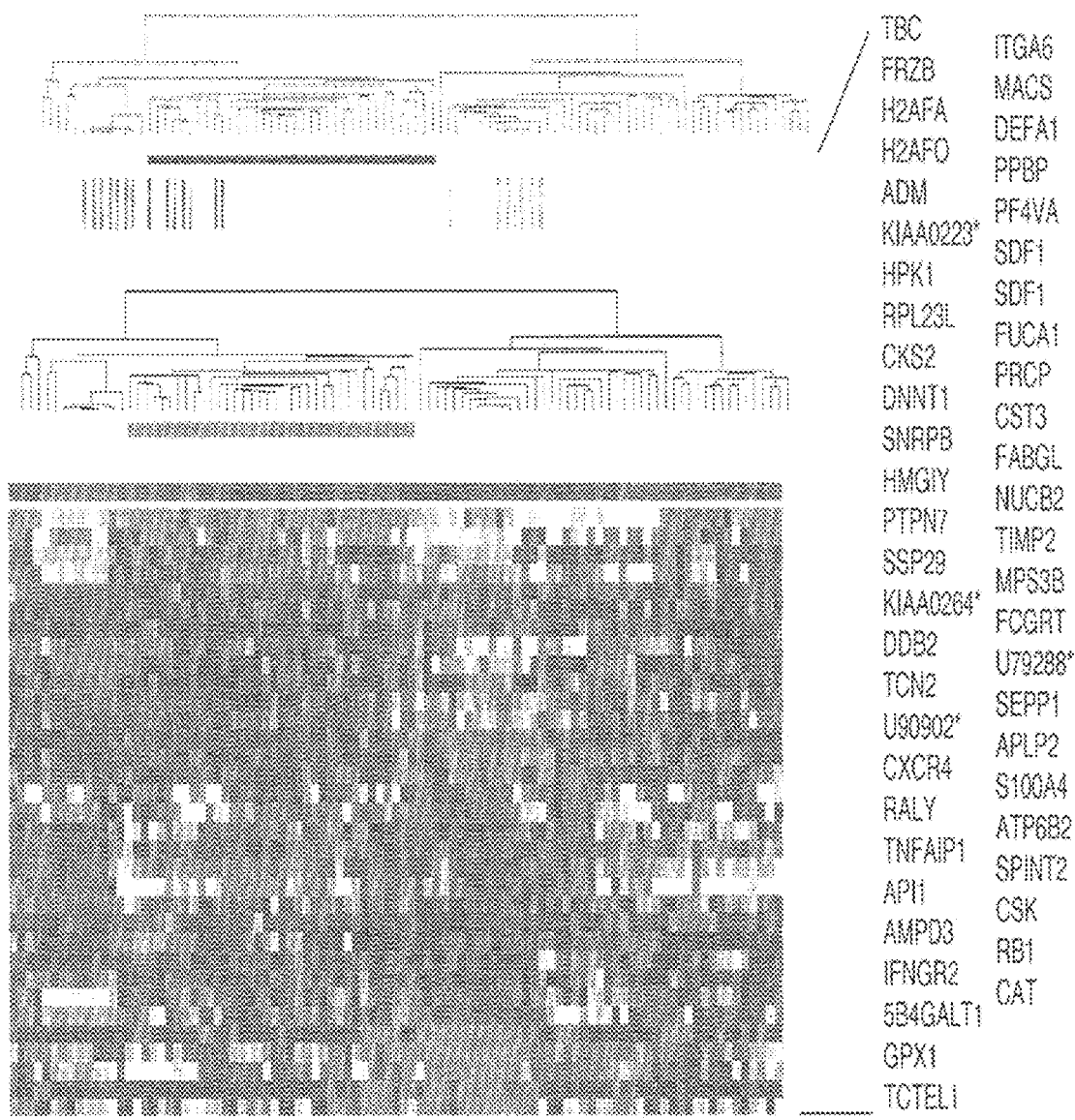
FIG. 3 shows two-dimensional hierarchical cluster analysis of experimental expression profiles and gene behavior of 50 LDG-MM1 genes. Genes are plotted along the vertical axis (right side), and experimental samples are plotted along the top horizontal axis by their similarity. The tonsil plasma cell cluster is identified by a horizontal blue bar. Tonsil B cell, tonsil plasma cell, and bone marrow plasma cell samples are indicated as in FIG. 18.
Figure 4:
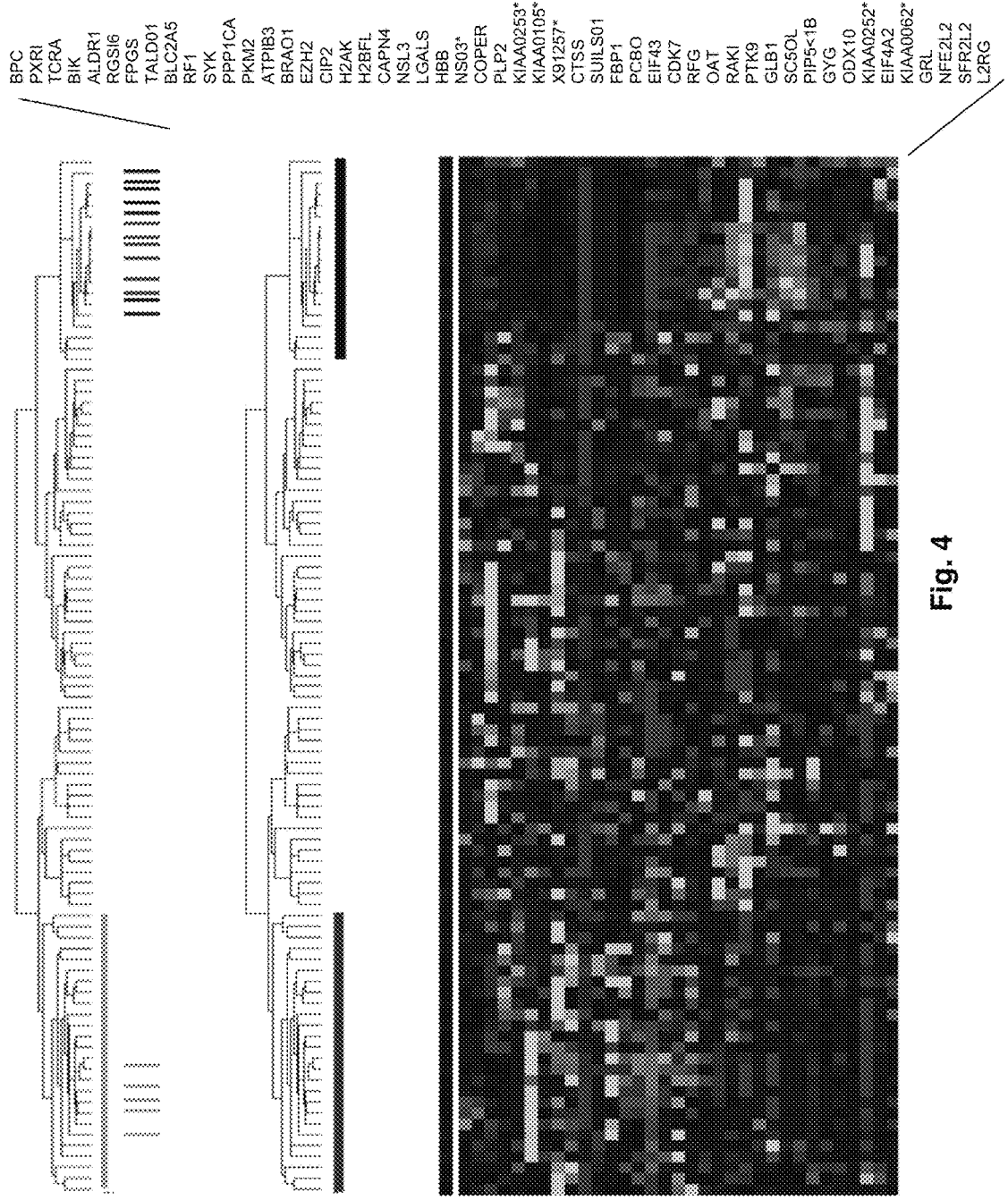
FIG. 4 shows two-dimensional hierarchical cluster analysis of experimental expression profiles and gene behavior of 50 LDG-MM2 genes. Genes are plotted along the vertical axis (right side), and experimental samples are plotted along the top horizontal axis by their similarity. The bone marrow plasma cell cluster is identified by a horizontal golden bar. Tonsil B cell, tonsil plasma cell, and bone marrow plasma cell samples are indicated as in FIG. 18.

Hierarchical Cluster Analysis with EDG-MM, LDG-MM1, and LDG-MM2 Reveals Developmental Stage-Based Classification of Multiple Myeloma To identify whether variability in gene expression seen in multiple myeloma (MM) might be used to discern subgroups of disease, hierarchical cluster analysis was performed on 74 newly diagnosed MM, 7 tonsil B cell, 7 tonsil plasma cell, and 7 bone marrow samples using the EDG-MM (FIG. 2), LDG-MM1 (FIG. 3), and LDG-MM2 (FIG. 4). Hierarchical clustering was applied to all samples using 30 of the 50 EDG-MM. A total of 20 genes were filtered out with Max-Min<2.5. This filtering was performed on this group

TABLE 2

The 30 Most Differentially Expressed Genes In A Comparison Of MM1 And MM4 Subgroups

| Accession | Function | Gene Symbol | MM1 (N = 20) | MM4 (N = 18) | Chi Square | WRS‡ p Value |
|---|---|---|---|---|---|---|
| D00596 | DNA replication | TYMS | 3 | 18 | 24.35 | $1.26 \times 10^{-4}$ |
| U35835 | DNA repair | PRKDC | 2 | 17 | 23.75 | $4.55 \times 10^{-6}$ |
| U77949 | DNA replication | CDC6 | 1 | 13 | 15.62 | $5.14 \times 10^{-6}$ |
| U91985 | DNA fragmentation | DFFA | 1 | 12 | 13.38 | $6.26 \times 10^{-5}$ |
| U61145 | transcription | EZH2 | 4 | 15 | 12.77 | $1.67 \times 10^{-4}$ |
| U20979 | DNA replication | CHAF1A | 2 | 12 | 10.75 | $1.10 \times 10^{-4}$ |
| U03911 | DNA repair | MSH2 | 0 | 9 | 10.48 | $2.88 \times 10^{-6}$ |
| X74330 | DNA replication | PRIM1 | 0 | 9 | 10.48 | $9.36 \times 10^{-6}$ |
| X12517 | SnRNP | SNR PC | 0 | 9 | 10.48 | $5.26 \times 10^{-6}$ |
| D85131 | transcription | MAZ | 0 | 9 | 10.48 | $1.08 \times 10^{-5}$ |
| L00634 | farnesyltransferase | FNTA | 10 | 18 | 9.77 | $7.28 \times 10^{-5}$ |
| U21090 | DNA replication | POLD2 | 11 | 18 | 8.27 | $8.05 \times 10^{-5}$ |
| X54941 | cell cycle | CKS1 | 10 | 17 | 7.07 | $1.26 \times 10^{-4}$ |
| U62136 | cell cycle | UBE2V2 | 13 | 18 | 5.57 | $4.96 \times 10^{-6}$ |
| D38076 | cell cycle | RANBP1 | 13 | 18 | 5.57 | $7.34 \times 10^{-6}$ |
| X95592 | unknown | C1D† | 13 | 18 | 5.57 | $1.10 \times 10^{-4}$ |
| X66899 | cell cycle | EWSR1 | 14 | 18 | 4.35 | $1.89 \times 10^{-4}$ |
| L34600 | translation initiation | MTIF2 | 14 | 18 | 4.35 | $3.09 \times 10^{-5}$ |
| U27460 | Metabolism | IUGP2 | 15 | 18 | 3.22 | $1.65 \times 10^{-4}$ |
| U15009 | SnRNP | SNRPD3 | 15 | 18 | 3.22 | $1.47 \times 10^{-5}$ |
| J02645 | translation initiation | EIF2S1 | 16 | 18 | 2.18 | $7.29 \times 10^{-5}$ |
| X95648 | translation initiation | EIF2B1 | 16 | 18 | 2.18 | $1.45 \times 10^{-4}$ |
| M34539 | calcium signaling | FKBP1A | 18 | 18 | 0.42 | $1.71 \times 10^{-5}$ |
| J04611 | DNA repair | G22P1 | 18 | 18 | 0.42 | $7.29 \times 10^{-5}$ |
| U67122 | anti-apoptosis | UBL1 | 20 | 18 | 0.00 | $7.29 \times 10^{-5}$ |
| U38846 | chaperon | CCT4 | 20 | 18 | 0.00 | $1.26 \times 10^{-4}$ |
| U80040 | metabolism | ACO2 | 20 | 18 | 0.00 | $8.38 \times 10^{-5}$ |
| U86782 | proteasome | POH† | 20 | 18 | 0.00 | $5.90 \times 10^{-5}$ |
| X57152 | signaling | CSNK2B | 20 | 18 | 0.00 | $7.29 \times 10^{-5}$ |
| D87446 | unknown | KIAA0257 | 20 | 18 | 0.00 | $1.26 \times 10^{-5}$ |

Accession numbers are GENBANK ® genetic sequence database numbers.
†symbol not HUGO approved.
‡Wilcoxon rank sum test.

because many of the top 50 EDG-MM showed no variability across MM and thus could not be used to distinguish MM subgroups. A similar clustering strategy was employed to cluster the samples using the 50 LDG-MM1 and 50 LDG-MM2.

The MM samples clustering with the tonsil B cell samples were then identified to determine whether the MM cases clustering with tonsil B cells, or tonsil and bone marrow plasma cells could be correlated with gene expression-defined MM subgroups (Table 4). This data showed that of the MM cases clustering tightly with the tonsil B cell samples, 13 of 22 were from the MM4 subgroup, accounting for a majority of all MM4 cases (13 of 18 MM4 samples). The LDG-MM defined cluster distribution of gene expression-defined MM subgroups was dramatically different in that 14 of the 28 MM samples clustering with the tonsil plasma cell samples were from MM3 subgroup (14 of 15 MM3 samples). LDG-MM2 again showed a strong correlation with the MM subgroups in that 14 of the 20 MM cases in this cluster were from the MM2 subgroup (14 of 21 MM2 cases). Thus, the MM4, MM3, and MM2 subtypes of MM have similarities to tonsil B cells, tonsil plasma cells, and bone marrow plasma cells respectively. MM1 represented the only subgroup with no strong correlations with normal cell counterparts tested here, suggesting that this class has unique characteristics yet to be uncovered.

The distribution of the four MM subgroups in the normal cell cluster groups was determined next (Table 5). The results demonstrate that whereas all MM3 cases were able to be classified, 6 MM1, 5 MM2, and 3 MM4 cases were not clustered with any normal cell group in any of the three cluster analyses. In all samples capable of being clustered, there were strong correlations between gene expression-defined subgroups and normal cell types with the exception of MM1. The data also show that 3 MM1, 2 MM2, 4 MM3, and 1 MM4 cases were found to cluster in two groups. No samples were found in three groups and all cases clustering with two normal classes were always in an adjacent, temporally appropriate groups. P241 was an exception in that it was clustered in the bone marrow plasma cell and tonsil B cell groups.

Figure 5:
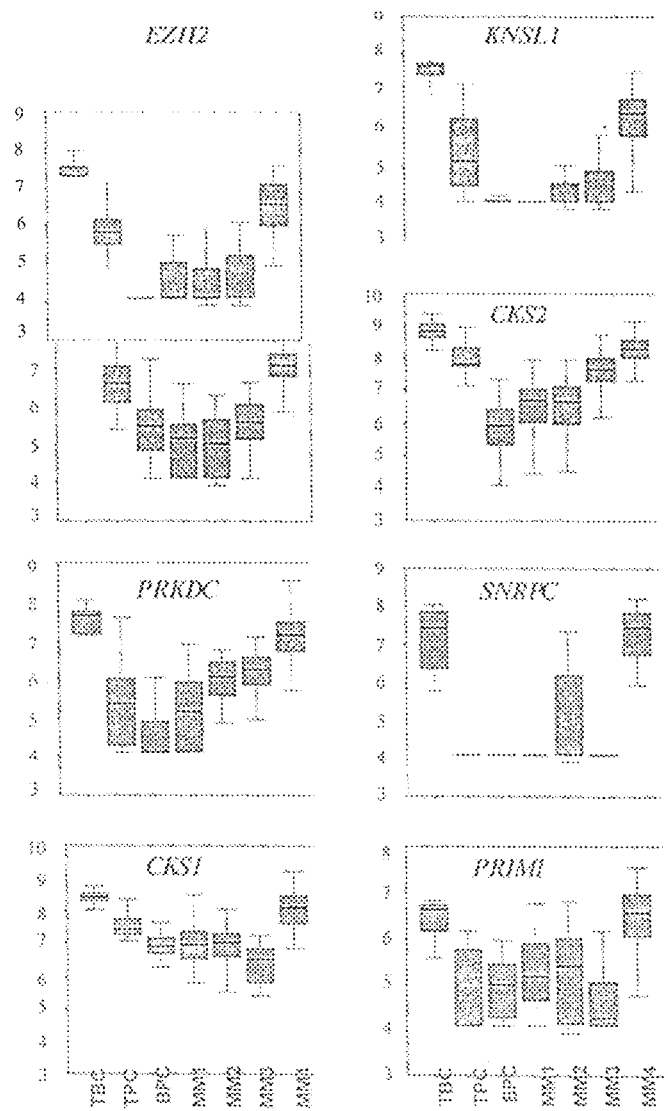
FIG. 5 shows variation in expression of proliferation genes reveals similarities between tonsil B cells and MM4. The data are shown as boxplot of Kruskal-Wallis test values. The seven groups analyzed (tonsil B cells, tonsil plasma cells, bone marrow plasma cells, and gene expression defined subgroups MM1, MM2, MM3, and MM4) are distributed along the x-axis and the natural log transformed average difference is plotted on the y axis. EZH2; $p=7.61\times10^{-11}$; KNSL1, $p=3.21\times10^{-8}$; PRKDC, $p=2.86\times10^{-11}$; SNRPC, $p=5.44\times10^{-12}$; CCNB1, $p=2.54\times10^{-8}$; CKS2, $p=9.49\times10^{-11}$; CKS1, $p=5.86\times10^{-9}$; PRIM1, $p=4.25\times10^{-5}$.

Because one of the EDG-MMs was discovered to be cyclin B1 (CCNB1), it was determined if a panel of proliferation association genes recently discovered to be up-regulated in MM4 could be used to advance and validate the classification of MM4 as a so-called tonsil B cell-like form of MM. Box plots of the expression patterns of CCNB1, CKS1, CKS2, SNRPC, EZH2, KNSL1, PRKDC, and PRIM1 showed significant differences across all the groups tested with strong significant correlation between tonsil B cells and MM4 (FIG. 5). Several important observations were made in this analysis. For all the genes, with the exception of SNRPC, there was a progressive reduction in expression in the transition from tonsil B cells to tonsil plasma cells to bone marrow plasma cells. In addition, striking correlations were observed with PRIM1 (FIG. 5). Although PRIM1 expression was significantly different across the entire group ($p=4.25\times10^{-5}$), no difference exists between tonsil B cells and MM4 (Wilcoxon rank sum [WRS] p=0.1), or between tonsil plasma cells and MM3 (WRS p=0.6). Given the important function of several transcription factors in driving and/or maintaining plasma cell differentiation, it was determined if these factors showed altered expression across the groups under study. Although other factors showed no significant changes, XBP1 (FIG. 5) showed an enormous up-regulation between tonsil B cells and tonsil plasma cells as expected. However, the gene showed a reduction in bone marrow plasma cells and a progressive loss across the four MM subgroups with MM4 showing the lowest level ($p=3.85\times10^{-10}$).

Based on conventional morphological features, plasma cells have been thought to represent a homogeneous end-stage cell type. However, phenotypic analysis and gene expression profiling disclosed herein demonstrated that plasma cells isolated from distinct organs can be recognized as belonging to distinct stages of development. Multiple myeloma plasma cells are derived from the bone marrow and are thought to represent a transformed counterpart of normal terminally differentiated bone marrow plasma cells. However, the dramatic differences in survival, which can range from several months to greater than 10 years, suggests that multiple myeloma may represent a constellation of several subtypes of disease. Conventional laboratory parameters have not been particular useful in segregating distinct disease subtypes with sufficient robustness that would allow adequate risk stratification. In addition, unlike achievements in classifying leukemias and lymphomas based on similar nonrandom recurrent chromosomal translocations, the extreme karyotypic heterogeneity of multiple myeloma has made attempts at understanding the molecular mechanisms of the disease and classification prediction virtually impossible.

In studies presented here, it was identified that many EDGs and LDGs exhibit highly variable expression in multiple myeloma, suggesting that multiple myeloma might be amenable to a developmental stage-based classification. It appears from the results of this study that multiple myeloma can in fact be classified based on similarities in gene expression with cells representing distinct stages of B cell differentiation. This developmental based-system in conjunction with the gene expression-based system reported above represents a critical affirmation of the validity of the developmental-based system.

Recent studies provide support for the hypothesis that MM3 represents a tonsil plasma cell-like form of the disease. Microarray profiling with the U95Av2 GENECHIP® microarray on 150 newly diagnosed patients (including the 74 described here) along with an analysis of chromosome 13 loss has revealed a significant link between reduced RB1 transcripts with either monosomy or partial deletions of chromosome 13 (unpublished data). In these studies, it was observed that a number of multiple myeloma cases with or without chromosome 13 deletion had RB1 transcripts at levels comparable to those seen in normal tonsil plasma cells. FISH analysis with a bacterial artificial chromosome BAC covering RB1 demonstrated that these cases did not have interstitial deletions of the RB1 locus. Given that RB1 was found to be a LDG-MM1, it was determined if the low levels of RB1 may be linked to tonsil plasma cell-like MM, i.e MM3. Of 35 multiple myeloma cases with RB1 AD values of <1100 (RB1 AD value not less than 1100 in 35 normal bone marrow plasma cell samples tested), 74% belonged to the MM3 class. In contrast, of 38 multiple myeloma cases lacking deletion 13 and having RB1 AD values greater than 1100, only 21% belonged to the MM3 subtype.

Although there is a significant link between the cell development-based classification and gene expression profiling-based classification disclosed herein, there are exceptions in that although as expected the majority of the MM4 cases belonged to the tonsil B cell-cluster subgroup, 5 MM3, 1 MM2, and 3 MM1 cases were also found in this cluster. The recognition that cases within one gene expression-defined subgroup could be classified in two normal cell defined clusters suggests these cases may have intermediate characteristics with distinct clinical outcomes. It is of interest to determine if the unsupervised gene expression-based system or developmental stage-based system alone or in combination will allow the creation of robust risk stratification system. This can be tested by allowing sufficient follow-up time on >150 uniformly treated multiple myeloma cases in which profiling has been performed at diagnosis.

MM1 was the only gene expression-defined subgroup lacking strong similarities to any of the normal cell types analyzed in this study. It is possible that MM1 has similarities to either mucosal-derived plasma cells or peripheral blood plasma cells which has recently been shown to represent a distinct type of plasma cells. Future studies will be aimed at providing a developmental stage position for this subtype.

The hypoproliferative nature of multiple myeloma, with labeling indexes in the clonal plasma cells rarely exceeding 1%, has lead to the hypothesis that multiple myeloma is a tumor arising from a transformed and proliferative precursor cell that differentiates to terminally differentiated plasma cells. It has been shown that there is a bone marrow B cell population transcribing multiple myeloma plasma cell-derived VDJ joined to IgM sequence in IgG- and IgA-secreting multiple myelomas. Other investigations have shown that the clonogenic cell in multiple myeloma originates from a pre-switched but somatically mutated B cell that lacks intraclonal variation. This hypothesis is supported by recent use of single-cell and in situ reverse transcriptase-polymerase chain reaction to detect a high frequency of circulating B cells that share clonotypic Ig heavy-chain VDJ rearrangements with multiple myeloma plasma cells. Studies have also implicated these precursor cells in mediating spread of disease and affecting patient survival.

Links of gene expression patterns between subsets of multiple myeloma and cells representing different late stages of B cell differentiation further support the above hypothesis in that MM4 and MM3 may have origins in a so called "multiple myeloma stem cell". This hypothesis can be tested by isolating B cells from tonsils or lymph nodes or peripheral blood of MM3 and MM4 patients, differentiating them into plasma cells in vitro using a new method described by Tarte et al. (2002) and then testing for the presence of an multiple myeloma gene expression signature within the differentiated populations. Even if the multiple myeloma stem cell represents a minority population in the B cells, the multiple myeloma gene expression signature may be recognized, if not with conventional microarray, then by more sensitive quantitative real-time. A real time RT-PCR method is envisioned as expression profile models using at little as 20 genes that distinguish malignant multiple myeloma plasma cells from normal plasma cells at an accuracy of 99.5% have been developed.

Regardless of the outcome of these experiments, it is clear that gene expression profiling has become an extremely powerful tool in evaluating the molecular mechanisms of plasma cell differentiation and how these events relate to multiple myeloma development and progression, which in turn should provide more rational means of treating this currently fatal disease.

TABLE 4

Distribution of Multiple Myeloma Subgroups in Hierarchical Clusters Defined by EDG-MM, LDG-MM1, and LDG-MM2 Genes

| Normal Cell-Define Cluster | Gene Expression-Defined MM Subgroups | | | | p |
| --- | --- | --- | --- | --- | --- |
| | MM1 (n = 20) | MM2 (n = 21) | MM3 (n = 15) | MM4 (n = 18) | |
| EDG-MM (n = 22) | 3 | 1 | 5 | 13 | .00005 |
| LDG-MM1 (n = 29) | 8 | 4 | 14 | 3 | .000008 |
| LDG-MM2 (n = 20) | 6 | 14 | 0 | 0 | .000001 |

TABLE 5

Distribution of Gene Expression-Defined Multiple Myeloma Subgroup Cases in Normal Cell Clusters defined by EDG-MM, LDG-MM1, and LDG-MM2

| MM1 | TBC | TPC | BPC | MM2 | TBC | TPC | BPC | MM3 | TBC | TPC | BPC | MM4 | TBC | TPC | BPC |
| --- | --- | --- | --- | --- | --- | --- | --- | --- | --- | --- | --- | --- | --- | --- | --- |
| P026 | | Y | Y | P237 | | Y | Y | P052 | Y | Y | | P034 | Y | Y | |
| P037 | | Y | Y | P241 | Y | | Y | P098 | Y | Y | | P051 | Y | | |
| P029 | Y | Y | | P079 | | | Y | P107 | Y | Y | | P057 | Y | | |
| P061 | | Y | | P083 | | | Y | P158 | Y | Y | | P063 | Y | | |
| P066 | | Y | | P121 | | | Y | P119 | | Y | | P065 | Y | | |
| P006 | | Y | | P144 | | | Y | P221 | | Y | | P075 | Y | | |
| P120 | | Y | | P157 | | | Y | P030 | | Y | | P084 | Y | | |
| P131 | | Y | | P171 | | | Y | P043 | | Y | | P122 | Y | | |
| P002 | | | Y | P176 | | | Y | P053 | | Y | | P127 | Y | | |
| P010 | | | Y | P213 | | | Y | P055 | | Y | | P154 | Y | | |
| P067 | | | Y | P215 | | | Y | P138 | | Y | | P187 | Y | | |
| P226 | | | Y | P251 | | | Y | P155 | | Y | | P199 | Y | | |
| P025 | Y | | | P250 | | | Y | P163 | | Y | | P255 | Y | | |
| P082 | Y | | | P222 | | Y | | P239 | | Y | | P054 | | Y | |
| *P085* | | | | P103 | Y | | | P175 | Y | | | P101 | | Y | |
| *P099* | | | | P202 | Y | | | | | | | P056 | | | |
| *P001* | | | | P015 | | | | | | | | *P091* | | | |
| *P016* | | | | P048 | | | | | | | | *P168* | | | |
| *P036* | | | | P124 | | | | | | | | | | | |
| *P118* | | | | P212 | | | | | | | | | | | |
| | | | | P249 | | | | | | | | | | | |

MM1, MM2, MM3, MM4, and PXXX represent gene expression-defined subgroups and patient identifiers, respectively.
Y indicates that the case was found in the normal cell-defined cluster.
Cases in italics were not found to cluster with any normal cell type. Some cases were found to cluster with two normal cell types.
TBC, tonsil B cells;
TPB, tonsil plasma cells;
BPC, bone marrow plasma cells.

Example 9

Gene Expression Profiling to Identify Genes that could be Useful as Diagnostic, Prognostic and Potential Targets in Myeloma Global gene expression profiling identified genes directly involved in pathogenesis and classification of myleoma. Next, this profiling was used to identify genes whose abnormal expression may cause an aggressive phenotype of myeloma. (a) Subjects: 668 newly diagnosed patients with symptomatic or progressive multiple myeloma, which included 2 cycles of blood stem cell-supported high-dose melphalan (200 mg/m$^2$) were enrolled in this study. A subset of 575 patients with available genetic measurements constituted sample for this analysis. Their median follow-up was 30 months. There were 185 progression or death vents and 128 deaths. Patient characteristic were as follows: 20% were 65 years or older, 31% had beta-2-microglobulin levels>=4 mg/L, 55% had C-reactive protein levels>=4 mg/L; 22% presented with hemoglobin values <=10 g/dL, 10% with creatinine values >=2 mg/dL; LDH was elevated (>=190IU/L) in 15%; cytogenetic abnormalities were detected in 33%.

(b) Gene Expression Profiling: Gene expression profiling was performed using U133Plus2.0 oligonucleotide microarrays as described (Tian, et al., 2003) for a consecutive 351 patient subset. The expression value 'Signal' for each probe set was derived from the MAS5.01 software (Affymetrix, Santa Clara, Calif.). Median follow-up for survival in this subset was 22 months and there were 98 events and 64 deaths.

(c) Fluorescence In Situ Hybridization: Bacterial artificial chromosomes specific for CKS1B at 1q21 (RP11-307C12) and ASPM (RP11-32D17) at 1q31 were purchased from BAC/PAC Resources (Oakland, Calif.) and directly labeled with Spectrum green or Spectrum red (Vysis Inc, Downers Grove, Ill.). Metaphase fluorescence in situ hybridization was performed as previously described (Sawyer et al., 2005). The probes were confirmed to map to the 1q21 and 1q31 bands using metaphase spreads from normal human lymphocytes. Triple color interphase fluorescence in situ hybridization analyses of chromosomes 13 (RB) and 1q21 (CKS1B) copy number (Shaughnessy et al., 2000) were performed in a subset of 421 patients (145 events and 100 deaths, follow-up of 31 months); deletion 13q was scored positive when >=80% of clonal cells exhibited loss of a signal at 13q14 as described previously (McCoy et al., 2003). Of these 421 patients, 197 were among those with microarrays and 224 were not.

(d) Western Blotting: Nuclear protein was isolated from an aliquot of CD138 enriched plasma cells that were also analyzed by microarray. Western Blotting was carried out using the WestemBreeze® Chemiluminiscent Immunodetection protocol as described (Invitrogen, Carlsbad, Calif.). The antibodies to CKS1B and phospo-thr-187-p27$^{Kip1}$ were purchased from Zymed laboratories Inc., (South San Francisco, Calif.) and anti-Histone 1A was purchased from Upstate Biotechnology (Charlottesville, Va.).

(e) Statistical Analysis: False discovery rates methods (Storey and Tibshirani, 2003) were used to adjust for multiple comparisons of the Affymetrix probe set Signals for the 351 microarrays. For each Affymetrix Signal, log rank tests for the equality of disease-related survival distributions were performed separately for quartile 1 vs quartiles 2 through 4 (to identify under-expressed genes) and quartile 4 vs quartiles 1 through 3 (to identify over-expressed genes). A false discovery rate cut-off of 2.5% was applied to each list and a total of 70 probe sets were retained. Extreme quartile membership (Q1 or Q4) was associated with a higher incidence of disease-related death in all retained probe sets. All other EFS and survival outcomes in this analysis were overall (i.e. not disease-related). The Kaplan-Meier method was used to estimate event-free and overall survival distributions and log rank tests were used to test for their equality across groups. Chi-square tests and Fisher's exact test were used to test for the independence of categories. Proportional hazards regression was used to compare the effect of CKS1B amplification to other variables and the proportions of observed heterogeneity (i.e. $R^2$) were computed (O'Quigley and Xu, 2001). The statistical packages R version 2.0 (R Development Core Team, 2004) and SPLUS 6.1 (Insightful Corp., 2002) were used for this analysis.

(f) Definition of Genetic Subgroups: Nearly 50% of the newly diagnosed myelomas contain one of five recurrent chromosomal translocations that result in the hyperactivation of MAF, MAFB, FGFR3/MMSET, CCND3, CCND1 (Kuehl, W. M. et al., 2002) with divergent prognoses (Fonseca, R. et al., 2004), detectable as "spiked" expression by microarray analysis (Zhan, F. et al., 2003). Genetic subgroups were classified within the context of metaphase cytogentics as having normal karyotypes (originating in normal hematopoetic cells in case of hypoproliferative myeloma) or as having hyperdiploid, hypodiploid or "other" cytogenetic abnormalities. "Other" is defined as an abnormal metaphase karyotype, i.e. structural and/or numeric changes, with a diploid modal chromosome number. Thus, non-translocation entities were defined by metaphase rather than interphase cytogenetics.

(g) Fluorescence In Situ Hybridization-based "CKS1B Amplification Index": A conventional, laboratory defined cutoff of 20% for the proportion of clonal plasma cells with 3 signals or >=4 signals was used for tests of association between expression and amplification (FIG. 2B and Table 3) and for validation of the association between amplification and overall survival (FIGS. 2C-D). Hypothesizing that 2 or more extra copies would confer additional risk compared to 1 extra copy, the multivariate analysis of overall survival (Table 5A) estimated separate effect sizes for the 3 signal proportion and the >=4 signal proportion. The index was defined as a weighted sum:(0.34*% 3 copies+0.66*%>=4 copies)/0.66, where the weights were the log-scale hazard ratio estimates for the two percentages, scaled to the effect of a unit increase in the proportion with >=4 signals. The estimated log-scale hazard ratio corresponding to a ne unit difference in the proportion with >=4 signals is nearly twice as large as that for 3 signals (i.e. 0.66/0.34=1.94). The index is 0 for patients with <=2signals in 100% f clonal cells and 100 for patients with >=4 signals in 100% of clonal cells. The full range was observed in these patients. A cut-off for the index of >=46 minimized the unadjusted log rank P-value for survival in the 421 patient subset, however, all cutoffs between 3 and 88 had P<0.003.

Example 10

Results of Global Gene Profiling

To define de novo high-risk multiple myeloma, the gene expression profiles in purified myeloma plasma cells were correlated with disease-related and overall survival in 351 newly diagnosed patients treated with 2 cycles of high-dose mephalan. Using log rank tests, 70 genes were identified for which fourth or first quartile membership was correlated with a high incidence of disease-related death (Table 6).

TABLE 6A

Quartile 4FDR 2.5% gene probe sets-rank correlations
with 1q21 amplification index, CKS1B and PC labeling
index and adjusted P-values for associations with overall survival

| Rank (Q4) | Chromosome | Probe set | Symbol | CKS1B Amplification Index r[†] | CKS1B r[‡] | PCLI r[*] | Adjusted Survival P-value[a] |
|---|---|---|---|---|---|---|---|
| 1 | 8q21.13 | 202345_s_at | NA | 0.20 | 0.22 | | 0.001 |
| 2 | Xp22.2-p22.1 | 1555864_s_at | NA | 0.34 | 0.47 | | 0.007 |
| 3 | 5p15.33 | 204033_at | TRIP13 | 0.19 | 0.45 | 0.20 | 0.001 |
| 4 | 1q22 | 206513_at | AIM2 | 0.15 | 0.13 | | 0.089 |
| 5 | 2p24.1 | 1555274_a_at | SELI | 0.28 | 0.31 | | 0.001 |
| 6 | 21q22.3 | 211576_s_at | SLC19A1 | 0.17 | 0.23 | | 0.007 |
| 7 | 3p21.3 | 204016_at | LARS2 | −0.18 | | | 0.002 |
| 8 | 1q43 | 1565951_s_at | OPN3 | 0.36 | 0.36 | | 0.007 |
| 9 | 1q31 | 219918_s_at | ASPM | 0.36 | 0.64 | 0.17 | 0.010 |
| 10 | 12q15 | 201947_s_at | CCT2 | 0.23 | 0.43 | 0.13 | 0.004 |
| 11 | 16p13.3 | 213535_s_at | UBE2I | | 0.38 | | 0.022 |
| 12 | 20q13.2-q13.3 | 204092_s_at | STK6 | 0.31 | 0.51 | 0.19 | 0.044 |
| 13 | 1p36.33-p36.21 | 213607_x_at | FLJ13052 | | | | 0.150 |
| 14 | xq12-q13 | 208117_s_at | FLJ12525 | | 0.34 | | 0.006 |
| 15 | 17q25 | 210334_x_at | BIRC5 | 0.20 | 0.36 | 0.14 | 0.110 |
| 16 | 3q27 | 204023_at | NA | 0.29 | 0.62 | 0.16 | 0.072 |
| 17 | 1q21.2 | 201897_s_at | CKS1B | 0.50 | 1.00 | 0.15 | 0.007 |
| 18 | 19q13.11-q13.12 | 216194_s_at | CKAP1 | 0.24 | 0.38 | | 0.001 |
| 19 | 1q21 | 225834_at | MGC57827 | 0.39 | 0.66 | 0.23 | 0.140 |
| 20 | 19q13.12 | 238952_x_at | DKFZp779O175 | | 0.11 | | 0.009 |
| 21 | 17p13.3 | 200634_at | PFN1 | 0.30 | 0.41 | | 0.002 |
| 22 | 19p13.2 | 208931_s_at | ILF3 | 0.22 | 0.22 | | 0.220 |
| 23 | 1q22 | 206332_s_at | IFI16 | 0.30 | 0.32 | 0.13 | 0.003 |
| 24 | 7p14-p13 | 220789_s_at | TBRG4 | | 0.13 | 0.17 | 0.009 |
| 25 | 10p11.23 | 218947_s_at | PAPD1 | 0.31 | 0.30 | | 0.150 |
| 26 | 8q24 | 213310_at | EIF2C2 | 0.28 | 0.37 | | 0.031 |
| 27 | 3q12.1 | 224523_s_at | MGC4308 | 0.17 | 0.24 | 0.14 | 0.038 |
| 28 | 1p36.3-p36.2 | 201231_s_at | ENO1 | | 0.23 | | <0.001 |
| 29 | 18q12.1 | 217901_at | DSG2 | 0.15 | | | 0.005 |
| 30 | 6q22 | 226936_at | NA | 0.15 | 0.52 | 0.17 | 0.027 |
| 31 | 8q24.3 | 58696_at | EXOSC4 | | 0.20 | | 0.330 |
| 32 | 1q21-q25 | 200916_at | TAGLN2 | 0.47 | 0.52 | | 0.120 |
| 33 | 3q21 | 201614_s_at | RUVBL1 | 0.16 | 0.14 | | 0.023 |
| 34 | 16q22-q24 | 200966_x_at | ALDOA | 0.21 | 0.28 | | 0.001 |
| 35 | 2p25.1 | 225082_at | CPSF3 | | 0.39 | | 0.073 |
| 36 | 1q43 | 242488_at | NA | 0.18 | 0.27 | 0.14 | 0.090 |
| 37 | 3q12.3 | 243011_at | MGC15606 | | 0.27 | | 0.004 |
| 38 | 22q13.1 | 201105_at | LGALS1 | | 0.31 | | 0.051 |
| 39 | 3p25-p24 | 224200_s_at | RAD18 | 0.17 | 0.41 | 0.14 | 0.040 |
| 40 | 20p11 | 222417_s_at | SNX5 | | | | 0.085 |
| 41 | 1q21.2 | 210460_s_at | PSMD4 | 0.58 | 0.59 | 0.13 | 0.067 |
| 42 | 12q24.3 | 200750_s_at | RAN | 0.22 | 0.40 | | 0.056 |
| 43 | 1pter-q31.3 | 206364_at | KIF14 | 0.41 | 0.57 | 0.25 | 0.019 |
| 44 | 7p15.2 | 201091_s_at | CBX3 | 0.14 | 0.20 | 0.16 | 0.150 |
| 45 | 12q22 | 203432_at | TMPO | 0.32 | 0.59 | 0.18 | 0.007 |
| 46 | 17q24.2 | 221970_s_at | DKFZP586L0724 | 0.27 | 0.47 | | 0.081 |
| 47 | 11p15.3-p15.1 | 212533_at | WEE1 | 0.20 | 0.54 | 0.13 | 0.056 |
| 48 | 3p12 | 213194_at | ROBO1 | | | | 0.150 |
| 49 | 5q32-q33.1 | 244686_at | TCOF1 | | | | 0.120 |
| 50 | 8q23.1 | 200638_s_at | YWHAZ | 0.26 | 0.23 | | 0.012 |
| 51 | 10q23.31 | 205235_s_at | MPHOSPH1 | | 0.40 | 0.16 | 0.050 |

[†]Correlation between gene expression signal and the CKS1B amplification index (N = 197, all patients with both GEP and FISH 1q21. Blank cells correspond to insignificant correlations (nominal P > 0.05, no multiple comparisons adjustment).
[‡]Correlation between each gene's log-scale expression and CKS1B log-scale expression. Rows with CKS1B |r| >= 0.4 are formatted bold.
[*]Correlation between each gene's log-scale expression and the PCLI.

[a]PH regression of overall survival on quartile 1 expression for each gene, adjusted for FISH 13 80% cytogenetic abnormalities, B2M > 4, CRP > 4, ALB < 3.5 and PCLI (N = 277, 74 patients are missing at least one measurement, 17 are missing FISH13, 4 are missing CA, 10 are missing one of B2M, CRP and ALB and 46 are missing PCLI: P = 0.51 for a log rank test of the effect of exclusion due to missing measurements). These P-values are not adjusted for the quartile 1 log rank significance testing that determined the ranks in column 1.

TABLE 6B

Quartile 1 gene probe sets satisfying FDR 2.5% cutoff

| Rank (Q1) | Chromosome | Probe set | Symbol | CKS1B Amplification Index $r^\dagger$ | CKS1B $r^\ddagger$ | PCLI $r^*$ | Adjusted Survival P-value$^a$ |
|---|---|---|---|---|---|---|---|
| 1 | 9q31.3 | 201921_at | GNG10 | −0.20 | −0.30 | | 0.600 |
| 2 | 1p13 | 227278_at | NA | | | −0.12 | 0.900 |
| 3 | Xp22.3 | 209740_s_at | PNPLA4 | | | | 0.029 |
| 4 | 20q11.21 | 227547_at | NA | −0.29 | −0.28 | −0.15 | 0.630 |
| 5 | 10q25.1 | 225582_at | KIAA1754 | −0.21 | −0.32 | | 0.003 |
| 6 | 1p13.2 | 200850_s_at | AHCYL1 | | | −0.13 | 0.019 |
| 7 | 1p13.3 | 213628_at | MCLC | −0.30 | −0.28 | −0.15 | 0.440 |
| 8 | 1p22 | 209717_at | EVI5 | −0.33 | −0.29 | −0.16 | 0.870 |
| 9 | 1p13.3 | 222495_at | AD-020 | −0.30 | −0.24 | −0.20 | 0.920 |
| 10 | 6p21.31 | 1557277_a_at | NA | | −0.11 | | 0.460 |
| 11 | 1p22.1 | 1554736_at | PARG1 | | −0.20 | −0.11 | 0.280 |
| 12 | 1p22 | 218924_s_at | CTBS | −0.16 | −0.11 | −0.13 | 0.460 |
| 13 | 9p13.2 | 226954_at | NA | −0.22 | −0.40 | | 0.090 |
| 14 | 1p34 | 202838_at | FUCA1 | −0.17 | −0.23 | | 0.066 |
| 15 | 13q14 | 230192_at | RFP2 | −0.28 | −0.18 | | 0.880 |
| 16 | 12q13.11 | 48106_at | FLJ20489 | −0.23 | −0.23 | −0.11 | 0.300 |
| 17 | 11q13.1 | 237964_at | NA | −0.16 | −0.20 | | 0.044 |
| 18 | 2p22-p21 | 202729_s_at | LTBP1 | −0.24 | −0.21 | | 0.097 |
| 19 | 1p13.1 | 212435_at | NA | −0.21 | −0.21 | −0.11 | 0.034 |

$^\dagger$Correlation between each gene's log-scale expression and the CKS1B amplification index (N = 197, all patients with both GEP and FISH 1q21). Blank cells correspond to insignificant correlations.
$^\ddagger$Correlation between each gene's log-scale expression and CKS1B log-scale expression. Rows with CKS1B |r| >= 0.4 are formatted bold.
*Correlation between each gene's log-scale expression and the PCLI. $^a$ PH regression of overall survival on Quartile 1 expression for each gene, adjusted for FISH 13 80%, cytogenetic abnormalities, B2M > 4, CRP > 4, ALB < 3.5 and PCLI (N = 277, 74 patients are missing at least one measurement, 17 are missing FISH 13, 4 are missing CA, 10 are missing one of B2M, CRP and ALB, and 46 are missing PCLI: P = 0.51 for a log rank test of the effect of exclusion due to missing measurements). These P-values are not adjusted for the quartile 1 log rank significance testing that determined the ranks in column 1.

Although 10% of the genes on the microarray were derived from chromosome 1, 30% of the retained genes were derived from chromosome 1, 30% of the retained genes were derived from this chromosome (P<0.0001) with 12 of 51 quartile 4 genes (23.5%) mapped to chromosome 1q and 9 of 19 quartile 1 genes (47%) mapped to chromosome 1p (Table 7).

TABLE 7

Chromosome Distribution of 2.5% FDR Probe Sets

| | U133Plus2.0 | | Q1 | | Q4 | Combined | | | |
|---|---|---|---|---|---|---|---|---|---|
| Chromosome | No. of Genes | % | No. of Genes | % | No. of Genes | Chromosome | No. of Genes | % | No. of Genes |
| 1 | 3,659 | 9.9 | 9 | 47.4 | 12 | 1 | 3,659 | 9.9 | 9 |
| 2 | 2,522 | 6.9 | 1 | 5.3 | 2 | 2 | 2,522 | 6.9 | 1 |
| 3 | 2,116 | 5.8 | 0 | 0.0 | 7 | 3 | 2,116 | 5.8 | 0 |
| 4 | 1,456 | 4.0 | 0 | 0.0 | 0 | 4 | 1,456 | 4.0 | 0 |
| 5 | 1,718 | 4.7 | 0 | 0.0 | 2 | 5 | 1,718 | 4.7 | 0 |
| 6 | 2,005 | 5.4 | 1 | 5.3 | 1 | 6 | 2,005 | 5.4 | 1 |
| 7 | 1,798 | 4.9 | 0 | 0.0 | 2 | 7 | 1,798 | 4.9 | 0 |
| 8 | 1,311 | 3.6 | 0 | 0.0 | 4 | 8 | 1,311 | 3.6 | 0 |
| 9 | 1,463 | 4.0 | 2 | 10.5 | 0 | 9 | 1,463 | 4.0 | 2 |
| 10 | 1,444 | 3.9 | 1 | 5.3 | 2 | 10 | 1,444 | 3.9 | 1 |
| 11 | 2,069 | 5.6 | 1 | 5.3 | 1 | 11 | 2,069 | 5.6 | 1 |
| 12 | 1,927 | 5.2 | 1 | 5.3 | 3 | 12 | 1,927 | 5.2 | 1 |
| 13 | 730 | 2.0 | 1 | 5.3 | 0 | 13 | 730 | 2.0 | 1 |
| 14 | 1,195 | 3.2 | 0 | 0.0 | 0 | 14 | 1,195 | 3.2 | 0 |
| 15 | 1,152 | 3.1 | 0 | 0.0 | 0 | 15 | 1,152 | 3.1 | 0 |
| 16 | 1,507 | 4.1 | 0 | 0.0 | 2 | 16 | 1,507 | 4.1 | 0 |
| 17 | 2,115 | 5.7 | 0 | 0.0 | 3 | 17 | 2,115 | 5.7 | 0 |
| 18 | 582 | 1.6 | 0 | 0.0 | 1 | 18 | 582 | 1.6 | 0 |
| 19 | 2,222 | 6.0 | 0 | 0.0 | 3 | 19 | 2,222 | 6.0 | 0 |
| 20 | 1,072 | 2.9 | 1 | 5.3 | 2 | 20 | 1,072 | 2.9 | 1 |
| 21 | 468 | 1.3 | 0 | 0.0 | 1 | 21 | 468 | 1.3 | 0 |

TABLE 7-continued

Chromosome Distribution of 2.5% FDR Probe Sets

| Chromosome | U133Plus2.0 No. of Genes | % | Q1 No. of Genes | % | Q4 No. of Genes | Combined Chromosome | No. of Genes | % | No. of Genes |
|---|---|---|---|---|---|---|---|---|---|
| 22 | 906 | 2.5 | 0 | 0.0 | 1 | 22 | 906 | 2.5 | 0 |
| X | 1,273 | 3.5 | 1 | 5.3 | 2 | X | 1,273 | 3.5 | 1 |
| Y | 80 | 0.2 | 0 | 0.0 | 0 | Y | 80 | 0.2 | 0 |
| m | 5 | 0.0 | 0 | 0.0 | 0 | m | 5 | 0.0 | 0 |
|  | 36,795 |  | 19 |  | 51 |  | 36,795 |  | 19 |
| Unknown | 17,880 |  |  |  |  | Unknown | 17,880 |  |  |
|  | 54,675 |  |  |  |  |  | 54,675 |  |  |

*An exact test for binomial proportions was used to compare the proportion of retained probe sets mapping to chromosome 1 to the proportion for the entire array.

The log-scale expression levels of proliferation-associated genes tended to have high correlations with CKS1B (Table 6). In addition, 25 of 29 (86%) genes, significantly correlated with the plasma cell labeling index, were strongly correlated with CKS1B, suggesting that this gene participated in a proliferation signaling network in patients with high risk disease. CKS1B is an independent predictor of overall survival after adjustment for chromosome 13 deletion, cytogenetic abnormalities, clinical prognostic factors and labeling index (P=0.007, Table 6, last column, row 17). Adjusted P-values are provided for other 69 genes for comparison and it is evident that few other chromosome 1 genes are both strong independent predictors of survival, proliferation and CKS1B gene amplification.

Since amplification of 1q21 was associated with myeloma progression (Shaughnessy et al., 2000), the over-representation of 1q genes among the list of 70 justified a focus on this region in search for a molecular basis of high-risk myeloma; 4 genes (TAGNL2, PSMD4, MGC57827, CKS1B) map to 1q21, among which CKS1B quartile 4 membership was most strongly associated with survival in unadjusted log rank tests (i.e. according to the list order of Table 6).

DNA synthesis is mediated by the action of the cyclin E/CDK2 complex, which is in turn negatively regulated by the cyclin-dependent kinase inhibitor p27Kip1 (Sherr, et al., 1999). The small evolutionarily conserved protein CKS1 is required for SCFSkp2-mediated ubiquitinylation and proteasomal degradation of cyclin-dependent kinase inhibitor p27Kip1 (Ganoth, et al., 2001;Spruck, et al., 2001). p27Kip1 degradation not only permits DNA replication but also ensures the correct progression of cells through S phase into mitosis (Nakayama, et al., 2004) and Cks proteins interact with the proteasome to control the proteolysis of mitotic cyclins by way of regulating the transcriptional activity of CDC20 (Morris, et al., 2003), a regulatory subunit of the anaphase-promoting complex/cyclosome ubiquitin ligase (Peters, 2002). Thus, CKS1 and the SCFSkp2-p27Kip1-Cdk1/2 axis appear to be important for both DNA synthesis and mitosis (Pagano, 2004). The low p27Kip1 protein levels in cancer cells, in the absence of gene mutations, has prompted speculation that hyper-activation of CKS1B and/or SKP2, may account for the low levels of p27Kip1 (Slingerland and Pagano, 2000). Given its well-documented role in regulating cell cycle progression, its map location, link to myeloma cell proliferation and patient survival, CKS1B was considered a candidate gene, the inappropriate expression of which may promote an aggressive phenotype.

Figure 6A:
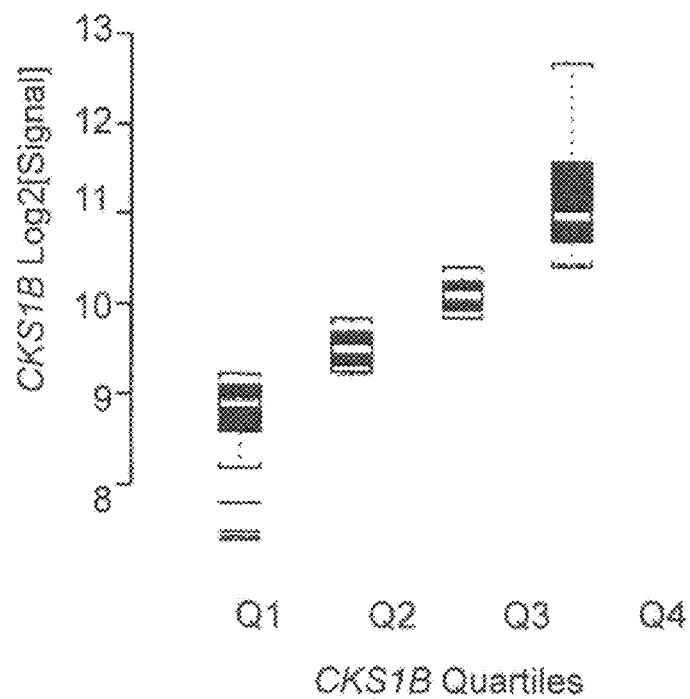
FIG. 6A-B show that CKS1B expression by myeloma plasma cells is variable and high levels define a high-risk myeloma entity.
Figure 6B:
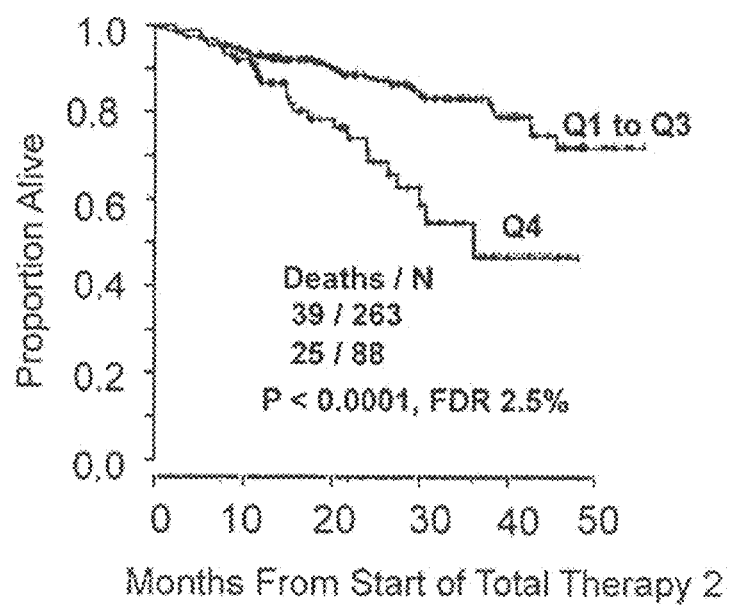

As was true for all the gene transcripts listed in Table 6, CKS1B levels were strongly correlated with clinical outcome (FIGS. 6A-B): 25 deaths had occurred among 88 patients with quartile 4 expression levels compared to only 39 among the 263 patients with quartile 1-3 levels (p<0.0001, false discovery rate, 2.5%); this was also true for event-free survival (34 of 88 in the quartile 4 cohort had experienced an event compared to 64 of 263 in the remainder; p<0.0001). Levels of SKP2, the CKS1B partner gene, were not significantly associated with survival (P=0.3).

Figure 7A:
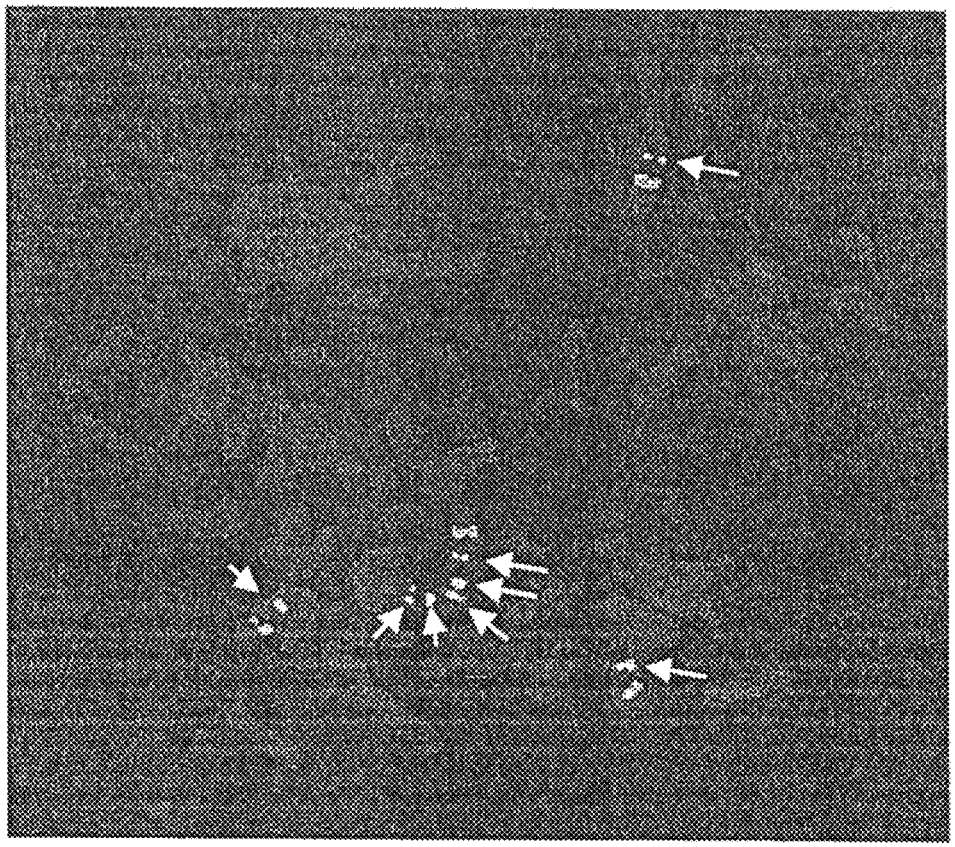

Next, whether CKS1B gene expression was linked to gene copy number was examined. Up to 8 copies of CKS1B were detected in metaphases of primary samples (FIG. 7A). Interphase fluorescence in situ hybridization analysis revealed 3 or more copies of CKS1B in 46% among 197 cases with concurrent gene expression data. Expression levels were significantly linked to CKS1B copy number (FIG. 7B). Conversely, amplification increased in frequency as CKS1B expression levels increased from quartile 1 to quartile 4 (P<0.0001, Table 8).

TABLE 8

Relationship between CKS1B gene expression quartiles and CKS1B amplification in newly diagnosed myeloma.

| CKS1B Expression[†] | # AMPLIFIED | % AMPLIFIED |
|---|---|---|
| quartile 1[‡] | 9 | 20% |
| n = 44 | | |
| quartile 2 | 12 | 28% |
| n = 43 | | |
| quartile 3 | 26 | 51% |
| n = 51 | | |
| quartile 4 | 44 | 75% |
| n = 59 | | |
| total 197 | 91 | 46% |

Figure 7C:
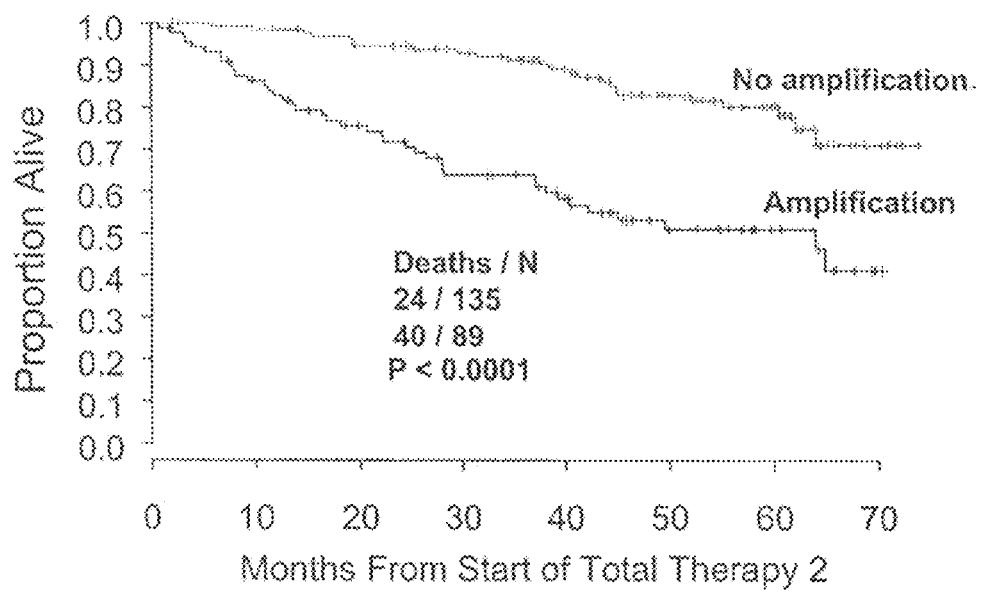
Figure 7D:
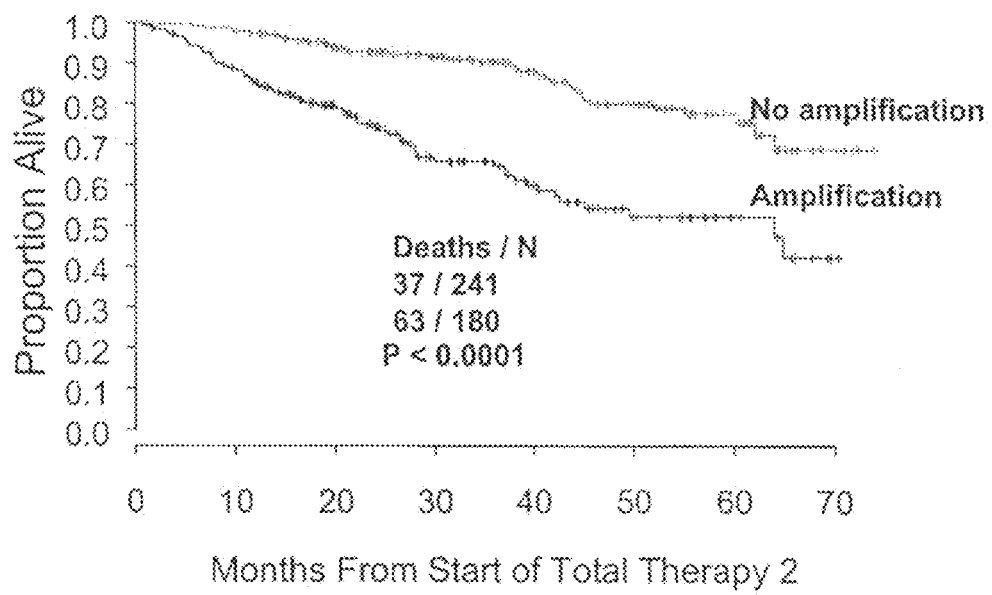

[†]P < 0.0001. Amplification is defined as >=20% of cells with 3 or >=4 CKS1B signals, for validation in conjunction with FIGS. 7c-d, as described in the Methods. Other tables use the CKS1B amplification index and its optimal cutoff.
[‡]Quartile assignments based upon 351 patients with GE Examination of CKS1B gene amplification in the context of expression levels of the 70 genes (Table 6) revealed, as expected, correlations with genes on chromosome 1q21 but, importantly, also with genes linked to cell proliferation not mapping to 1q21. The BAC clone used to evaluate CKS1B gene copy number also measured the copy number of PBXIP1 (mapping centromeric to CKS1B) and PB591, LENEP, ZFP67, FLJ32934, ADAM15 and EFNA4 (all mapping telomeric to CKS1B). In examining the relationship between gene copy number and the expression levels of these genes (Table 9), RNA expression was most strongly correlated with DNA copy number in the case of CKS1B. Importantly, none of the other genes mapping to this BAC were among the 70 linked to short survival.

TABLE 9

Relationship of quartile 4 gene expression to amplification for genes located on bacterial artificial chromosome (BAC) used to measure 1q21 amplification.

| Symbol | Not Amplified n/129 | (%) | Amplified* (Amplification. Index. >= 46) n/68 | (%) | P-Value† | Amplification Index Symbol | Log Rank N/129 |
|---|---|---|---|---|---|---|---|
| PBXIP1 | 24 | (18.6) | 28 | (41.2) | 0.0012 | PBXIP1 | 24 |
| CKS1B | 20 | (15.5) | 39 | (57.4) | <0.0001 | CKS1B | 20 |
| PB591 | 23 | (17.8) | 38 | (55.9) | <0.0001 | PB591 | 23 |
| LENEP | 31 | (24.0) | 18 | (26.5) | 0.8389 | LENEP | 31 |
| ZFP67 | 27 | (20.9) | 29 | (42.6) | 0.0023 | ZFP67 | 27 |
| FLJ32934 | 28 | (21.7) | 11 | (16.2) | 0.4606 | FLJ32934 | 28 |
| ADAM15 | 23 | (17.8) | 29 | (42.6) | 0.0003 | ADAM15 | 23 |
| EFNA4 | 26 | (20.2) | 23 | (33.8) | 0.0528 | EFNA4 | 26 |

*The 0-100 scale CKS1B amplification index is a weighted sum of the proportions of clonal cells with 3 copies of CKS1B and >=4 copies of CKS1B, defined by (.34 * % 3 copies + .66 * % >= 4 copies)/.66
†For a test of the independence of amplification and 4th quartile membership (N = 197)
‡Correlation between each gene's expression and the 0-100 scale CKS1B amplification index
ᵃLog rank test for association of Q4 membership and overall survival (N = 351, 64 deaths)

Further, the association of CKS1B over-expression with survival and event-free survival was validated in a cohort of 224 patients lacking microarray data. CKS1B amplification levels were inversely correlated with both event-free survival (P<0.0001) and overall survival (P<0.0001, FIG. 7C). These effects were also observed when all 421 patients were considered (overall survival, P<0.0001, FIG. 7D; event-free survival, P<0.0001).

Multivariate proportional hazards analyses were performed using the 369 patients with both CKS1B amplification samples and complete risk factor data (Table 10). The 3 genetic risk factors (CKS1B amplification, chromosome 13q14 deletion, metaphase karyotype abnormalities) all independently conferred both inferior event-free and overall survival, whereas hypoalbuminemia was the only one of three standard prognostic factors that retained adverse implications for both endpoints examined. Collectively, these 6 variables accounted for 46% and 33% of variability in survival and event-free survival, respectively, with the 3 standard, non-genetic parameters contributing only an additional 7.2% and 7.4%. CKS1B amplification was an independent predictor of outcome both as a 0-100 scale index and a two-group category (Tables 10A and B), after adjustments for the variables mentioned above and for the plasma cell labeling index.

TABLE 10A

Multivariate proportional hazards analysis† (n = 369)

| | % | Event-Free Survival | | | Survival | | |
|---|---|---|---|---|---|---|---|
| | | HR | P | Cumulative $r^2$ | HR | P | Cumulative $r^2$ |
| CKS1B Amplification Index (0-100) | | 1.009 | 0.002 | 0.160 | 1.011 | 0.002 | 0.219 |
| FISH Chromosome 13 Deletion | 25.5 | 1.786 | 0.006 | 0.224 | 1.879 | 0.014 | 0.308 |
| Abnormal Karyotype | 35.0 | 1.875 | 0.001 | 0.272 | 2.298 | <0.001 | 0.393 |
| Beta-2-microglobulin >= 4 mg/L | 35.8 | 1.478 | 0.046 | 0.305 | 1.396 | 0.170 | 0.422 |
| C-reactive protein >= 4 mg/L | 63.4 | 1.533 | 0.028 | 0.320 | 1.586 | 0.055 | 0.448 |
| Albumin < 3.5 g/dL | 16.5 | 1.660 | 0.019 | 0.336 | 1.698 | 0.044 | 0.461 |
| Events/Deaths | | | 127 | | | 84 | |

TABLE 10B

Multivariate proportional hazards analysis† (n = 369)

| | % | Event-Free Survival | | | Survival | | |
|---|---|---|---|---|---|---|---|
| | | HR | P | Cumulative $r^2$ | HR | P | Cumulative $r^2$ |
| CKS1B Amplification Index >= 46 | 32.5 | 1.68 | 0.008 | 0.132 | 2.12 | 0.001 | 0.207 |
| FISH Chromosome 13 Deletion | 25.5 | 1.74 | 0.010 | 0.204 | 1.83 | 0.020 | 0.293 |
| Abnormal Karyotype | 35.0 | 1.94 | <0.001 | 0.257 | 2.33 | <0.001 | 0.383 |
| Beta-2-microglobulin >= 4 mg/L | 35.8 | 1.52 | 0.033 | 0.293 | 1.43 | 0.140 | 0.417 |
| C-reactive protein >= 4 mg/L | 63.4 | 1.49 | 0.038 | 0.312 | 1.56 | 0.060 | 0.443 |
| Albumin < 3.5 g/dL | 16.5 | 1.69 | 0.016 | 0.331 | 1.73 | 0.035 | 0.455 |
| Events/Deaths | | | 127 | | | 84 | |

Paired CKS1B expression data at diagnosis and relapse, available in 32 cases, revealed increased expression in 84% at relapse (P=0.0001, FIG. 8), which was especially prominent in patients with quartile 1-3 expression levels at diagnosis. Paired CKS1B copy number data at diagnosis and relapse were available in 17 patients: of 7 lacking amplification at diagnosis, 4 acquired >=3 copies at relapse; of 10 cases with 3 copies at diagnosis, 4 had acquired >=4 copies at relapse but 2 cases with 4 or more copies at diagnosis exhibited no further amplification at relapse. These data suggested that CKS1B amplification/over-expression was also associated with disease progression.

The frequency of CKS1B quartile 4 expression varied among previously reported genetic subgroups (Table 11). With respect to gene expression-based translocations, nearly two-thirds of patients with MAF or MAFB activation, one-third each with FGFR3/MMSET and CCND1 activation, and only 18% without translocations had CKS1B hyper-activation (P<0.0001). When examined in the context of metaphase karyotypes, CKS1B quartile 4 expression was present in approximately 20% of cases with hyperdiploid or normal, i.e. uninformative, karyotypes, whereas this feature was seen in nearly 50% of patients with hypodiploid and other cytogenetic abnormalities (P=0.0002).

In a separate multivariate analysis that adjusted for genetic subgroups, CKS1B quartile 4 expression remained an independent adverse outcome predictor (Table 11); the gene expression-derived translocation category as a whole conferred inferior event-free (P=0.034) but not of overall survival (P=0.261); however, consistent with Fonseca et al., 2004), CCND1 activation impacted both endpoints favorably. While not adjusted for the multiple log rank tests that identified the 70 genes, this analysis, suggests that CKS1B expression retains explanatory power within relevant genetic subgroups.

TABLE 11A

Relationship between genetic abnormalities and CKS1B expression quartiles

| Abnormality Category[†] | n/347 (%) | CKS1B Q4 n | CKS1B Q4 (%) | P-Value* |
|---|---|---|---|---|
| Expression-derived translocation | | | | |
| t(11; 14) | 60 (17.3) | 20 | (33.3) | <0.0001 |
| t(4; 14) | 48 (13.8) | 17 | (35.4) | |
| t(14; 16) & t(14; 20) | 14 (4.0) | 9 | (64.3) | |
| No Translocation Spike | 225 (64.8) | 41 | (18.2) | |
| Metaphase karyotype | | | | |
| Hyperdiploid | 55 (15.9) | 10 | (18.2) | 0.0002 |
| Non-hyperdiploid | 48 (13.8) | 24 | (50.0) | |
| Other Cytogenetics Abnormality | 9 (2.6) | 4 | (44.4) | |
| No Cytogenetics Abnormality | 235 (67.7) | 49 | (20.9) | |

[†]Translocations were determined from the expression spikes t(11; 14) = CCND1, t(4;14) = FGFR3/MMSET, t(14; 16) = MAF and t(14; 20) = MAFB. Aneuploidy and other cytogenetic abnormalities were determined from cytogenetics, for which 4 observations were missing.
*Fisher's exact test of the independence of each category and CKS1B 4th quartile membership. Under the null hypothesis, Q4 contains on average 25% of patients within each level, corresponding to a proportional distribution across Q1-3 and Q4.

TABLE 11B

Multivariate analysis of CKS1B quartile 4 expression and cytogenetic abnormalities[†]

| | Event-Free Survival | | Survival | |
|---|---|---|---|---|
| | HR | P | HR | P |
| CKS1B Q4 | 1.97 | 0.003 | 2.16 | 0.005 |
| Expression-derived translocation | | | | |
| t(11; 14) | 0.59 | 0.034 | 0.82 | 0.261 |
| t(4; 14) | 1.67 | | 1.77 | |
| t(14; 16) & t(14; 20) | 1.48 | | 1.12 | |
| Metaphase karyotype | | | | |
| Hyperdiploid | 1.75 | 0.006 | 1.84 | 0.013 |
| Non-hyperdiploid | 2.29 | | 2.56 | |
| Other Cytogenetics Abnormality | 2.35 | | 2.71 | |
| $r^2$ | 0.218 | | 0.223 | |
| Events/Deaths | 97 | | 63 | |

[†]N = 347. Of 351 patients with expression data, 4 are missing cytogenetics.
[‡] Partial likelihood ratio test for the overall effect of the category.

Figure 8:
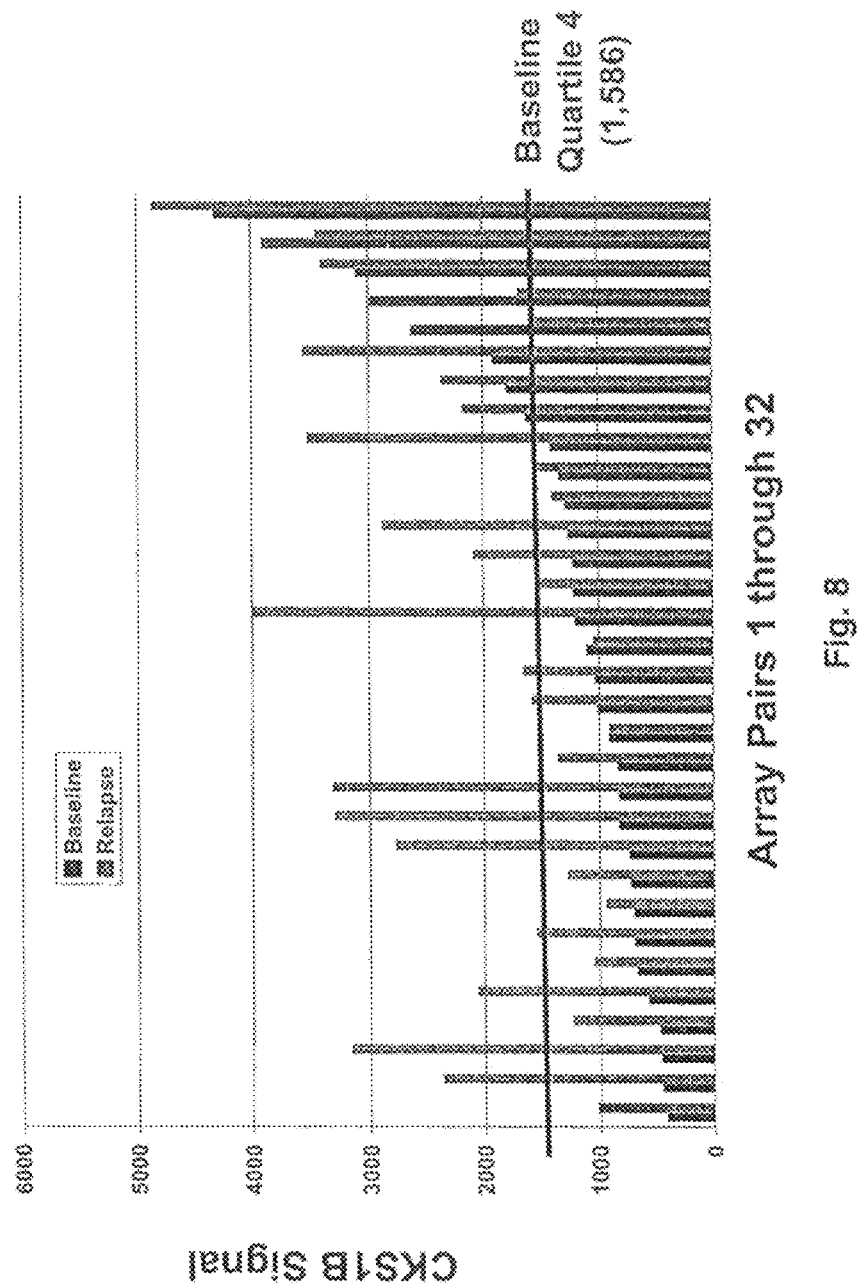
FIG. 8 shows that CKS1B expression increases in relapsed myeloma. This figure shows CKS1B signal for 32-paired diagnosis and relapse arrays. The quartile 4 reference line is taken from the complete (N=351) sample of arrays at diagnosis. A majority of samples showed increased expression at relapse and the most dramatic changes were in those with quartile1 to quartile3 expression levels at diagnosis. For a Welch-modified paired t-test was used to compare log-scale Signal at diagnosis and relapse.

Additionally, Western blot analysis of nuclear protein from plasma cells from 27 newly diagnosed myeloma cases and 7 myeloma cell lines showed a strong correlation between CKS1B mRNA and protein, but no correlation between mRNA and protein levels for $p27^{Kip1}$. However, CKS1B protein and $p27^{Kip1}$ protein levels showed an inverse correlation (FIG. 8). Cytoplasmic and non-phosphorylated-thr-187-$p27^{Kip1}$ levels were not altered in myeloma cell lysates with respect to CKS1B expression (data not shown). Levels of $p27^{Kip1}$ protein were not correlated with the mRNA levels of SKP2 (data not shown).

Example 11

The Effect of Bortezomid on Patients with Abnormal Copy Numbers of Genes Located in Chromosomes 1 and 13

Many recurrent genomic aberrations in MM have been discovered during the past two decades. In particular, the deletion of chromosome 13 and the amplification of 1q21 are associated with poor diagnosis of patient with multiple myeloma. The following example pertain to clinical results obtained from newly diagnosed multiple myeloma patients.

Figure 10:
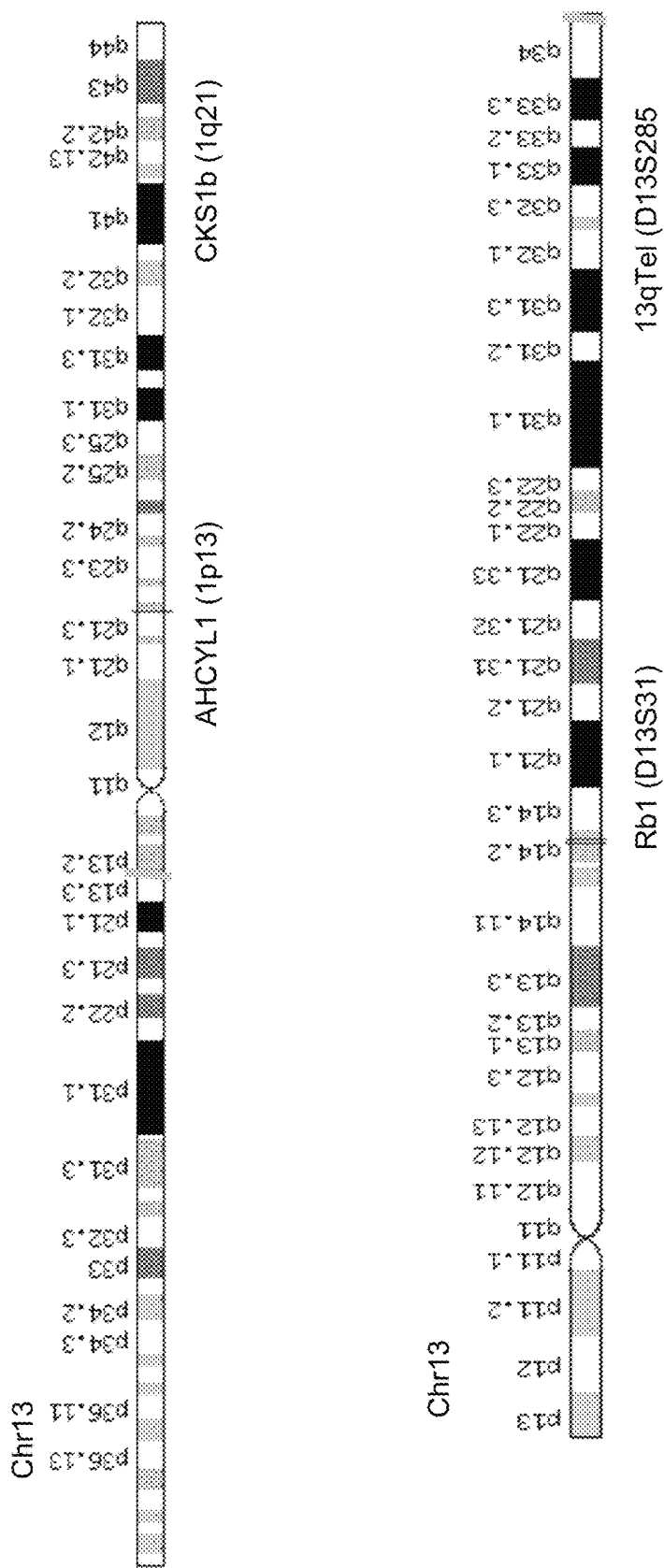
FIG. 10 shows the chromosome locations of AHCYL1 (1p13), CKS1b(1q21), Rb1(D13S31) and 13qTel (D13S285).
Figure 11:
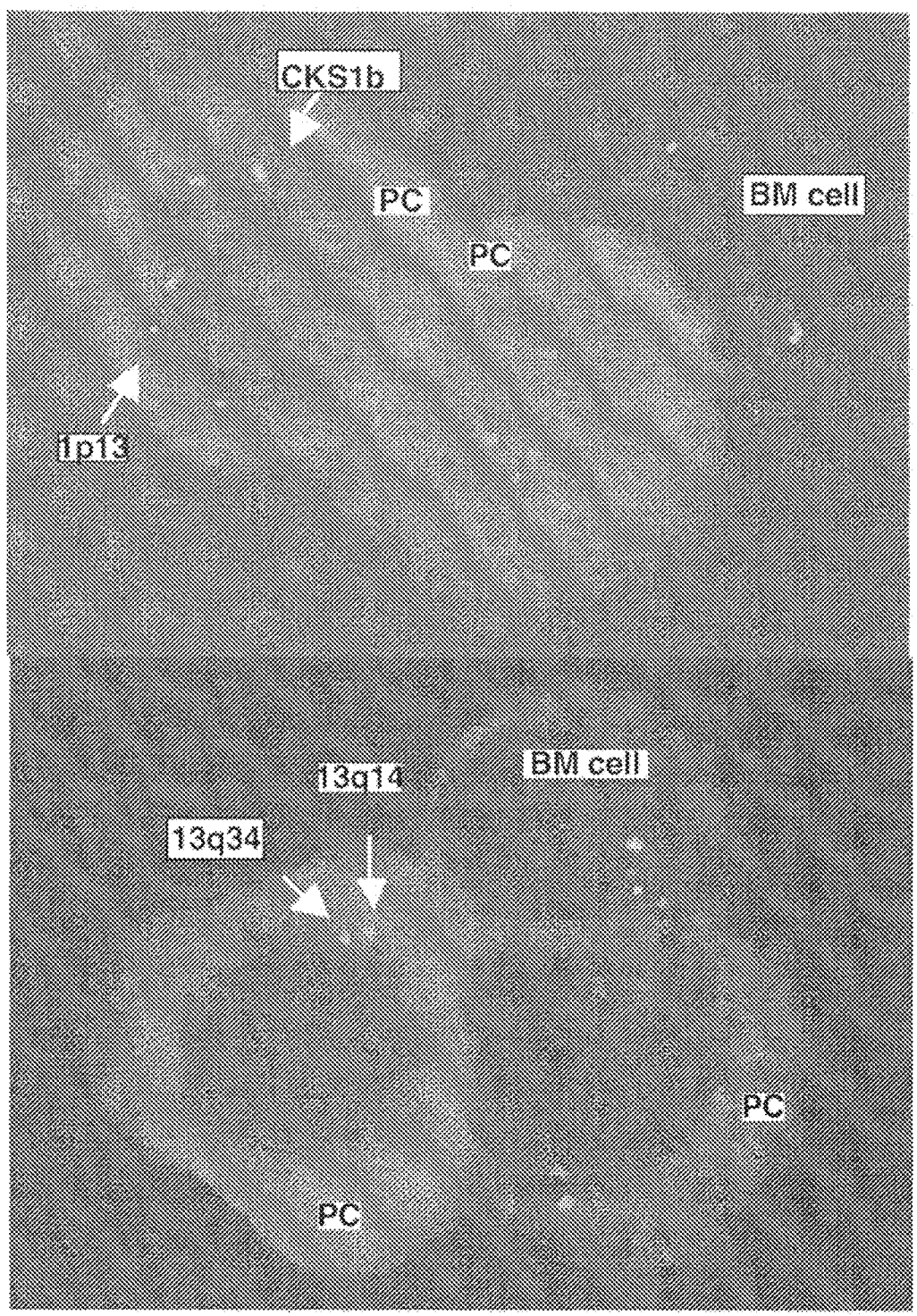
FIG. 11 shows a typical results of FISH on a bone marrow specimen of a patient with newly diagnosed multiple myeloma.

The total therapy 2 protocol enrolled 668 TT2 patients and the total therapy 3 protocols (TT3 and TT3b) enrolled 480 patients. A key difference between TT2 and TT3 is the administration of bortezomid in TT3 protocols. Bone marrow specimens were obtained at baseline, after treatment, and at relapse. FISH analysis has been carried out using probes for chromosome 1q21 (CKS1B), 1p13 (AHCYL1), 13q14 (D13S31/RB1) and 13qtel (D13S285) (FIG. 10). By simultaneously staining the tumor cells with the probes listed above labeled with nucleotides conjugated with red and green flourophores and an AMCA-labeled antibody that recognizes kappa or lambda light chain producing PC, clonally restricted tumor cells can be distinguished from a heterogeneous population of bone marrow cells under fluorescence microscopy. This technique was termed TRI-FISH for Triple color-FISH (FIG. 11). At least 100 light chain restricted cells are scored from each sample. Of 480 TT3/TT3b patients, 247 baseline specimens have been analyzed by FISH with the 4 probes. In addition, progress has been made to reexamine the specimens from TT2 patients with the 4 probes and 165 of these baseline specimens have been analyzed to date.

A summary of FISH results on baseline specimens from the combined TT2 and TT3/TT3b are summarized in Table 12

TABLE 12

FISH on the Baseline Myeloma Specimens (sample size: 517)

|  | 1q21 | 1p13 | D13S31 | D13S285 |
|---|---|---|---|---|
| momosomy | 3% | 21% | 45% | 42% |
| disomy | 60% | 74% | 52% | 54% |
| trisomy | 26% | 3% | 1% | 3% |
| tetrasomy or more | 12% | 2% | 1% | 1% |

The prognostic significance of FISH-defined copy number abnormalities for 1q21, 1p13 and 13q14 alone or in combination was investigated. Kaplan-Meier (KM) analysis of overall survival (FIGS. 12A-D, 14A-D, 16A-D, 22A-C, 23A-C, 24A-C, 25A-C, 26A, 27A, 28A and 29A) and event free survival (FIGS. 13A-D, 15A-D, 17A-D, 22D-F, 23D-F, 24D-F, 25D-F, 26B, 27B, 28B and 29B) related to FISH abnormalities of 1q21 (FIGS. 12A-D, 13A-D, 22A-F, 23A-F, 24A-F, 28A-B and 29A-B) 1p13 (FIGS. 14A-D, 15A-D, 24A-F and 26A-B) and 13q14 (FIGS. 16A-D, 17A-D, 25A-F and 27A-B) in the entire test cohort (upper left panel), TT3/TT3b (upper right panel), TT2-thalidomide (lower left panel) and TT2+thalidomide (lower right panel). KM analysis of overall survival and event free survival based on interactions between gains of 1q21 and loss of 1p13 (FIGS. 18A-D and 19A-D) and gain of 1q21 and deletion of 13q14 (FIGS. 20A-D and 21A-D) are shown as well. Univariate and multivariate analyses for these FISH abnormalities and molecular variables, standard prognostic variables and randomization to thalidomide are presented for TT2 (Tables 13a-d) and TT3/TT3b (Tables 14a-d).

TABLE 13A

Univariate and multivariate associations of FISH-defined Gain/Amp1q21 (3 or 4 copies) and molecular and clinical variables with overall and event-free survival in TT2

|  | Variable | n/N (%) | Overall Survival in TT2 HR (95% CI) | P-value | Event-free survival TT2 HR (95% CI) | P-value |
|---|---|---|---|---|---|---|
|  | Univariate |  |  |  |  |  |
|  | Age >= 65 yr | 25/125 (20%) | 1.47 (0.76, 2.81) | 0.251 | 1.27 (0.76, 2.11) | 0.359 |
|  | Albumin < 3.5 g/dL | 18/125 (14%) | 1.33 (0.62, 2.83) | 0.465 | 1.28 (0.72, 2.26) | 0.404 |
|  | B2M >= 3.5 mg/L | 47/125 (38%) | 2.12 (1.21, 3.70) | 0.008 | 1.46 (0.96, 2.22) | 0.079 |
|  | B2M > 5.5 mg/L | 27/125 (22%) | 2.13 (1.17, 3.86) | 0.013 | 1.40 (0.86, 2.26) | 0.174 |
|  | Creatinine >= 2 mg/dL | 15/122 (12%) | 1.90 (0.92, 3.92) | 0.083 | 1.54 (0.87, 2.73) | 0.138 |
|  | Hb < 10 g/dL | 36/125 (29%) | 1.10 (0.61, 1.99) | 0.756 | 0.98 (0.63, 1.54) | 0.939 |
|  | LDH >= 190 U/L | 33/125 (26%) | 2.17 (1.22, 3.85) | 0.008 | 1.42 (0.90, 2.25) | 0.132 |
|  | CRP >= 8 mg/L | 53/123 (43%) | 1.16 (0.66, 2.02) | 0.614 | 0.74 (0.48, 1.13) | 0.163 |
|  | Cytogenetic Abnormalities | 35/124 (28%) | 1.71 (0.95, 3.08) | 0.074 | 1.67 (1.07, 2.61) | 0.024 |
|  | GEP High Risk | 13/82 (16%) | 9.11 (4.22, 19.67) | <.001 | 3.51 (1.78, 6.89) | <.001 |
|  | Randomization to Thalidomide | 61/125 (49%) | 0.94 (0.54, 1.65) | 0.841 | 0.78 (0.52, 1.19) | 0.252 |
|  | Gain/Amp1q21 | 53/125 (42%) | 1.58 (0.91, 2.75) | 0.108 | 1.57 (1.03, 2.37) | 0.034 |
| Testing the | Randomization to Thalidomide | 61/125 (49%) | 1.10 (0.49, 2.45) | 0.812 | 1.08 (0.61, 1.92) | 0.785 |
| interaction | Gain/Amp1q21 | 53/125 (42%) | 2.11 (0.99, 4.52) | 0.054 | 3.26 (1.83, 5.82) | <.001 |
| between | +Thal/Gain/Amp1q21 | 32/125 (26%) | 0.58 (0.19, 1.79) | 0.346 | 0.31 (0.13, 0.72) | 0.006 |
| Thalidomide | GEP IFN >= 11 | 15/82 (18%) | 1.19 (0.49, 2.88) | 0.703 | 0.92 (0.47, 1.82) | 0.812 |
| and FISH | GEP NFKB score >= 11 | 25/82 (30%) | 0.58 (0.25, 1.34) | 0.201 | 1.04 (0.60, 1.81) | 0.882 |
|  | GEP Centrosome Index >= 3 | 13/82 (16%) | 2.35 (1.06, 5.21) | 0.035 | 1.86 (0.98, 3.52) | 0.057 |
|  | GEP Proliferation Index >= 10 | 9/82 (11%) | 2.95 (1.27, 6.83) | 0.012 | 2.05 (0.96, 4.39) | 0.063 |
|  | GEP Poly PC Score >= 13 | 1/82 (1%) | 2.83 (0.38, 20.97) | 0.309 | 1.45 (0.20, 10.55) | 0.715 |
|  | Multivariate |  |  |  |  |  |
|  | Randomization to Thalidomide | 37/78 (47%) | 2.32 (0.74, 7.34) | 0.151 | 1.37 (0.63, 2.95) | 0.429 |
|  | Gain/Amp1q21 | 37/78 (47%) | 2.08 (0.71, 6.13) | 0.184 | 2.51 (1.19, 5.30) | 0.016 |
|  | +Thal/Gain/Amp1q21 | 22/78 (28%) | 0.24 (0.06, 1.06) | 0.059 | 0.36 (0.13, 1.04) | 0.059 |
|  | B2M >= 3.5 mg/L | 31/78 (40%) | 2.29 (1.03, 5.11) | 0.042 | NS2 | NS2 |
|  | LDH >= 190 U/L | 23/78 (29%) | 2.61 (1.17, 5.81) | 0.019 | 1.84 (1.05, 3.21) | 0.033 |
|  | GEP High Risk | 12/78 (15%) | 12.61 (4.69, 33.90) | <.001 | 3.09 (1.46, 6.56) | 0.003 |
|  | GEP Poly PC Score >= 13 | 1/78 (1%) | 15.37 (1.67, 141.14) | 0.016 | NS2 | NS2 |

HR - Hazard Ratio, 95% CI - 95% Confidence Interval, P-value from Wald Chi-Square Test in Cox Regression

TABLE 13B

Univariate and multivariate associations of FISH-defined Amp1q21 (4 copies) and molecular and clinical variables with overall and event-free survival in TT2

|  | Variable | n/N (%) | Overall Survival in TT2 HR (95% CI) | P-value | Event-free survival TT2 HR (95% CI) | P-value |
|---|---|---|---|---|---|---|
|  | Univariate |  |  |  |  |  |
|  | Age >= 65 yr | 20/89 (22%) | 2.05 (0.96, 4.37) | 0.062 | 1.31 (0.73, 2.35) | 0.361 |
|  | Albumin < 3.5 g/dL | 9/89 (10%) | 0.92 (0.28, 3.04) | 0.897 | 1.67 (0.79, 3.51) | 0.179 |
|  | B2M >= 3.5 mg/L | 32/89 (36%) | 1.88 (0.94, 3.78) | 0.075 | 1.28 (0.77, 2.13) | 0.341 |
|  | B2M > 5.5 mg/L | 16/89 (18%) | 1.54 (0.69, 3.44) | 0.288 | 1.03 (0.55, 1.93) | 0.929 |
|  | Creatinine >= 2 mg/dL | 8/86 (9%) | 1.37 (0.48, 3.93) | 0.556 | 1.05 (0.48, 2.31) | 0.904 |
|  | Hb < 10 g/dL | 22/89 (25%) | 0.89 (0.40, 1.98) | 0.776 | 0.92 (0.52, 1.62) | 0.774 |
|  | LDH >= 190 U/L | 21/89 (24%) | 1.75 (0.83, 3.70) | 0.145 | 1.29 (0.72, 2.31) | 0.397 |
|  | CRP >= 8 mg/L | 38/89 (43%) | 0.96 (0.48, 1.93) | 0.913 | 0.67 (0.40, 1.11) | 0.124 |
|  | Cytogenetic Abnormalities | 22/88 (25%) | 1.24 (0.55, 2.77) | 0.607 | 1.85 (1.07, 3.18) | 0.028 |
|  | GEP High Risk | 4/55 (7%) | 18.90 (4.82, 74.14) | <.001 | 6.12 (1.94, 19.35) | 0.002 |
|  | Randomization Thalidomide | 39/89 (44%) | 1.10 (0.55, 2.22) | 0.781 | 0.97 (0.59, 1.60) | 0.899 |
|  | Amp1q21 | 17/89 (19%) | 1.42 (0.61, 3.29) | 0.416 | 1.60 (0.88, 2.91) | 0.123 |
| Testing the | Randomization Thalidomide | 39/89 (44%) | 1.11 (0.50, 2.48) | 0.795 | 1.08 (0.61, 1.92) | 0.785 |
| interaction | Amp1q21 | 17/89 (19%) | 1.61 (0.47, 5.59) | 0.451 | 2.91 (1.25, 6.78) | 0.013 |
| between | +Thal/Amp1q21 | 10/89 (11%) | 0.77 (0.14, 4.24) | 0.769 | 0.37 (0.11, 1.23) | 0.105 |
| Thalidomide | GEP IFN >= 11 | 13/55 (24%) | 1.06 (0.35, 3.24) | 0.913 | 0.88 (0.40, 1.92) | 0.741 |
| and FISH | GEP NFKB score >= 11 | 20/55 (36%) | 0.50 (0.16, 1.51) | 0.217 | 0.92 (0.47, 1.81) | 0.815 |
|  | GEP Centrosome Index >= 3 | 6/55 (11%) | 1.25 (0.29, 5.45) | 0.766 | 1.55 (0.60, 4.00) | 0.361 |
|  | GEP Proliferation Index >= 10 | 1/55 (2%) | 5.95 (0.74, 47.65) | 0.093 | 2.84 (0.38, 21.46) | 0.311 |
|  | GEP Poly PC Score >= 13 | 1/55 (2%) | 3.98 (0.51, 30.86) | 0.187 | 1.87 (0.25, 13.92) | 0.539 |
|  | Multivariate |  |  |  |  |  |
|  | Randomization to Thalidomide | 21/52 (40%) | 2.24 (0.70, 7.11) | 0.173 | 2.23 (0.94, 5.31) | 0.070 |
|  | Amp1q21 | 11/52 (21%) | 1.05 (0.17, 6.27) | 0.961 | 2.10 (0.73, 6.01) | 0.168 |
|  | +Thal/Amp1q21 | 6/52 (12%) | 1.14 (0.09, 13.63) | 0.920 | 0.30 (0.06, 1.38) | 0.122 |
|  | Cytogenetic Abnormalities | 14/52 (27%) | NS2 | NS2 | 3.07 (1.33, 7.10) | 0.009 |
|  | LDH >= 190 U/L | 13/52 (25%) | 3.95 (1.34, 11.61) | 0.013 | NS2 | NS2 |
|  | GEP High Risk | 4/52 (8%) | 37.16 (6.52, 211.73) | <.001 | NS2 | NS2 |
|  | GEP Poly PC Score >= 13 | 1/52 (2%) | 15.66 (1.50, 163.66) | 0.022 | NS2 | NS2 |

HR - Hazard Ratio, 95% CI—95% Confidence Interval, P-value from Wald Chi-Square Test in Cox Regression
NS2 - Multivariate results not statistically significant at 0.05 level. All univariate p-values reported regardless of significance.
Multivariate model uses stepwise selection with entry level 0.1 and variable remains if meets the 0.05 level.
A multivariate p-value greater than 0.05 indicates variable forced into model with significant variables chosen using stepwise selection.

TABLE 13C

Univariate and multivariate associations of FISH-defined del1p13 and molecular and clinical variables with overall and event-free survival in TT2

|  | Variable | n/N (%) | Overall Survival in TT2 HR (95% CI) | P-value | Event-free survival TT2 HR (95% CI) | P-value |
|---|---|---|---|---|---|---|
|  | Univariate |  |  |  |  |  |
|  | Age >= 65 yr | 25/123 (20%) | 1.38 (0.72, 2.65) | 0.334 | 1.21 (0.73, 2.02) | 0.458 |
|  | Albumin < 3.5 g/dL | 17/122 (14%) | 1.41 (0.66, 3.01) | 0.369 | 1.49 (0.84, 2.64) | 0.174 |
|  | B2M >= 3.5 mg/L | 47/123 (38%) | 1.88 (1.07, 3.28) | 0.027 | 1.38 (0.90, 2.11) | 0.138 |
|  | B2M > 5.5 mg/L | 26/123 (21%) | 2.00 (1.09, 3.67) | 0.025 | 1.39 (0.85, 2.28) | 0.184 |
|  | Creatinine >= 2 mg/dL | 14/120 (12%) | 1.81 (0.85, 3.86) | 0.127 | 1.60 (0.89, 2.89) | 0.120 |
|  | Hb < 10 g/dL | 35/123 (28%) | 1.12 (0.62, 2.02) | 0.718 | 0.96 (0.61, 1.52) | 0.869 |
|  | LDH >= 190 U/L | 34/123 (28%) | 1.98 (1.12, 3.52) | 0.020 | 1.32 (0.83, 2.09) | 0.238 |
|  | CRP >= 8 mg/L | 51/121 (42%) | 1.08 (0.62, 1.89) | 0.787 | 0.70 (0.46, 1.08) | 0.109 |
|  | Cytogenetic Abnormalities | 35/122 (29%) | 1.63 (0.91, 2.94) | 0.103 | 1.61 (1.03, 2.51) | 0.038 |
|  | GEP High Risk | 13/82 (16%) | 8.62 (4.04, 18.41) | <.001 | 3.32 (1.69, 6.51) | <.001 |
|  | Randomization to Thalidomide | 56/123 (46%) | 1.04 (0.60, 1.82) | 0.888 | 0.83 (0.54, 1.27) | 0.388 |
|  | del1p13 | 24/123 (20%) | 1.85 (0.97, 3.56) | 0.063 | 1.52 (0.90, 2.55) | 0.116 |
| Testing the | Randomization to Thalidomide | 56/123 (46%) | 0.91 (0.48, 1.73) | 0.772 | 0.75 (0.47, 1.21) | 0.237 |
| interaction | del1p13 | 24/123 (20%) | 1.36 (0.55, 3.35) | 0.507 | 1.16 (0.58, 2.31) | 0.679 |
| between | +Thal/del1p13 | 11/123 (9%) | 2.11 (0.57, 7.78) | 0.263 | 1.91 (0.67, 5.45) | 0.224 |
| Thalidomide | GEP IFN >= 11 | 15/82 (18%) | 1.12 (0.46, 2.69) | 0.809 | 0.90 (0.46, 1.78) | 0.766 |
| and FISH | GEP NFKB score >= 11 | 26/82 (32%) | 0.62 (0.28, 1.36) | 0.232 | 1.04 (0.60, 1.79) | 0.887 |
|  | GEP Centrosome Index >= 3 | 12/82 (15%) | 2.68 (1.21, 5.93) | 0.015 | 1.84 (0.96, 3.56) | 0.068 |
|  | GEP Proliferation Index >= 10 | 9/82 (11%) | 2.79 (1.21, 6.44) | 0.016 | 1.99 (0.93, 4.24) | 0.076 |
|  | GEP Poly PC Score >= 13 | 1/82 (1%) | 2.66 (0.36, 19.72) | 0.337 | 1.35 (0.19, 9.80) | 0.768 |

TABLE 13C-continued

Univariate and multivariate associations of FISH-defined del1p13 and molecular and clinical variables with overall and event-free survival in TT2

| Variable | n/N (%) | Overall Survival in TT2 | | Event-free survival TT2 | |
|---|---|---|---|---|---|
| | | HR (95% CI) | P-value | HR (95% CI) | P-value |
| Multivariate | | | | | |
| Randomization to Thalidomide | 35/77 (45%) | 1.15 (0.49, 2.70) | 0.746 | 0.84 (0.45, 1.57) | 0.589 |
| del1p13 | 19/77 (25%) | 1.77 (0.62, 5.10) | 0.288 | 1.03 (0.45, 2.39) | 0.941 |
| +Thal/del1p13 | 10/77 (13%) | 0.51 (0.11, 2.47) | 0.404 | 1.57 (0.41, 5.99) | 0.510 |
| GEP High Risk | 12/77 (16%) | 10.24 (3.86, 27.13) | <.001 | 2.78 (1.15, 6.72) | 0.023 |
| LDH >= 190 U/L | 24/77 (31%) | 2.69 (1.31, 5.53) | 0.007 | NS2 | NS2 |

HR - Hazard Ratio, 95% CI - 95% Confidence Interval, P-value from Wald Chi-Square Test in Cox Regression
NS2 - Multivariate results not statistically significant at 0.05 level. All univariate p-values reported regardless of significance.
Multivariate model uses stepwise selection with entry level 0.1 and variable remains if meets the 0.05 level.
A multivariate p-value greater than 0.05 indicates variable forced into model with significant variables chosen using stepwise selection.

TABLE 13D

Univariate and multivariate associations of FISH defined del13q14 and molecular and clinical variables with overall and event-free survival in TT2

| | Variable | n/N (%) | Overall Survival in TT2 | | Event-free survival TT2 | |
|---|---|---|---|---|---|---|
| | | | HR (95% CI) | P-value | HR (95% CI) | P-value |
| | Univariate | | | | | |
| | Age >= 65 yr | 25/126 (20%) | 1.42 (0.74, 2.72) | 0.293 | 1.23 (0.74, 2.05) | 0.416 |
| | Albumin < 3.5 g/dL | 17/125 (14%) | 1.44 (0.67, 3.05) | 0.348 | 1.48 (0.84, 2.62) | 0.177 |
| | B2M >= 3.5 mg/L | 48/126 (38%) | 1.97 (1.13, 3.42) | 0.016 | 1.37 (0.90, 2.08) | 0.144 |
| | B2M > 5.5 mg/L | 27/126 (21%) | 2.06 (1.14, 3.73) | 0.017 | 1.36 (0.84, 2.20) | 0.208 |
| | Creatinine >= 2 mg/dL | 15/123 (12%) | 1.85 (0.90, 3.82) | 0.095 | 1.51 (0.85, 2.67) | 0.160 |
| | Hb < 10 g/dL | 35/126 (28%) | 1.13 (0.63, 2.05) | 0.677 | 0.97 (0.61, 1.52) | 0.885 |
| | LDH >= 190 U/L | 34/126 (27%) | 2.01 (1.14, 3.57) | 0.016 | 1.33 (0.84, 2.10) | 0.224 |
| | CRP >= 8 mg/L | 53/124 (43%) | 1.10 (0.63, 1.91) | 0.739 | 0.71 (0.47, 1.09) | 0.119 |
| | Cytogenetic Abnormalities | 35/125 (28%) | 1.66 (0.92, 2.98) | 0.091 | 1.62 (1.04, 2.53) | 0.033 |
| | GEP High Risk | 13/83 (16%) | 8.78 (4.11, 18.76) | <.001 | 3.33 (1.70, 6.53) | <.001 |
| | Randomization to Thalidomide | 59/126 (47%) | 1.00 (0.58, 1.74) | 0.987 | 0.82 (0.54, 1.24) | 0.343 |
| | del13q14 | 75/126 (60%) | 1.08 (0.62, 1.90) | 0.775 | 1.07 (0.70, 1.61) | 0.763 |
| Testing the | Randomization to Thalidomide | 59/126 (47%) | 1.19 (0.49, 2.88) | 0.694 | 0.99 (0.52, 1.92) | 0.986 |
| interaction | del13q14 | 75/126 (60%) | 1.24 (0.59, 2.60) | 0.573 | 1.30 (0.75, 2.23) | 0.353 |
| between | +Thal/del13q14 | 40/126 (32%) | 0.73 (0.24, 2.28) | 0.593 | 0.70 (0.30, 1.63) | 0.403 |
| Thalidomide | GEP IFN >= 11 | 15/83 (18%) | 1.14 (0.47, 2.75) | 0.772 | 0.89 (0.45, 1.77) | 0.748 |
| and FISH | GEP NFKB score >= 11 | 26/83 (31%) | 0.63 (0.29, 1.40) | 0.258 | 1.04 (0.60, 1.78) | 0.893 |
| | GEP Centrosome Index >= 3 | 13/83 (16%) | 2.27 (1.03, 5.00) | 0.043 | 1.79 (0.95, 3.38) | 0.073 |
| | GEP Proliferation Index >= 10 | 9/83 (11%) | 2.84 (1.23, 6.56) | 0.014 | 1.99 (0.93, 4.24) | 0.076 |
| | GEP Poly PC Score >= 13 | 1/83 (1%) | 2.71 (0.37, 20.04) | 0.329 | 1.37 (0.19, 9.98) | 0.754 |
| | Multivariate | | | | | |
| | Randomization to Thalidomide | 36/78 (46%) | 1.82 (0.55, 6.01) | 0.326 | 1.19 (0.49, 2.87) | 0.704 |
| | del13q14 | 51/78 (65%) | 1.19 (0.43, 3.30) | 0.739 | 1.02 (0.50, 2.08) | 0.958 |
| | +Thal/del13q14 | 26/78 (33%) | 0.39 (0.09, 1.73) | 0.214 | 0.70 (0.23, 2.13) | 0.534 |
| | GEP High Risk | 12/78 (15%) | 12.09 (4.79, 30.54) | <.001 | 3.73 (1.75, 7.94) | <.001 |
| | LDH >= 190 U/L | 24/78 (31%) | 2.82 (1.36, 5.81) | 0.005 | NS2 | NS2 |

HR - Hazard Ratio, 95% CI - 95% Confidence Interval, P-value from Wald Chi-Square Test in Cox Regression
NS2 - Multivariate results not statistically significant at 0.05 level. All univariate p-values reported regardless of significance.
Multivariate model uses stepwise selection with entry level 0.1 and variable remains if meets the 0.05 level.
A multivariate p-value greater than 0.05 indicates variable forced into model with significant variables chosen using stepwise selection.

TABLE 14A

Univariate and multivariate associations of FISH-defined Gain/Amp1q21 (3 or 4 copies) and molecular and clinical variables with overall and event-free survival in TT3

| | | Overall Survival in TT3 | | Event-free survival TT3 | |
|---|---|---|---|---|---|
| Variable | n/N (%) | HR (95% CI) | P-value | HR (95% CI) | P-value |
| *Univariate* | | | | | |
| Age >= 65 yr | 68/240 (28%) | 1.22 (0.64, 2.35) | 0.543 | 1.26 (0.71, 2.24) | 0.425 |
| Albumin < 3.5 g/dL | 80/239 (33%) | 1.90 (1.04, 3.49) | 0.038 | 1.77 (1.04, 3.02) | 0.037 |
| B2M >= 3.5 mg/L | 120/238 (50%) | 2.27 (1.21, 4.27) | 0.011 | 2.25 (1.29, 3.94) | 0.004 |
| B2M > 5.5 mg/L | 62/238 (26%) | 3.95 (2.15, 7.25) | <.001 | 4.18 (2.45, 7.15) | <.001 |
| Creatinine >= 2 mg/dL | 17/239 (7%) | 2.09 (0.82, 5.32) | 0.121 | 2.33 (1.05, 5.15) | 0.037 |
| Hb < 10 g/dL | 80/239 (33%) | 1.74 (0.96, 3.18) | 0.069 | 1.98 (1.17, 3.36) | 0.011 |
| LDH >= 190 U/L | 66/239 (28%) | 2.17 (1.18, 3.98) | 0.012 | 2.54 (1.49, 4.32) | <.001 |
| CRP >= 8 mg/L | 76/238 (32%) | 1.39 (0.75, 2.59) | 0.297 | 1.22 (0.70, 2.14) | 0.477 |
| Cytogenetic Abnormalities | 102/236 (43%) | 3.03 (1.59, 5.75) | <.001 | 2.39 (1.38, 4.14) | 0.002 |
| GEP High Risk | 43/227 (19%) | 4.28 (2.30, 7.97) | <.001 | 4.23 (2.44, 7.33) | <.001 |
| Gain/Amp1q21 | 87/240 (36%) | 1.60 (0.88, 2.91) | 0.126 | 1.58 (0.93, 2.68) | 0.094 |
| GEP IFN >= 11 | 55/227 (24%) | 1.92 (1.02, 3.61) | 0.044 | 1.76 (1.00, 3.12) | 0.050 |
| GEP NFKB score >= 11 | 101/227 (44%) | 0.89 (0.48, 1.64) | 0.705 | 0.90 (0.52, 1.55) | 0.699 |
| GEP Centrosome Index >= 3 | 86/227 (38%) | 3.89 (2.05, 7.37) | <.001 | 2.84 (1.63, 4.93) | <.001 |
| GEP Proliferation Index >= 10 | 28/227 (12%) | 3.99 (2.09, 7.60) | <.001 | 3.48 (1.93, 6.26) | <.001 |
| GEP Poly PC Score >= 13 | 8/227 (4%) | 1.31 (0.32, 5.45) | 0.707 | 1.01 (0.24, 4.15) | 0.992 |
| *Multivariate* | | | | | |
| Gain/Amp1q21 | 82/220 (37%) | 1.36 (0.69, 2.71) | 0.378 | 1.27 (0.71, 2.27) | 0.424 |
| B2M > 5.5 mg/L | 59/220 (27%) | NS2 | NS2 | 2.50 (1.37, 4.58) | 0.003 |
| Creatinine >= 2 mg/dL | 16/220 (7%) | 3.16 (1.17, 8.52) | 0.023 | NS2 | NS2 |
| Cytogenetic Abnormalities | 96/220 (44%) | 2.83 (1.38, 5.78) | 0.004 | NS2 | NS2 |
| GEP High Risk | 42/220 (19%) | NS2 | NS2 | 3.02 (1.60, 5.69) | <.001 |
| GEP IFN >= 11 | 52/220 (24%) | 3.20 (1.53, 6.68) | 0.002 | 2.23 (1.22, 4.07) | 0.010 |
| GEP Centrosome Index >= 3 | 83/220 (38%) | 3.86 (1.93, 7.74) | <.001 | NS2 | NS2 |
| GEP Poly PC Score >= 13 | 7/220 (3%) | 7.40 (1.49, 36.85) | 0.015 | NS2 | NS2 |

HR - Hazard Ratio, 95% CI - 95% Confidence Interval, P-value from Wald Chi-Square Test in Cox Regression
NS2 - Multivariate results not statistically significant at 0.05 level. All univariate p-values reported regardless of significance.
Multivariate model uses stepwise selection with entry level 0.1 and variable remains if meets the 0.05 level.
A multivariate p-value greater than 0.05 indicates variable forced into model with significant variables chosen using stepwise selection.

TABLE 14B

Univariate and multivariate associations of FISH-defined Amp1q21 (4 copies) and molecular and clinical variables with overall and event-free survival in TT3

| | | Overall Survival in TT3 | | Event-free survival TT3 | |
|---|---|---|---|---|---|
| Variable | n/N (%) | HR (95% CI) | P-value | HR (95% CI) | P-value |
| *Univariate* | | | | | |
| Age >= 65 yr | 68/240 (28%) | 1.22 (0.64, 2.35) | 0.543 | 1.26 (0.71, 2.24) | 0.425 |
| Albumin < 3.5 g/dL | 80/239 (33%) | 1.90 (1.04, 3.49) | 0.038 | 1.77 (1.04, 3.02) | 0.037 |
| B2M >= 3.5 mg/L | 120/238 (50%) | 2.27 (1.21, 4.27) | 0.011 | 2.25 (1.29, 3.94) | 0.004 |
| B2M > 5.5 mg/L | 62/238 (26%) | 3.95 (2.15, 7.25) | <.001 | 4.18 (2.45, 7.15) | <.001 |
| Creatinine >= 2 mg/dL | 17/239 (7%) | 2.09 (0.82, 5.32) | 0.121 | 2.33 (1.05, 5.15) | 0.037 |
| Hb < 10 g/dL | 80/239 (33%) | 1.74 (0.96, 3.18) | 0.069 | 1.98 (1.17, 3.36) | 0.011 |
| LDH >= 190 U/L | 66/239 (28%) | 2.17 (1.18, 3.98) | 0.012 | 2.54 (1.49, 4.32) | <.001 |
| CRP >= 8 mg/L | 76/238 (32%) | 1.39 (0.75, 2.59) | 0.297 | 1.22 (0.70, 2.14) | 0.477 |
| Cytogenetic Abnormalities | 102/236 (43%) | 3.03 (1.59, 5.75) | <.001 | 2.39 (1.38, 4.14) | 0.002 |
| GEP High Risk | 43/227 (19%) | 4.28 (2.30, 7.97) | <.001 | 4.23 (2.44, 7.33) | <.001 |
| Amp1q21 | 25/178 (14%) | 3.56 (1.73, 7.31) | <.001 | 3.10 (1.59, 6.07) | <.001 |
| GEP IFN >= 11 | 55/227 (24%) | 1.92 (1.02, 3.61) | 0.044 | 1.76 (1.00, 3.12) | 0.050 |
| GEP NFKB score >= 11 | 101/227 (44%) | 0.89 (0.48, 1.64) | 0.705 | 0.90 (0.52, 1.55) | 0.699 |
| GEP Centrosome Index >= 3 | 86/227 (38%) | 3.89 (2.05, 7.37) | <.001 | 2.84 (1.63, 4.93) | <.001 |
| GEP Proliferation Index >= 10 | 28/227 (12%) | 3.99 (2.09, 7.60) | <.001 | 3.48 (1.93, 6.26) | <.001 |
| GEP Poly PC Score >= 13 | 8/227 (4%) | 1.31 (0.32, 5.45) | 0.707 | 1.01 (0.24, 4.15) | 0.992 |
| *Multivariate* | | | | | |
| 4 signals of 1q21 | 23/161 (14%) | 2.38 (0.96, 5.87) | 0.061 | 2.66 (1.20, 5.91) | 0.016 |
| B2M > 5.5 mg/L | 43/161 (27%) | NS2 | NS2 | 2.66 (1.34, 5.30) | 0.005 |

TABLE 14B-continued

Univariate and multivariate associations of FISH-defined Amp1q21 (4 copies) and molecular and clinical variables with overall and event-free survival in TT3

| Variable | n/N (%) | Overall Survival in TT3 HR (95% CI) | P-value | Event-free survival TT3 HR (95% CI) | P-value |
|---|---|---|---|---|---|
| GEP Centrosome Index >= 3 | 61/161 (38%) | 2.95 (1.27, 6.90) | 0.012 | NS2 | NS2 |
| GEP IFN >= 11 | 43/161 (27%) | 2.85 (1.28, 6.36) | 0.010 | 2.87 (1.39, 5.90) | 0.004 |
| GEP Proliferation Index >= 10 | 16/161 (10%) | 3.13 (1.35, 7.29) | 0.008 | 3.46 (1.59, 7.51) | 0.002 |

HR - Hazard Ratio, 95% CI - 95% Confidence Interval, P-value from Wald Chi-Square Test in Cox Regression
NS2 - Multivariate results not statistically significant at 0.05 level. All univariate p-values reported regardless of significance.
Multivariate model uses stepwise selection with entry level 0.1 and variable remains if meets the 0.05 level.
A multivariate p-value greater than 0.05 indicates variable forced into model with significant variables chosen using stepwise selection.

TABLE 14C

Univariate and multivariate associations of FISH-defined del1p13 and molecular and clinical variables with overall and event-free survival in TT3

| Variable | n/N (%) | Overall Survival in TT3 HR (95% CI) | P-value | Event-free survival TT3 HR (95% CI) | P-value |
|---|---|---|---|---|---|
| Univariate | | | | | |
| Age >= 65 yr | 68/235 (29%) | 1.34 (0.71, 2.54) | 0.366 | 1.36 (0.77, 2.39) | 0.286 |
| Albumin < 3.5 g/dL | 79/234 (34%) | 2.33 (1.28, 4.27) | 0.006 | 2.10 (1.24, 3.58) | 0.006 |
| B2M >= 3.5 mg/L | 123/233 (53%) | 2.27 (1.20, 4.31) | 0.012 | 2.21 (1.25, 3.88) | 0.006 |
| B2M > 5.5 mg/L | 61/233 (26%) | 3.93 (2.14, 7.21) | <.001 | 4.19 (2.45, 7.16) | <.001 |
| Creatinine >= 2 mg/dL | 17/234 (7%) | 2.02 (0.79, 5.14) | 0.140 | 2.26 (1.02, 5.00) | 0.044 |
| Hb < 10 g/dL | 80/234 (34%) | 1.87 (1.03, 3.40) | 0.041 | 2.09 (1.23, 3.55) | 0.006 |
| LDH >= 190 U/L | 64/234 (27%) | 1.73 (0.93, 3.21) | 0.083 | 2.12 (1.24, 3.62) | 0.006 |
| CRP >= 8 mg/L | 74/233 (32%) | 1.24 (0.66, 2.33) | 0.496 | 1.12 (0.63, 1.96) | 0.705 |
| Cytogenetic Abnormalities | 97/231 (42%) | 2.88 (1.53, 5.43) | 0.001 | 2.34 (1.36, 4.02) | 0.002 |
| GEP High Risk | 41/223 (18%) | 4.22 (2.24, 7.94) | <.001 | 4.20 (2.41, 7.34) | <.001 |
| del1p13 | 51/235 (22%) | 1.55 (0.79, 3.01) | 0.201 | 1.72 (0.97, 3.06) | 0.062 |
| GEP IFN >= 11 | 55/223 (25%) | 1.91 (1.01, 3.61) | 0.047 | 1.76 (0.99, 3.12) | 0.053 |
| GEP NFKB score >= 11 | 100/223 (45%) | 0.93 (0.50, 1.73) | 0.822 | 0.92 (0.53, 1.60) | 0.779 |
| GEP Centrosome Index >= 3 | 83/223 (37%) | 3.38 (1.78, 6.38) | <.001 | 2.55 (1.47, 4.44) | <.001 |
| GEP Proliferation Index >= 10 | 25/223 (11%) | 4.15 (2.14, 8.04) | <.001 | 3.64 (1.99, 6.64) | <.001 |
| GEP Poly PC Score >= 13 | 8/223 (4%) | 1.30 (0.31, 5.41) | 0.716 | 1.00 (0.24, 4.13) | 0.998 |
| Multivariate | | | | | |
| del1p13 | 47/216 (22%) | 0.84 (0.39, 1.84) | 0.669 | 0.97 (0.50, 1.89) | 0.925 |
| B2M > 5.5 mg/L | 57/216 (26%) | NS2 | NS2 | 2.44 (1.31, 4.55) | 0.005 |
| GEP High Risk | 40/216 (19%) | 2.96 (1.33, 6.61) | 0.008 | 3.16 (1.59, 6.28) | 0.001 |
| GEP Centrosome Index >= 3 | 80/216 (37%) | 2.30 (1.07, 4.96) | 0.033 | NS2 | NS2 |
| GEP IFN >= 11 | 52/216 (24%) | 2.57 (1.33, 4.96) | 0.005 | 2.10 (1.16, 3.80) | 0.015 |

HR - Hazard Ratio, 95% CI - 95% Confidence Interval, P-value from Wald Chi-Square Test in Cox Regression
NS2 - Multivariate results not statistically significant at 0.05 level. All univariate p-values reported regardless of significance.
Multivariate model uses stepwise selection with entry level 0.1 and variable remains if meets the 0.05 level.
A multivariate p-value greater than 0.05 indicates variable forced into model with significant variables chosen using stepwise selection.

TABLE 14D

Univariate and multivariate associations of FISH defined del13q14 and molecular and clinical variables with overall and event-free survival in TT3

| Variable | n/N (%) | Overall Survival in TT3 HR (95% CI) | P-value | Event-free survival TT3 HR (95% CI) | P-value |
|---|---|---|---|---|---|
| Univariate | | | | | |
| Age >= 65 yr | 71/243 (29%) | 1.38 (0.74, 2.56) | 0.312 | 1.42 (0.82, 2.48) | 0.211 |
| Albumin < 3.5 g/dL | 82/242 (34%) | 2.08 (1.15, 3.75) | 0.015 | 1.99 (1.17, 3.37) | 0.011 |
| B2M >= 3.5 mg/L | 124/241 (51%) | 2.31 (1.24, 4.30) | 0.008 | 2.42 (1.38, 4.24) | 0.002 |
| B2M > 5.5 mg/L | 63/241 (26%) | 3.92 (2.17, 7.10) | <.001 | 4.37 (2.57, 7.43) | <.001 |
| Creatinine >= 2 mg/dL | 17/242 (7%) | 1.98 (0.78, 5.03) | 0.149 | 2.30 (1.04, 5.09) | 0.039 |
| Hb < 10 g/dL | 81/242 (33%) | 1.77 (0.99, 3.19) | 0.055 | 2.09 (1.24, 3.53) | 0.006 |
| LDH >= 190 U/L | 66/242 (27%) | 1.99 (1.10, 3.62) | 0.024 | 2.47 (1.46, 4.18) | <.001 |
| CRP >= 8 mg/L | 78/241 (32%) | 1.38 (0.75, 2.52) | 0.298 | 1.26 (0.73, 2.18) | 0.407 |

TABLE 14D-continued

Univariate and multivariate associations of FISH defined del13q14 and molecular
and clinical variables with overall and event-free survival in TT3

| | | Overall Survival in TT3 | | Event-free survival TT3 | |
|---|---|---|---|---|---|
| Variable | n/N (%) | HR (95% CI) | P-value | HR (95% CI) | P-value |
| Cytogenetic Abnormalities | 103/239 (43%) | 2.91 (1.56, 5.43) | <.001 | 2.26 (1.31, 3.87) | 0.003 |
| GEP High Risk | 42/229 (18%) | 4.21 (2.28, 7.79) | <.001 | 4.43 (2.56, 7.67) | <.001 |
| del13q14 | 121/243 (50%) | 1.15 (0.64, 2.06) | 0.646 | 1.38 (0.82, 2.35) | 0.229 |
| GEP IFN >= 11 | 56/229 (24%) | 1.80 (0.96, 3.37) | 0.068 | 1.73 (0.98, 3.06) | 0.059 |
| GEP NFKB score >= 11 | 104/229 (45%) | 0.92 (0.50, 1.68) | 0.782 | 0.95 (0.55, 1.63) | 0.856 |
| GEP Centrosome Index >= 3 | 87/229 (38%) | 3.56 (1.90, 6.66) | <.001 | 2.81 (1.62, 4.88) | <.001 |
| GEP Proliferation Index >= 10 | 28/229 (12%) | 3.87 (2.04, 7.35) | <.001 | 3.52 (1.96, 6.34) | <.001 |
| GEP Poly PC Score >= 13 | 8/229 (3%) | 1.29 (0.31, 5.36) | 0.724 | 1.02 (0.25, 4.20) | 0.978 |
| Multivariate | | | | | |
| del13q14 | 111/222 (50%) | 0.83 (0.44, 1.58) | 0.578 | 0.95 (0.53, 1.71) | 0.870 |
| B2M > 5.5 mg/L | 59/222 (27%) | NS2 | NS2 | 2.53 (1.37, 4.68) | 0.003 |
| Creatinine >= 2 mg/dL | 16/222 (7%) | 2.97 (1.10, 8.01) | 0.032 | NS2 | NS2 |
| Cytogenetic Abnormalities | 96/222 (43%) | 2.81 (1.42, 5.55) | 0.003 | NS2 | NS2 |
| GEP High Risk | 41/222 (18%) | NS2 | NS2 | 3.32 (1.74, 6.33) | <.001 |
| GEP IFN >= 11 | 53/222 (24%) | 2.60 (1.32, 5.11) | 0.006 | 2.07 (1.14, 3.77) | 0.017 |
| GEP Centrosome Index >= 3 | 84/222 (38%) | 3.85 (1.93, 7.69) | <.001 | NS2 | NS2 |
| GEP Poly PC Score >= 13 | 7/222 (3%) | 6.32 (1.29, 30.92) | 0.023 | NS2 | NS2 |

HR - Hazard Ratio, 95% CI - 95% Confidence Interval, P-value from Wald Chi-Square Test in Cox Regression
NS2 - Multivariate results not statistically significant at 0.05 level. All univariate p-values reported regardless of significance.
Multivariate model uses stepwise selection with entry level 0.1 and variable remains if meets the 0.05 level.
A multivariate p-value greater than 0.05 indicates variable forced into model with significant variables chosen using stepwise selection.

Prognostic and Predictive Impact of Genetic Lesions of Individual Chromosomes

Figures 12A, 12B:
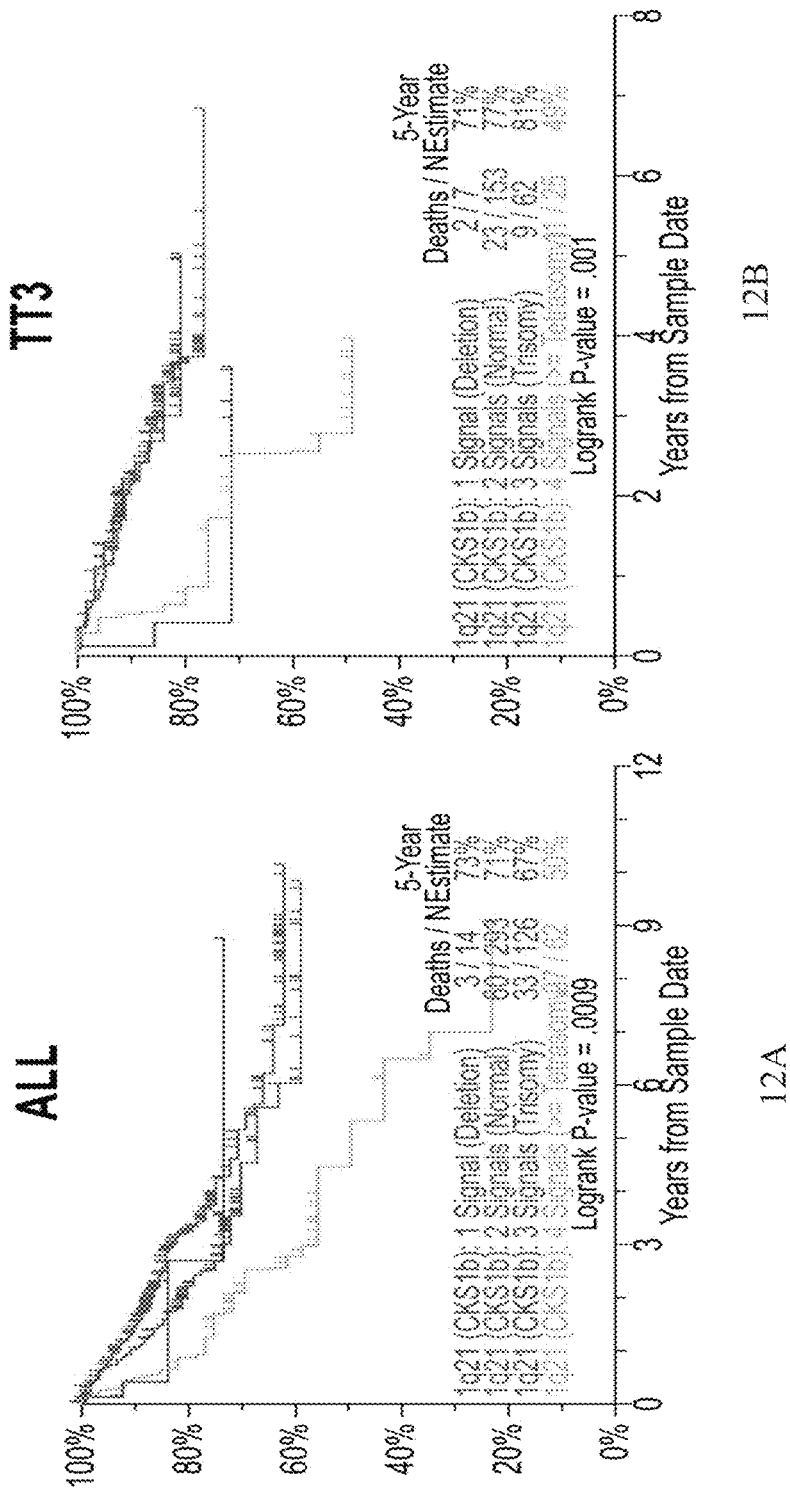
FIG. 12A-D show the Kaplan-Meier analysis of overall survival (OS) by chromosome 1q21 (CKS1b) abnormalities.
Figures 12C, 12D:
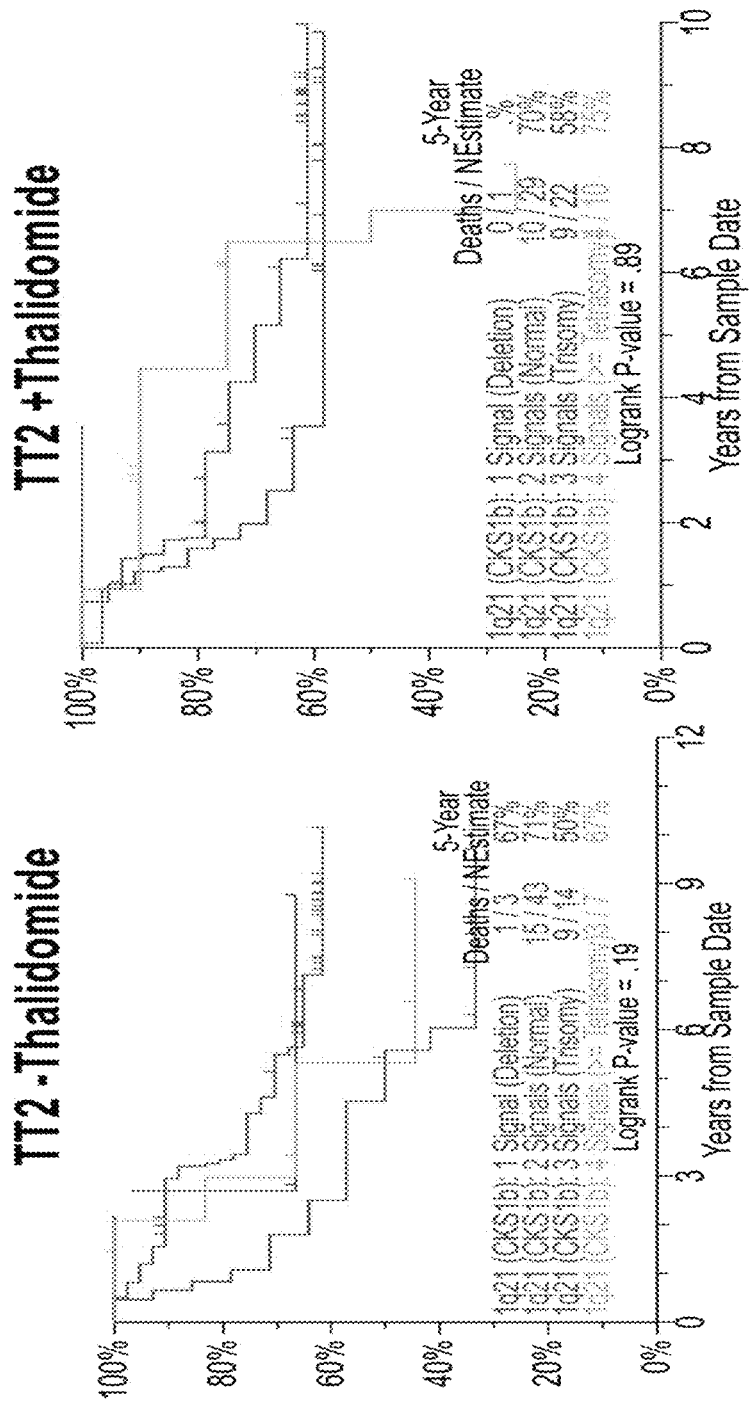
Figures 13A, 13B, 13C, 13D:
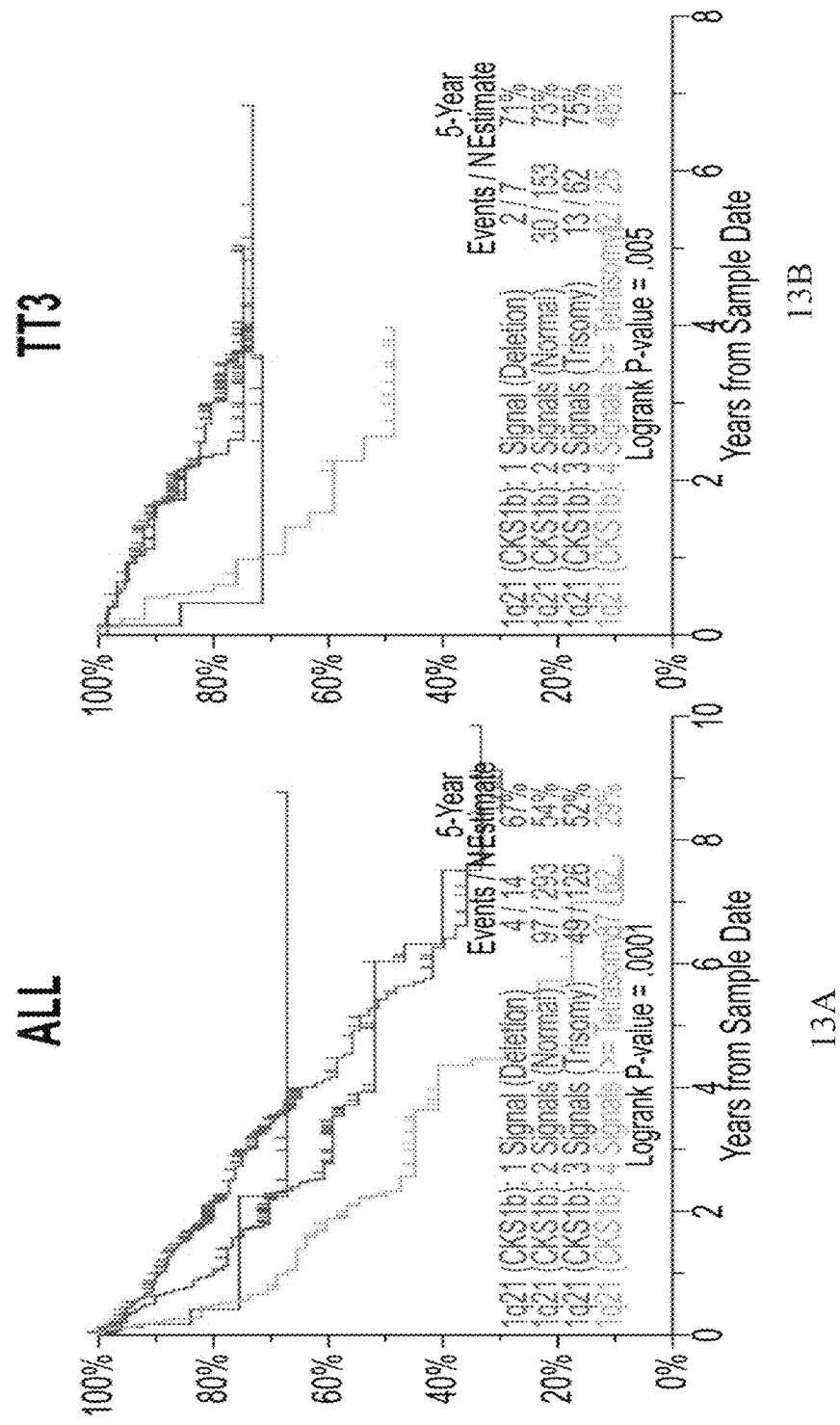
FIG. 13A-D show the Kaplan-Meier analysis of even free survival (EFS) by chromosome 1q21 (CSK1b) abnormalities.
Figures 13C, 13D:
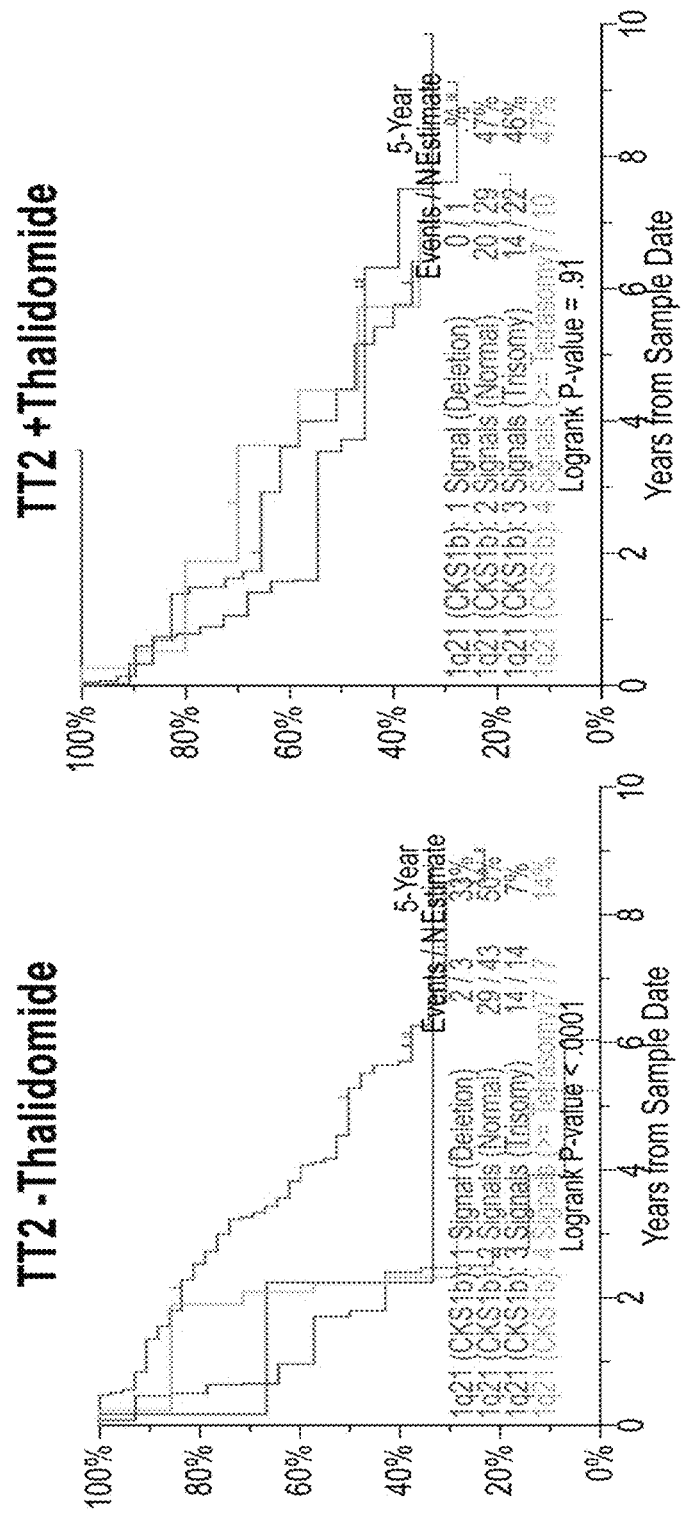
Figures 14A, 14B:
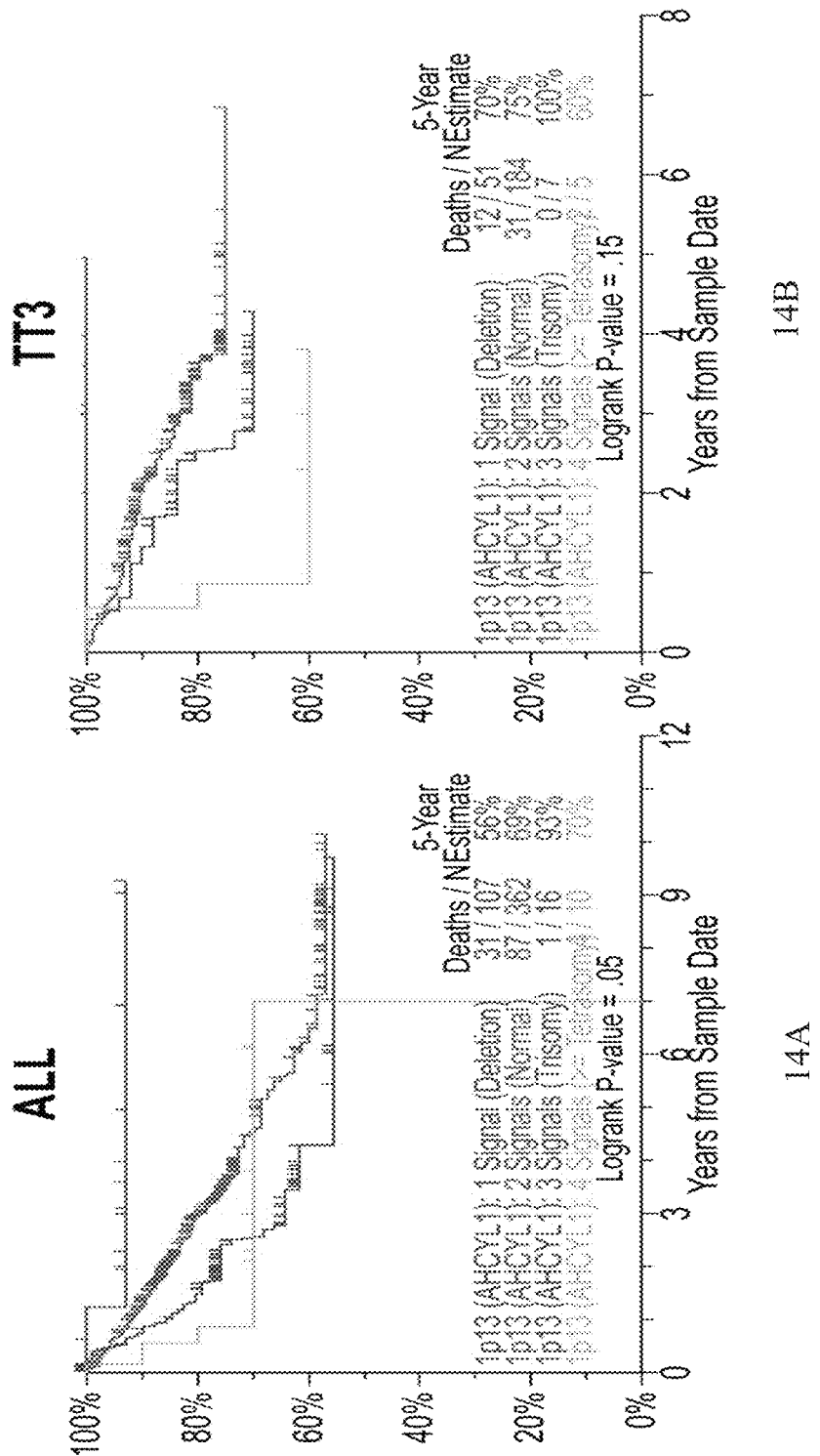
FIG. 14A-D show the Kaplan-Meier analysis of overall survival (OS) by chromosome 1p13 (AHCYL1) abnormalities.
Figures 14C, 14D:
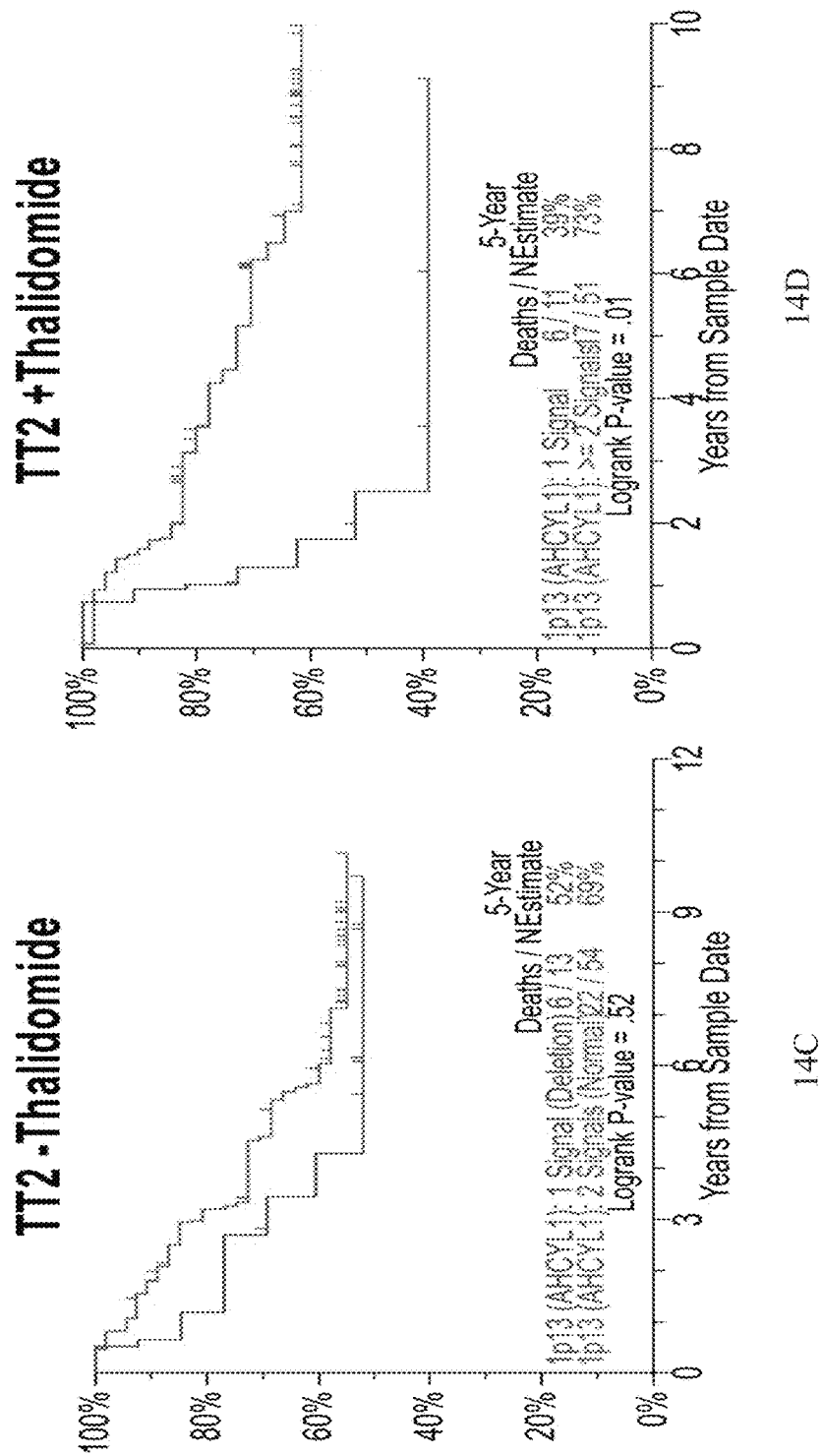
Figures 15A, 15B:
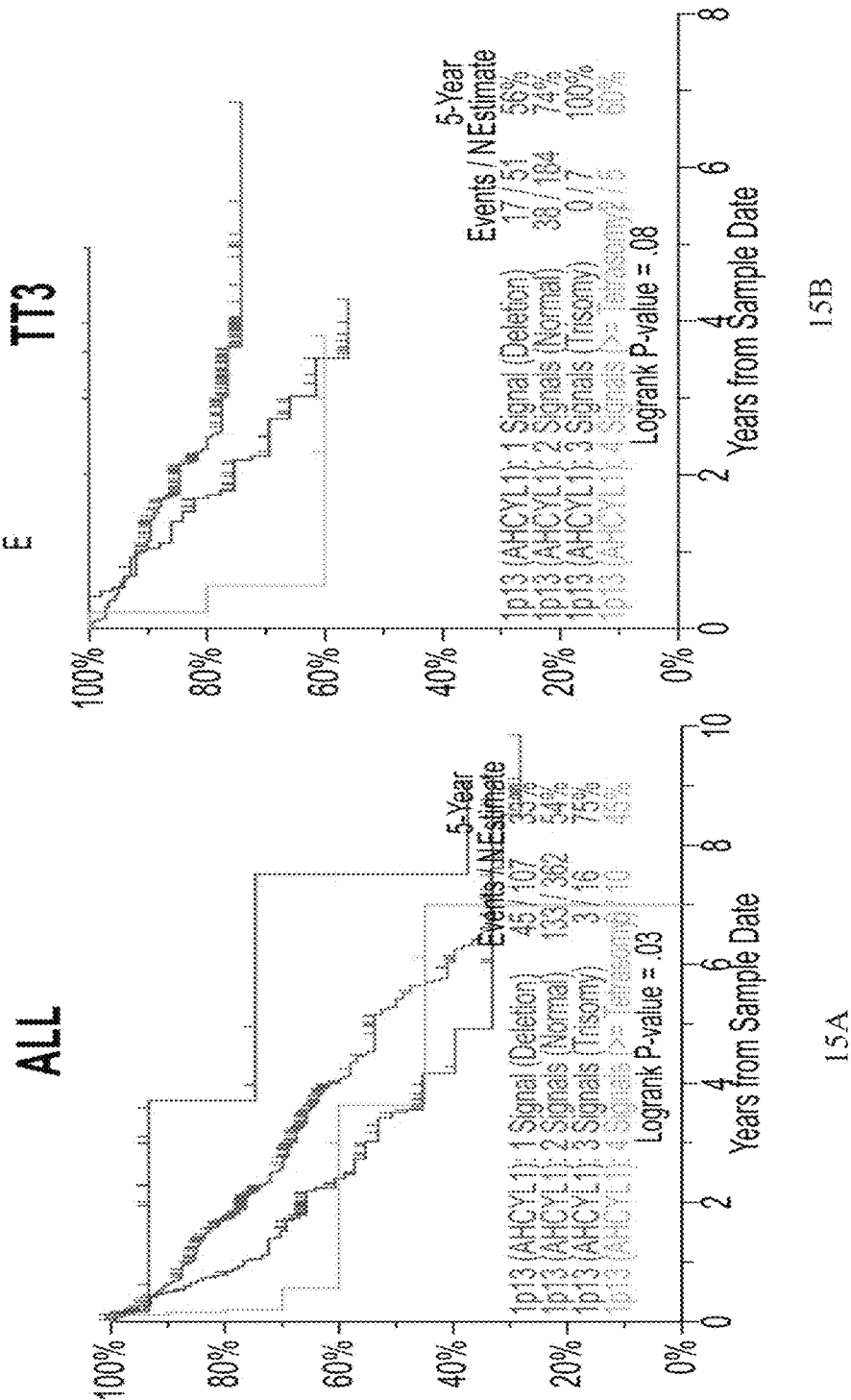
FIG. 15A-D show the Kaplan-Meier analysis of even free survival (EFS) by chromosome 1p13 (AHCYL1) abnormalities.
Figures 15C, 15D:
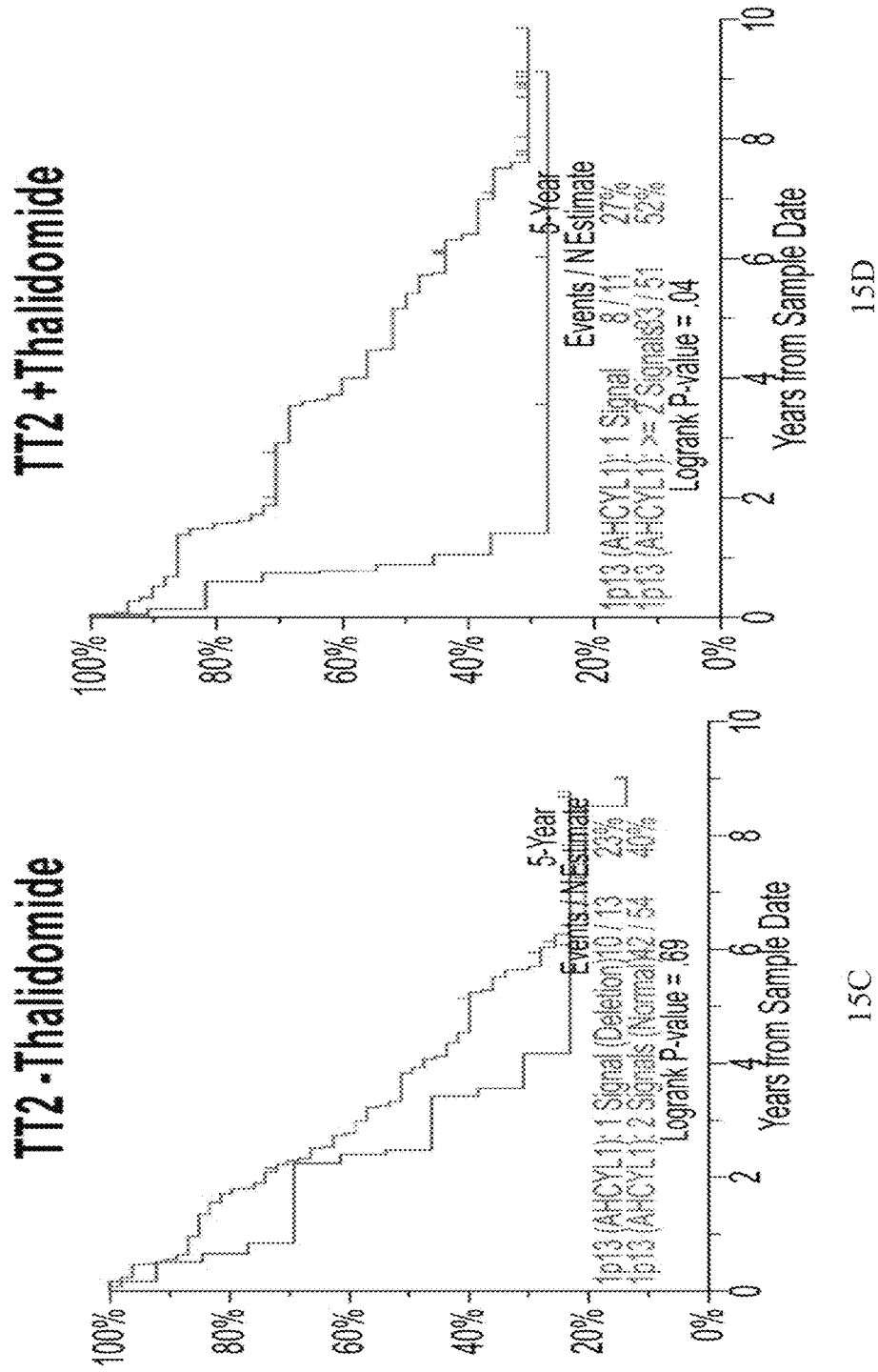
Figures 16A, 16B:
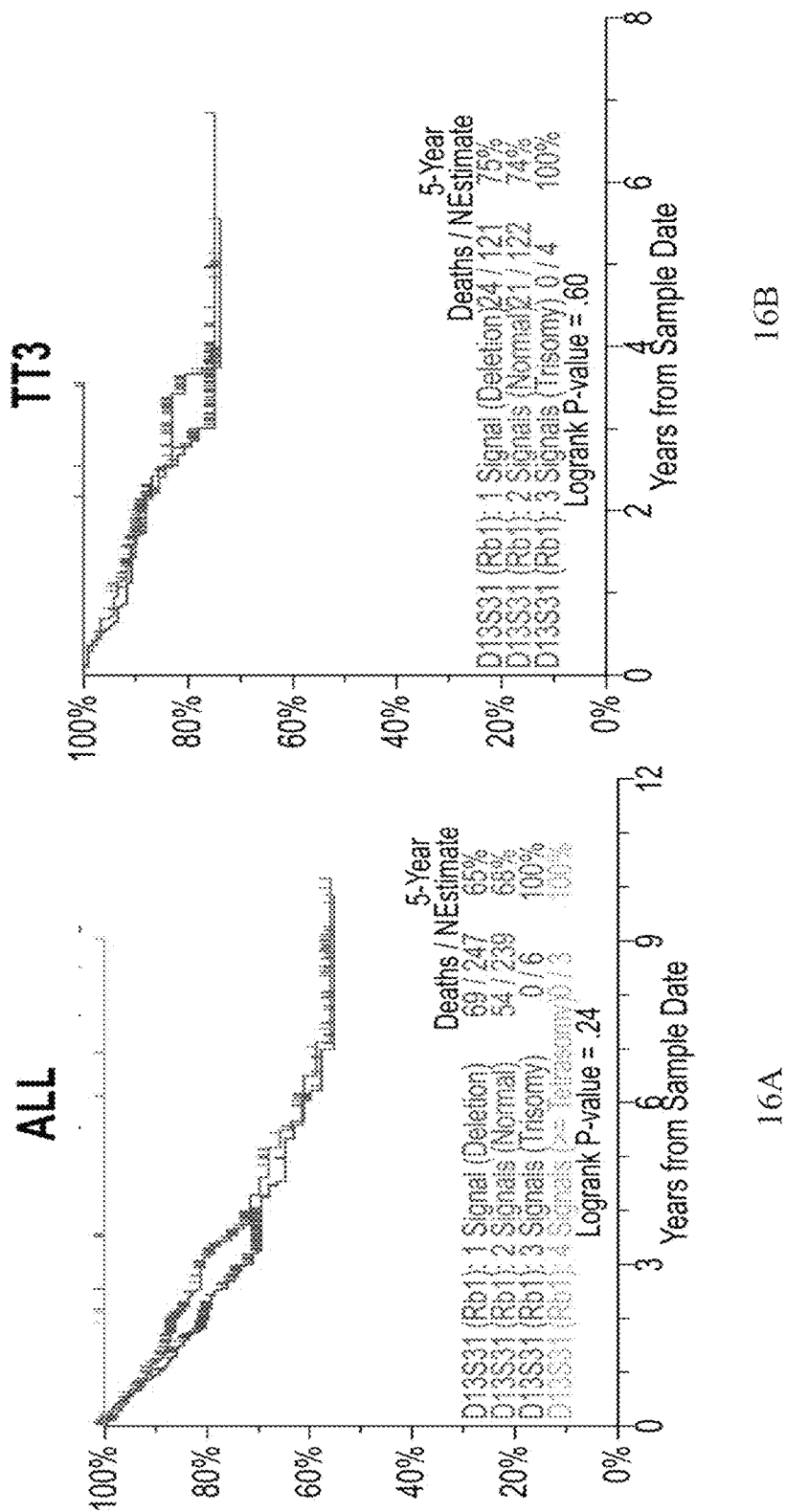
FIG. 16A-D show the Kaplan-Meier analysis of overall survival (OS) by chromosome 13q14 (Rb1) abnormalities.
Figures 16C, 16D:
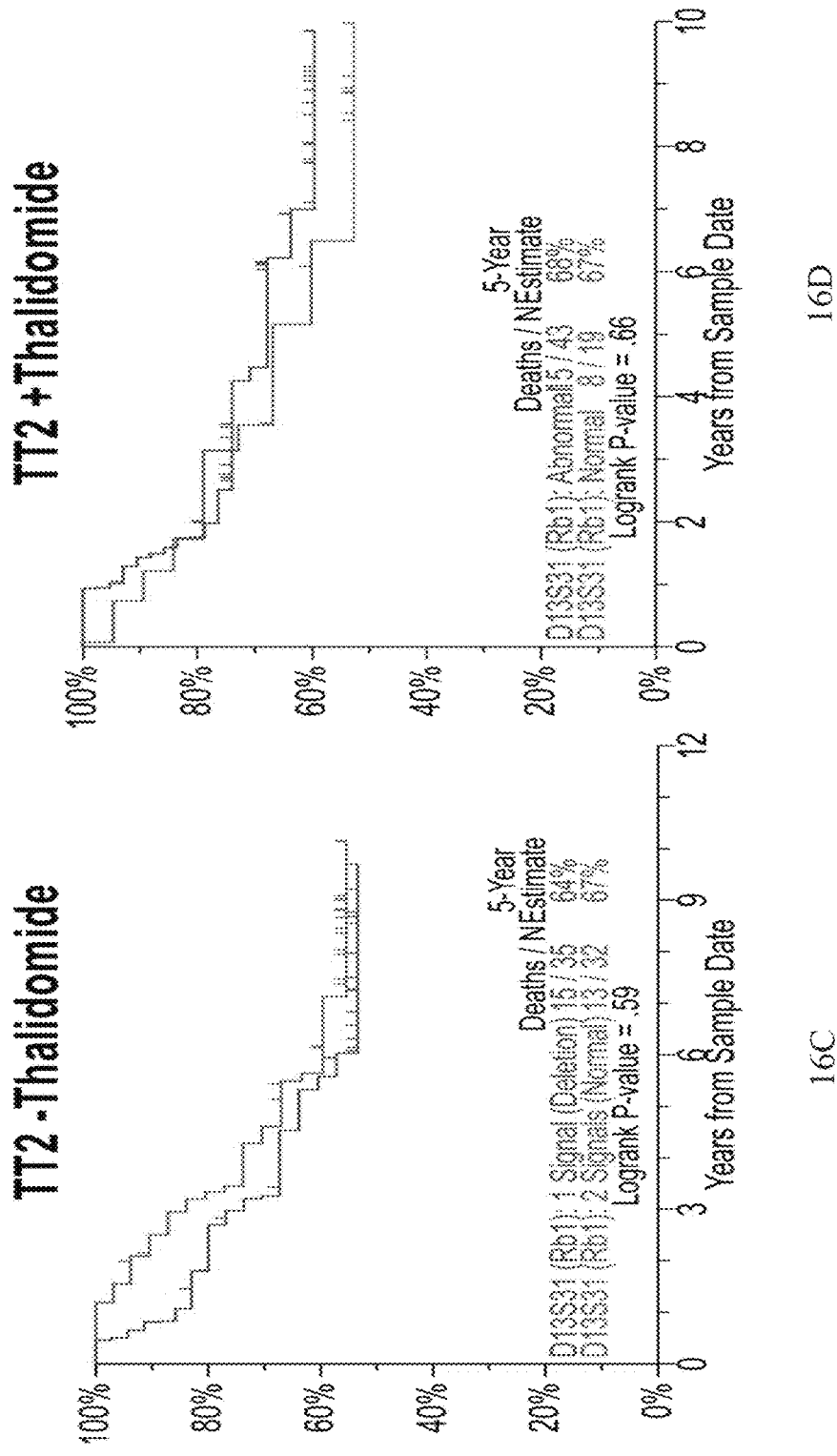
Figure 17A:
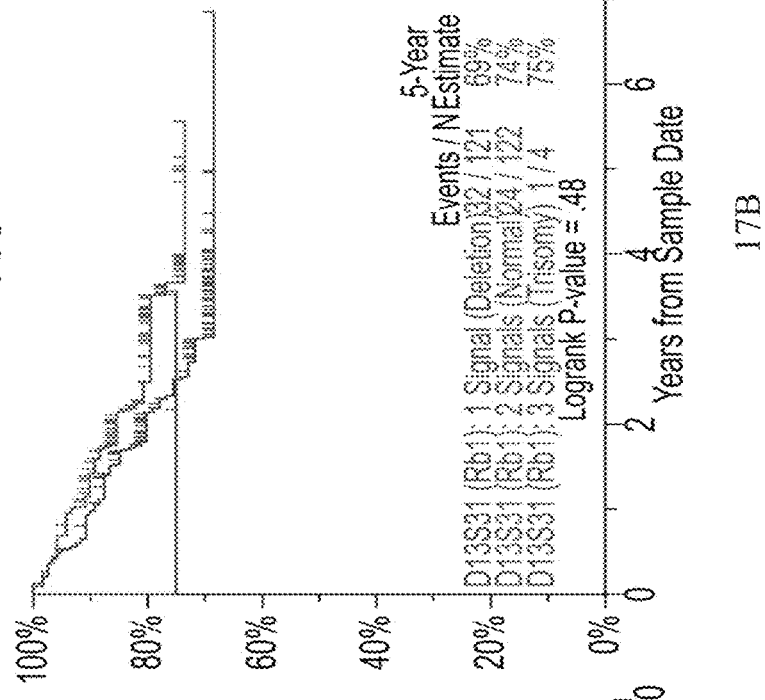
FIG. 17A-D show the Kaplan-Meier analysis of even free survival (EFS) by chromosome 13q14 (Rb1) abnormalities.
Figure 17B:
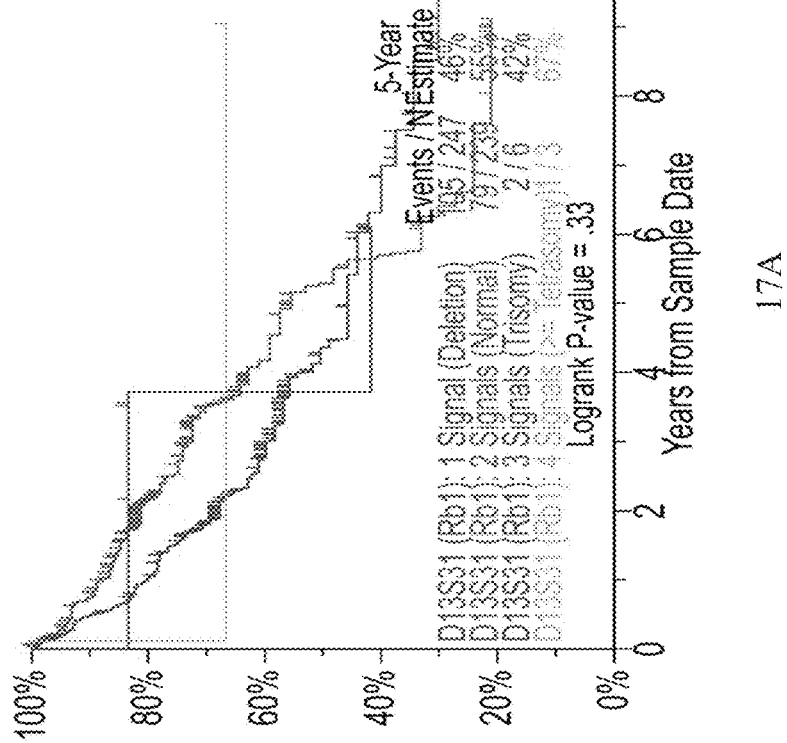
Figures 17C, 17D:
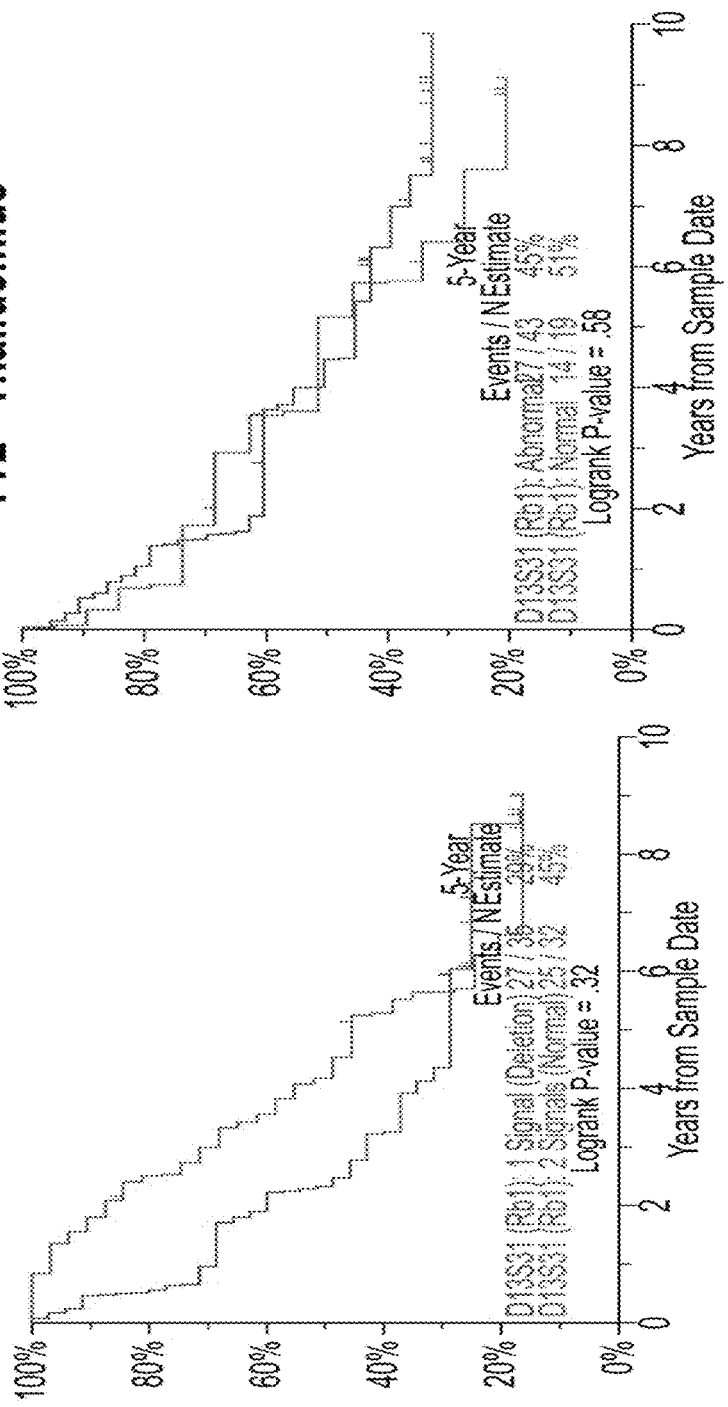
Figures 18A, 18B:
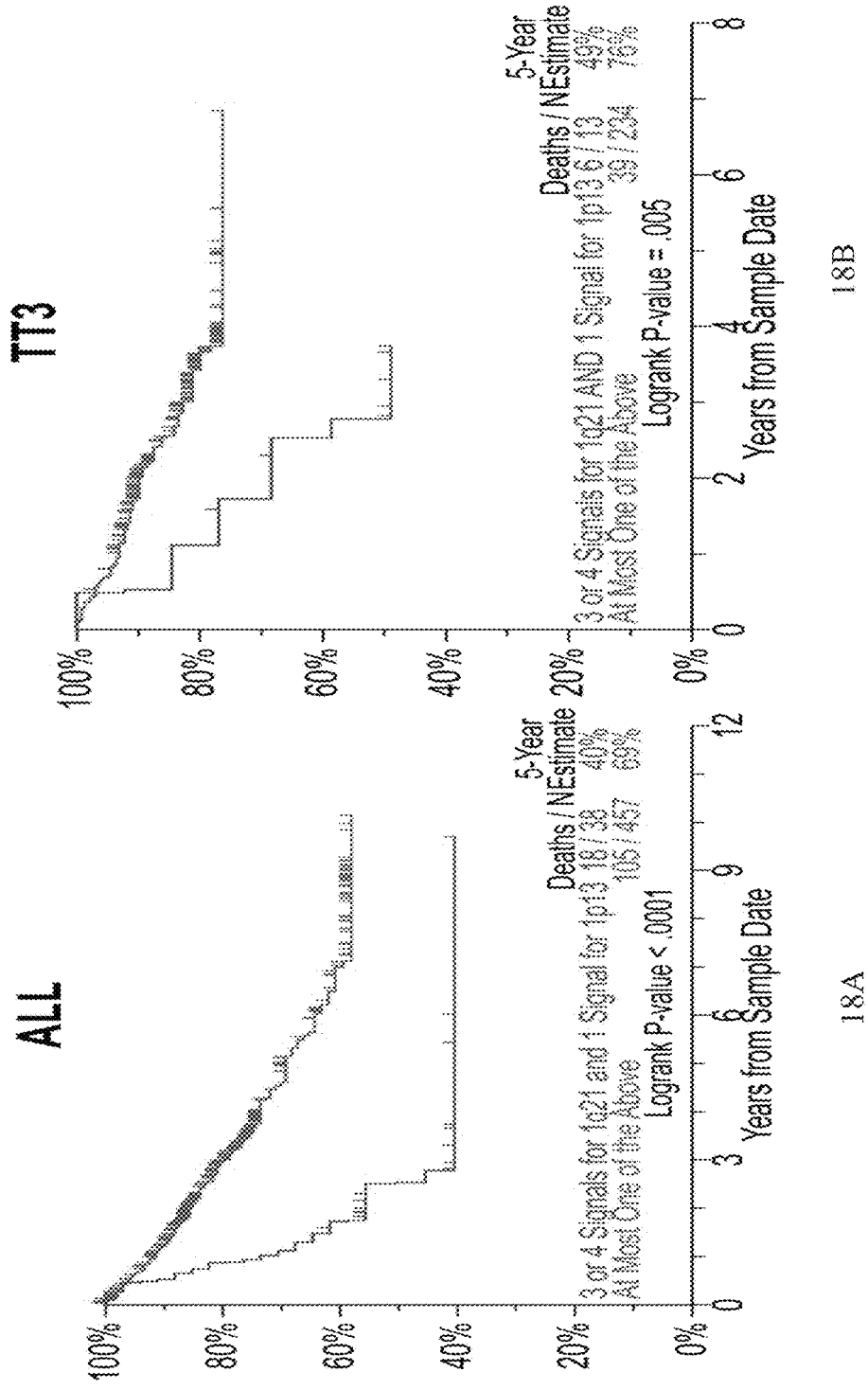
FIG. 18A-D show the Kaplan-Meier analysis of overall survival (OS) between 1q21 (CKS1b) and 1p13 (AHCYL1) abnormalities.
Figures 18C, 18D:
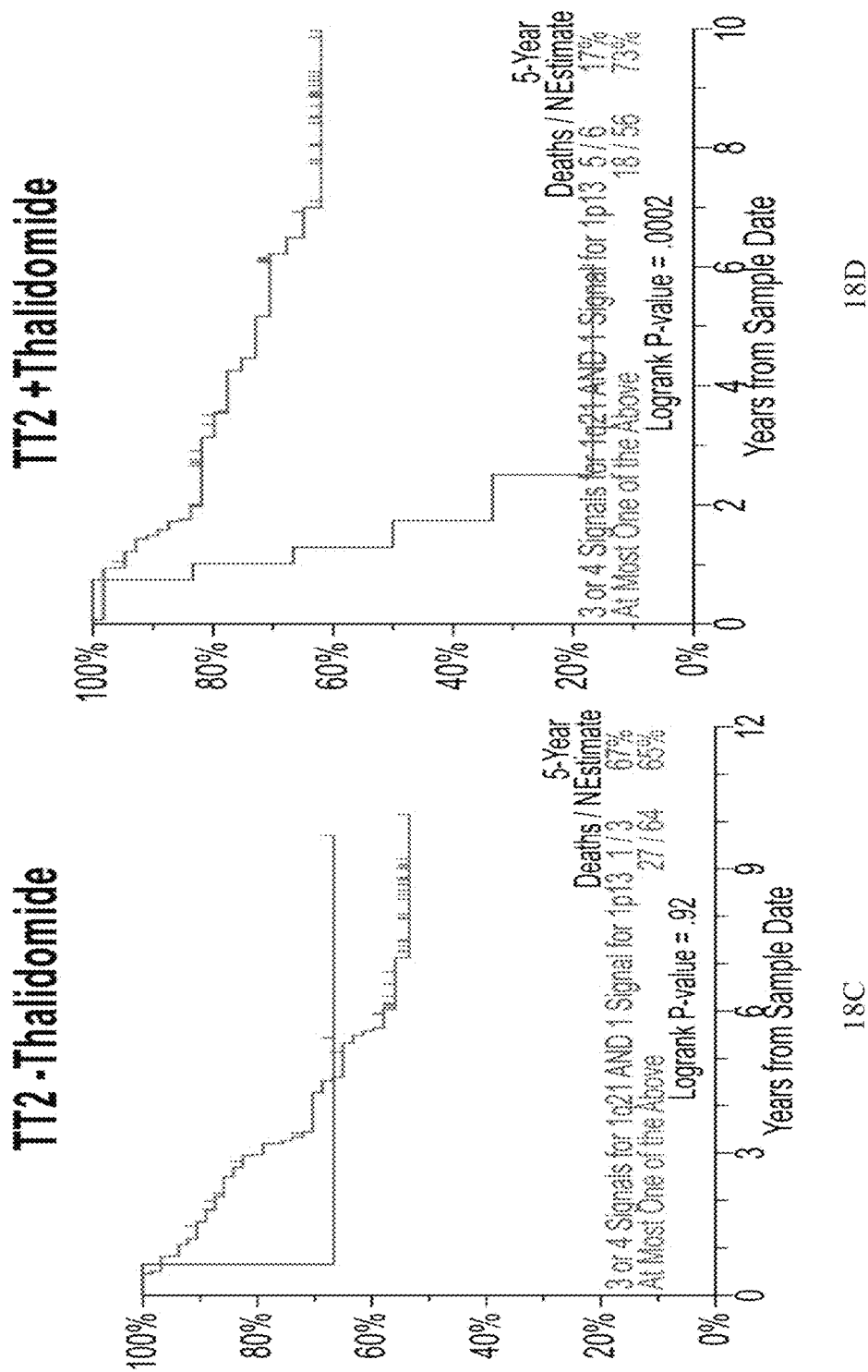
Figures 19A, 19B:
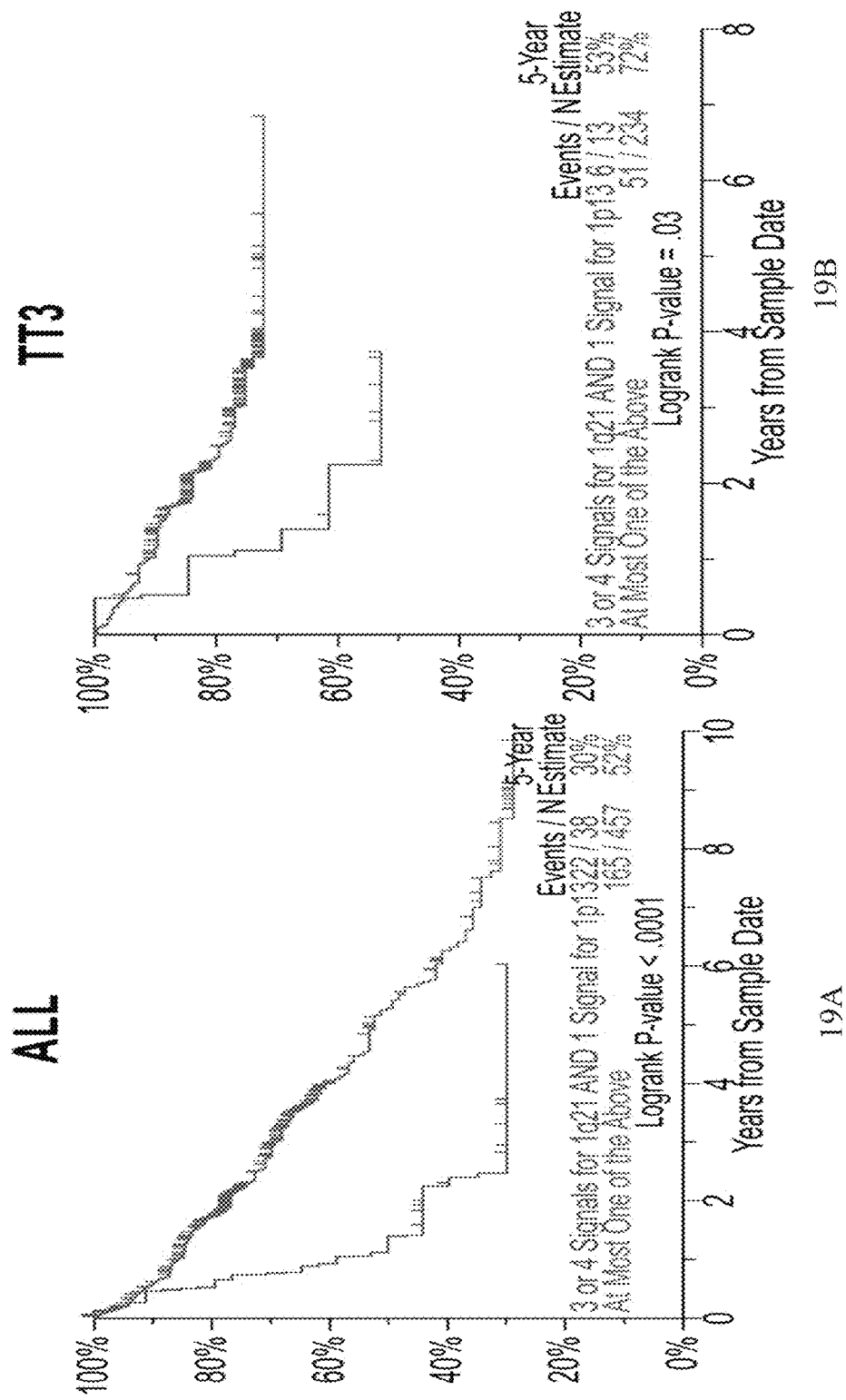
FIG. 19A-D show the Kaplan-Meier analysis of event free survival (EFS) between 1q21 (CKS1b) and 1p13 (AHCYL1) abnormalities.
Figures 19C, 19D:
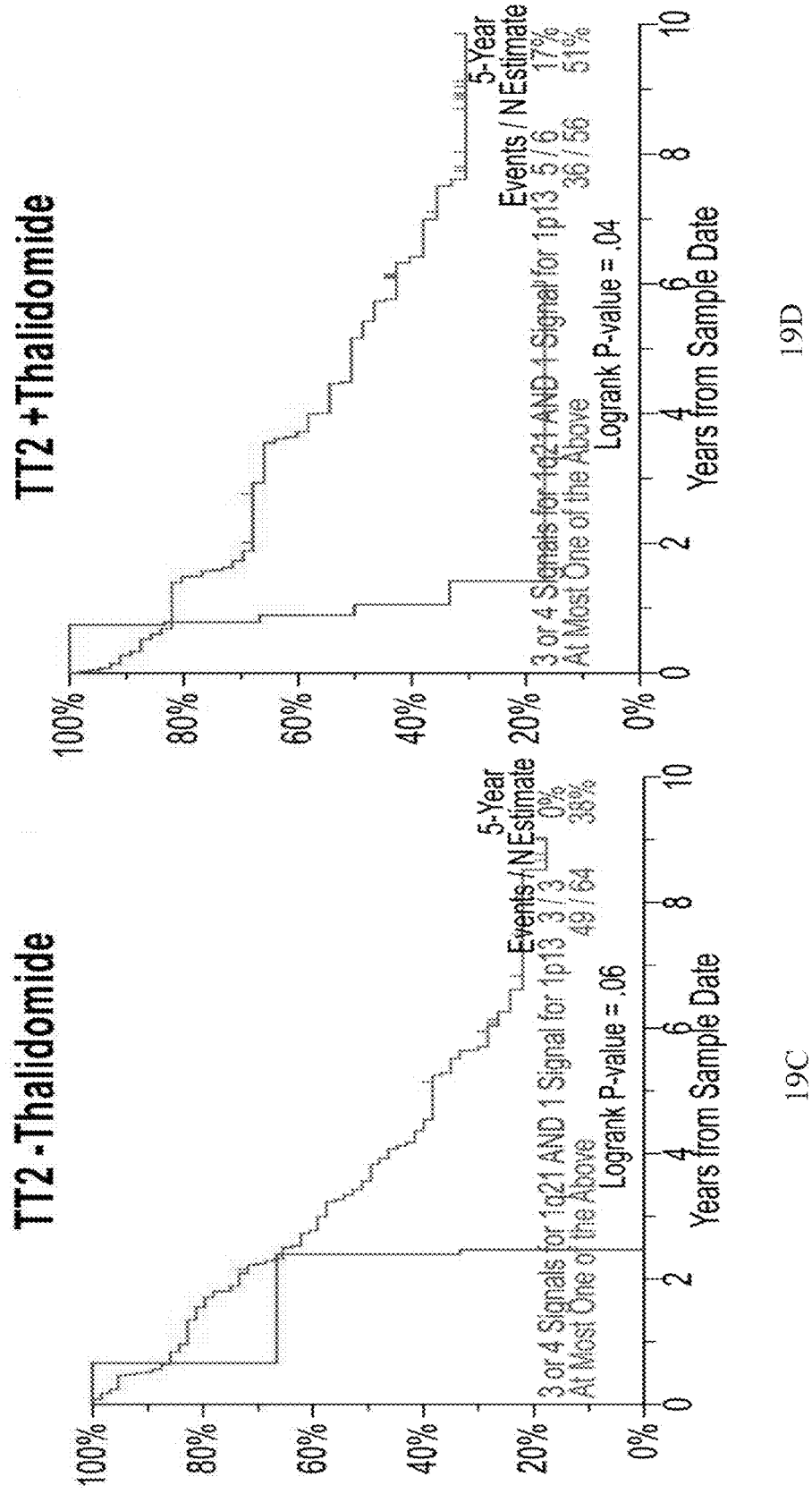
Figures 20A, 20B:
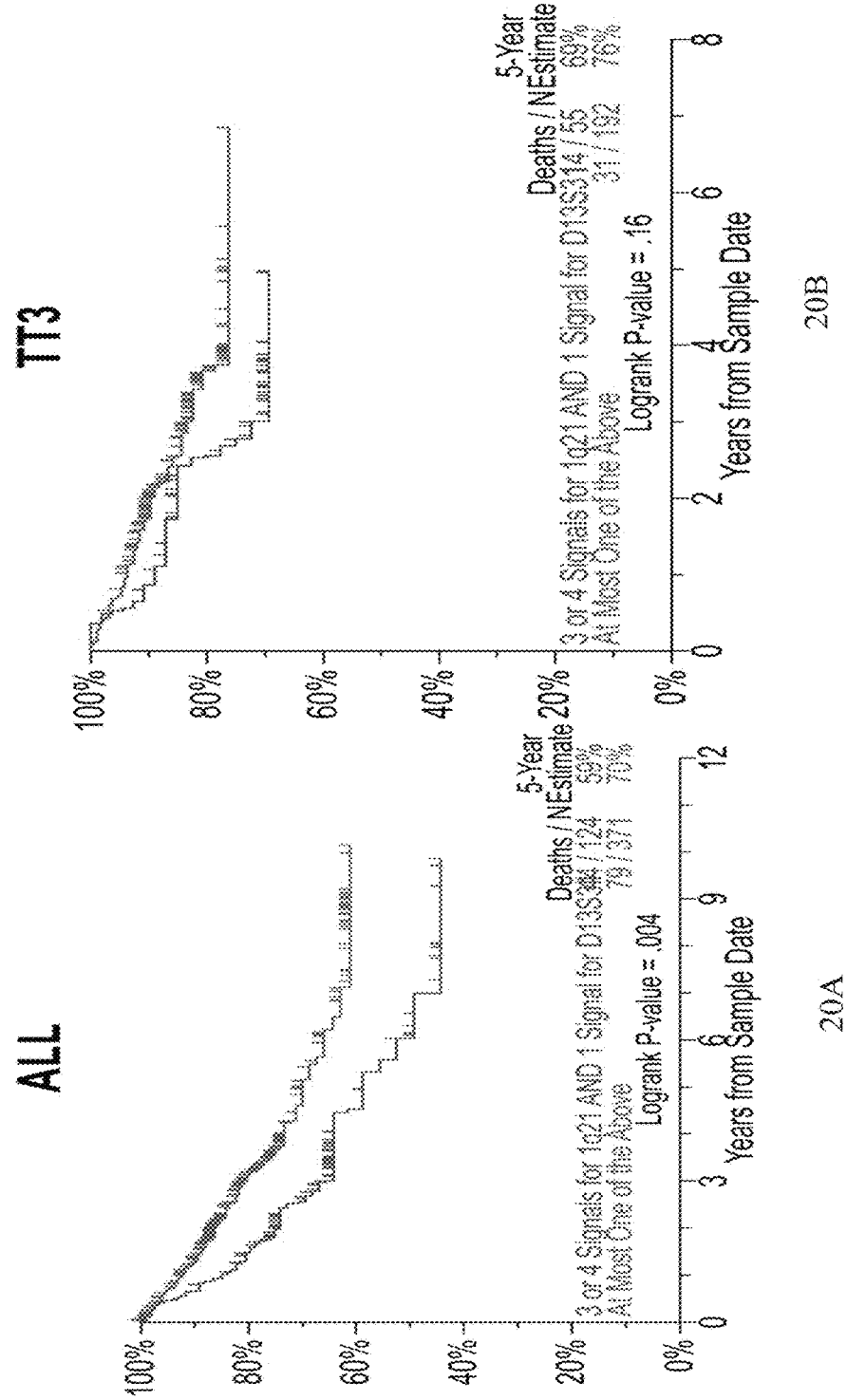
FIG. 20A-D show the Kaplan-Meier analysis of overall survival (OS) between 1q21 (CKS1b) and 13q14 (Rb1) abnormalities.
Figures 20C, 20D:
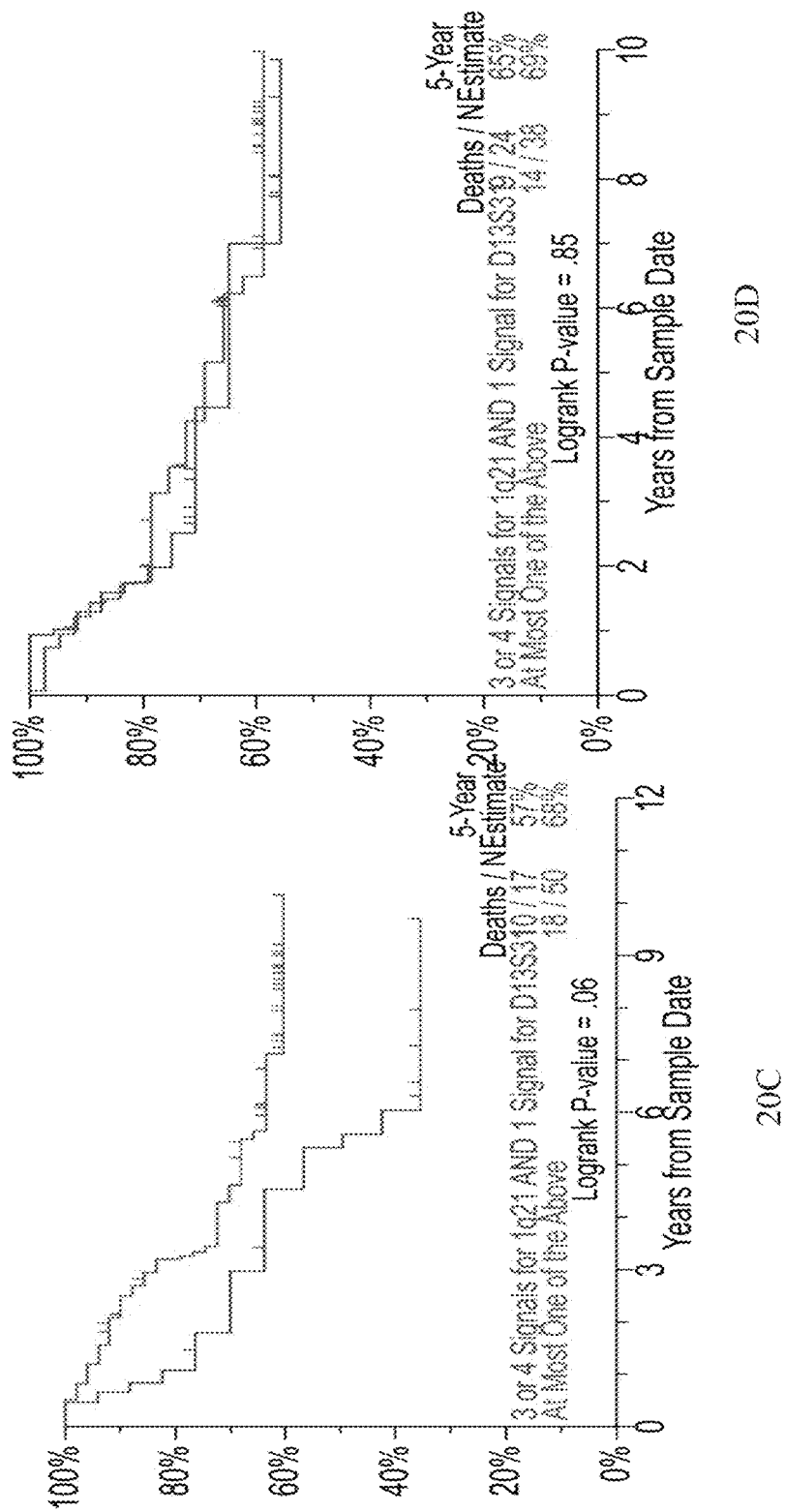
Figures 21A, 21B:
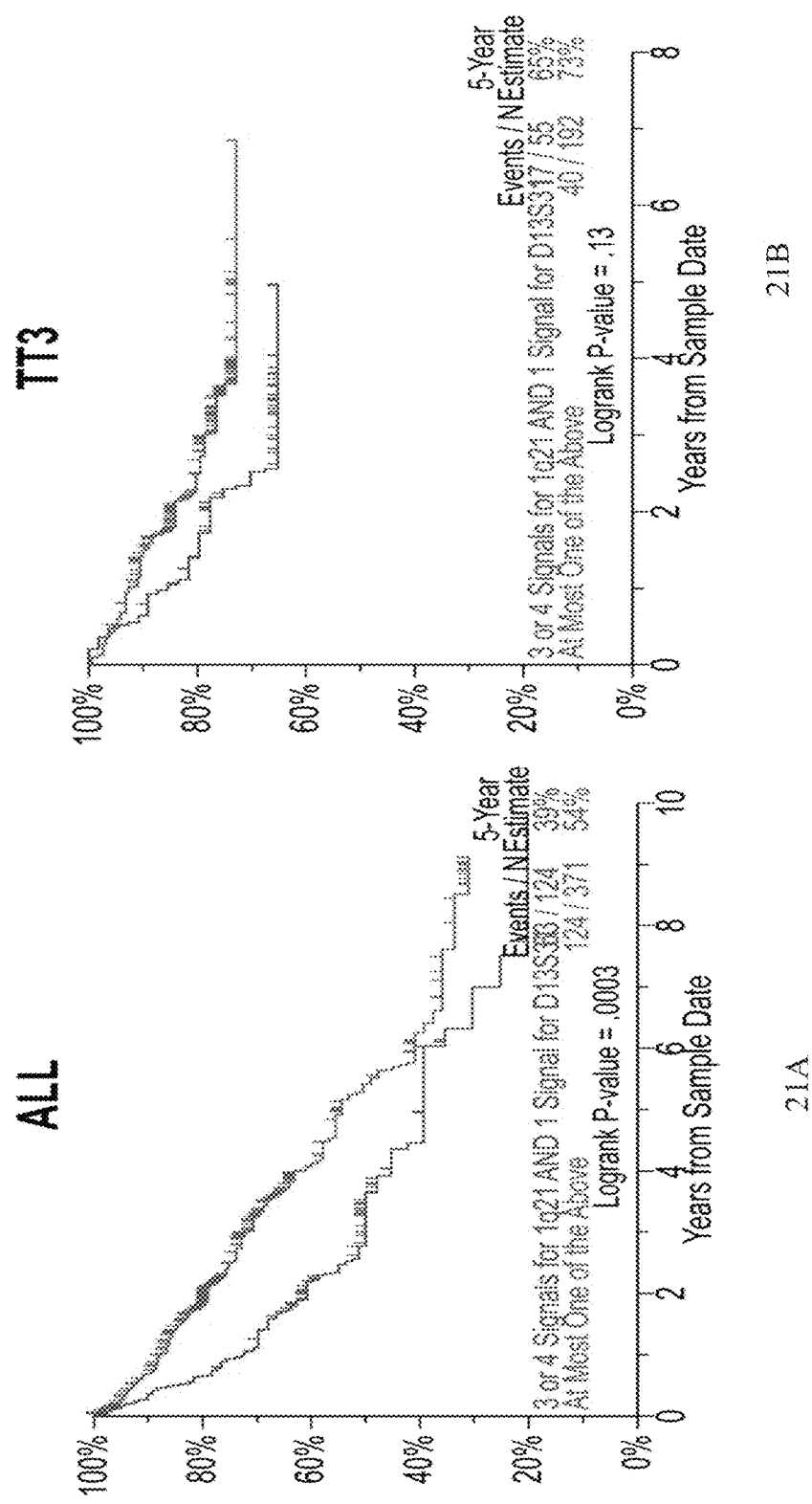
FIG. 21A-D show the Kaplan-Meier analysis of event free survival (EFS) between 1q21 (CKS1b) and 13q14 (Rb1) abnormalities.
Figures 21C, 21D:
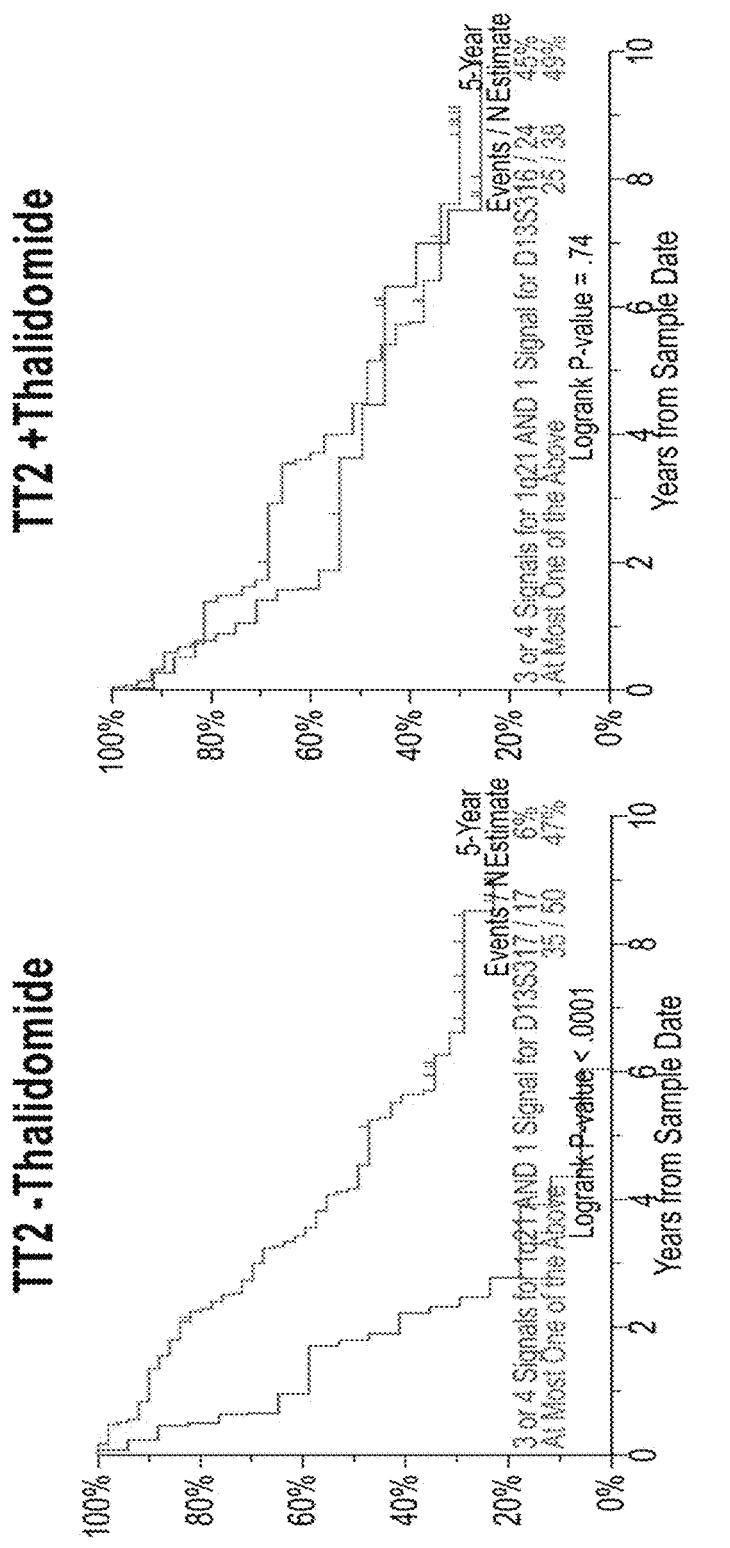
Figure 22A:
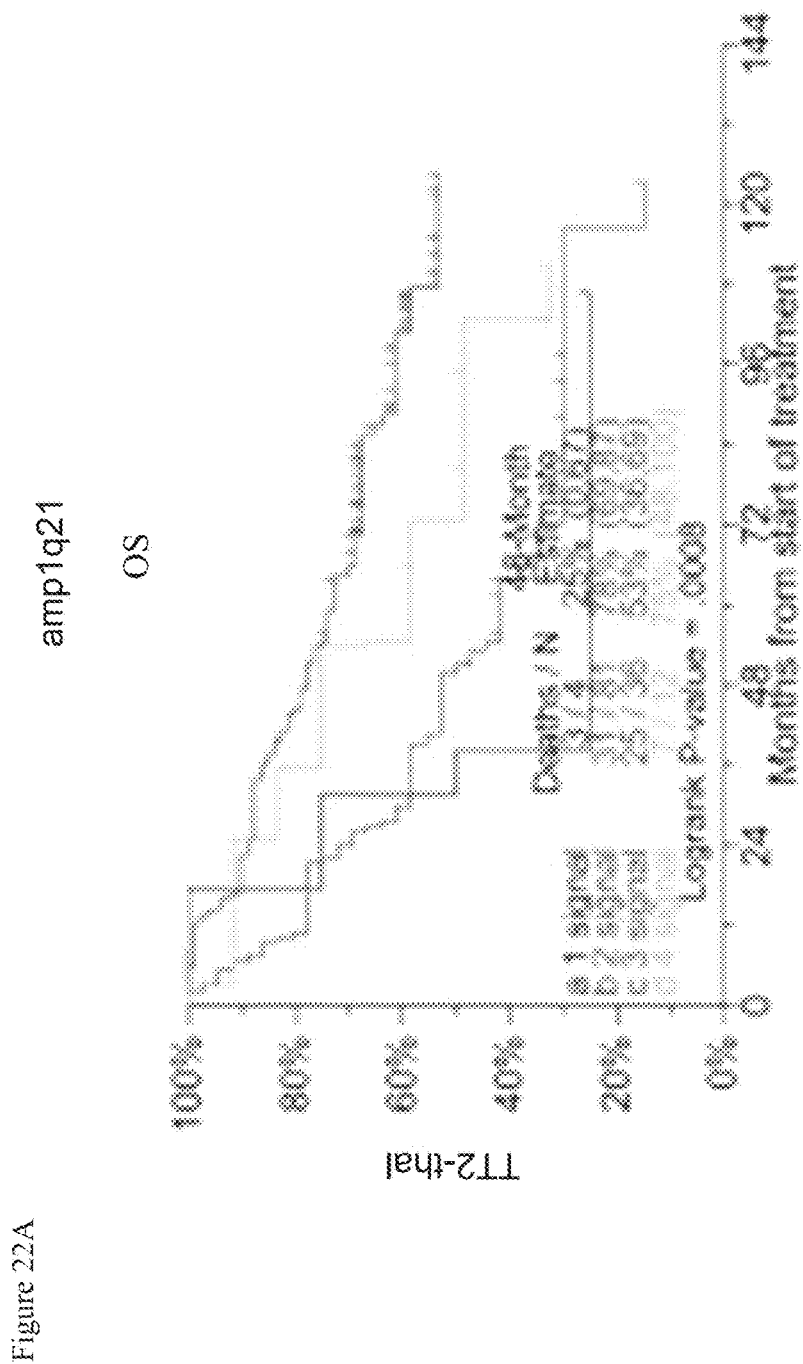
FIG. 22A-F show the Kaplan-Meier analysis of survival outcomes of 1q21 (CKS1b) abnormalities based on gene copy numbers of 1, 2, 3 or 4.
Figure 22B:
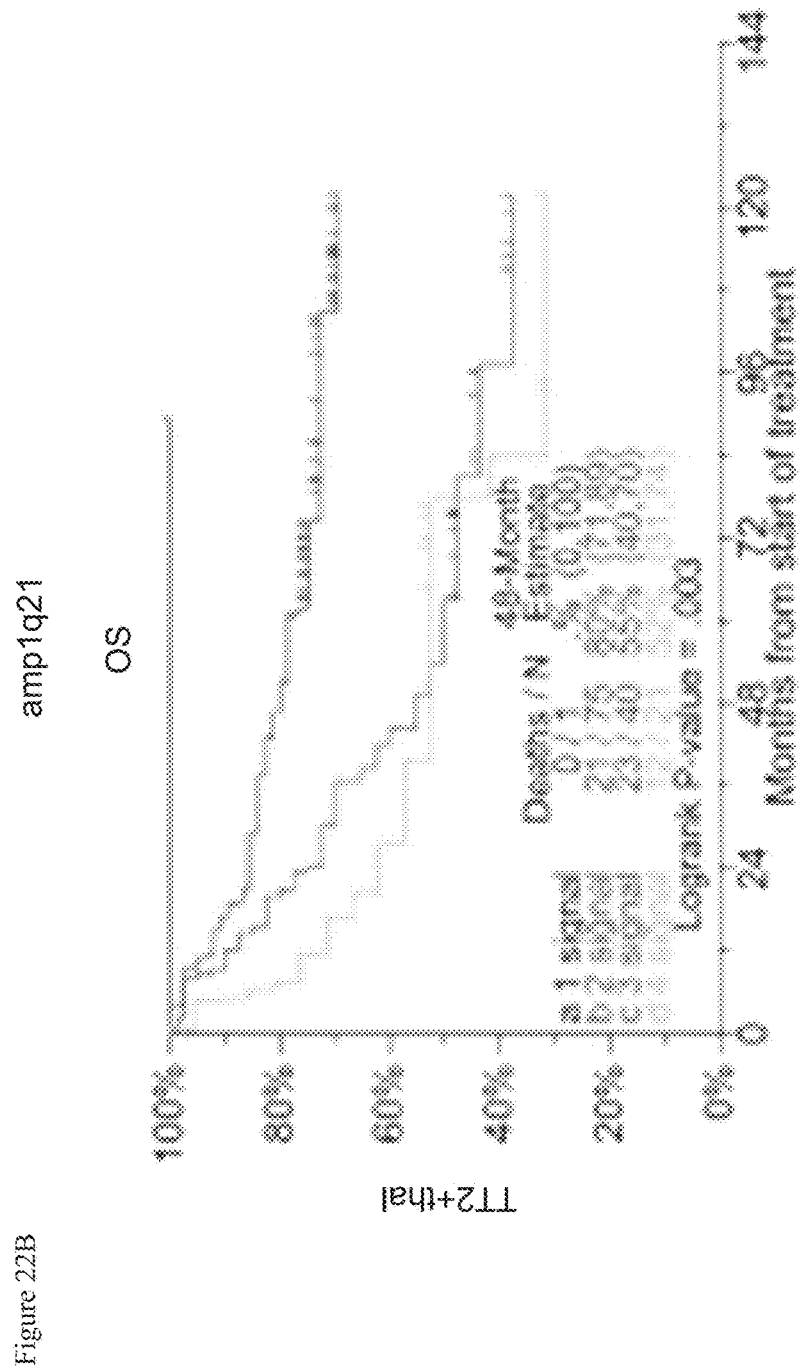
Figure 22C:
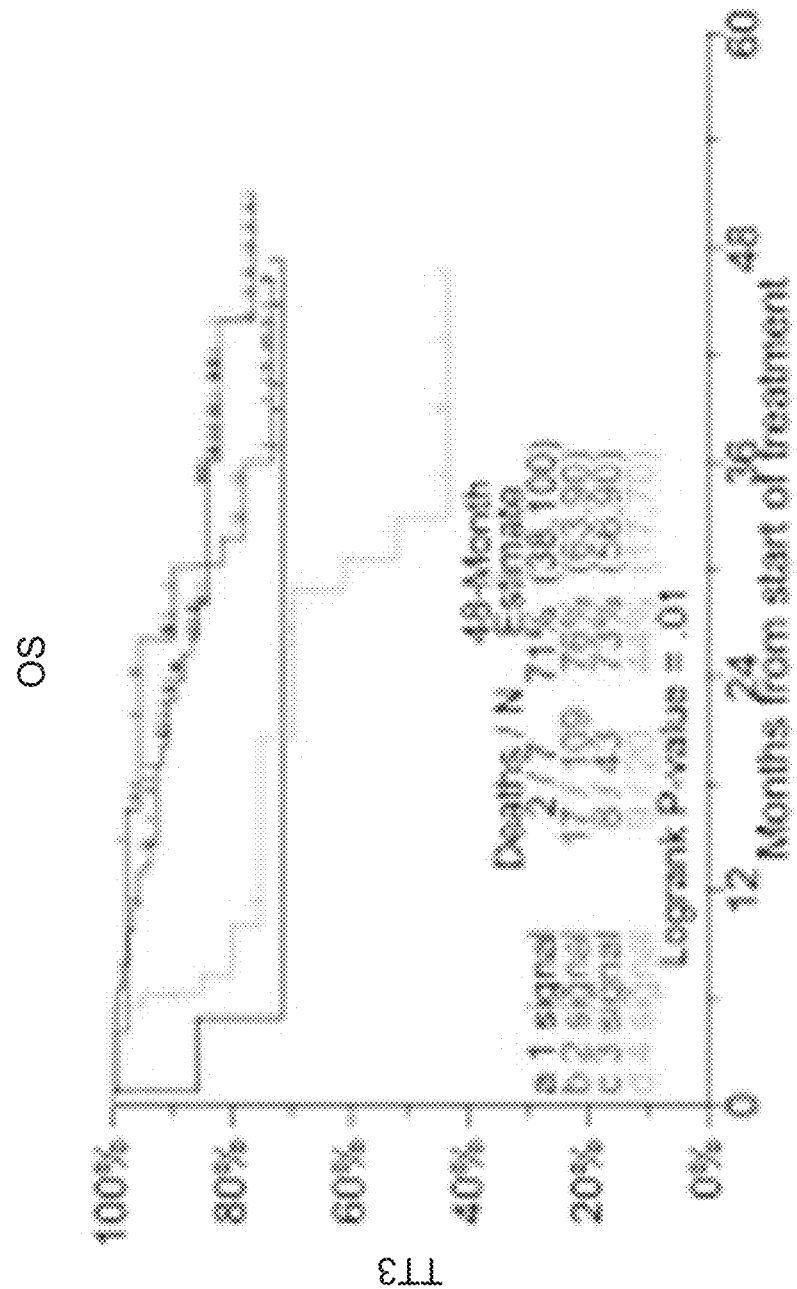
Figure 22D:
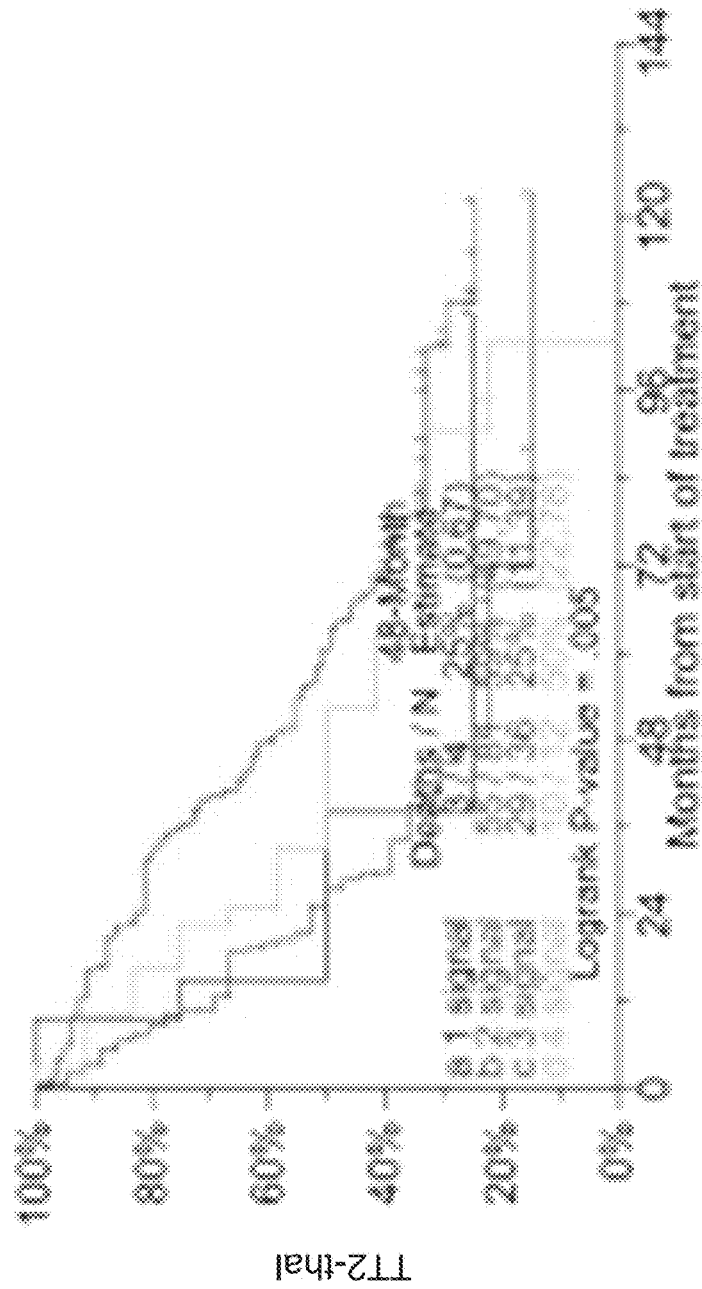
Figure 22E:
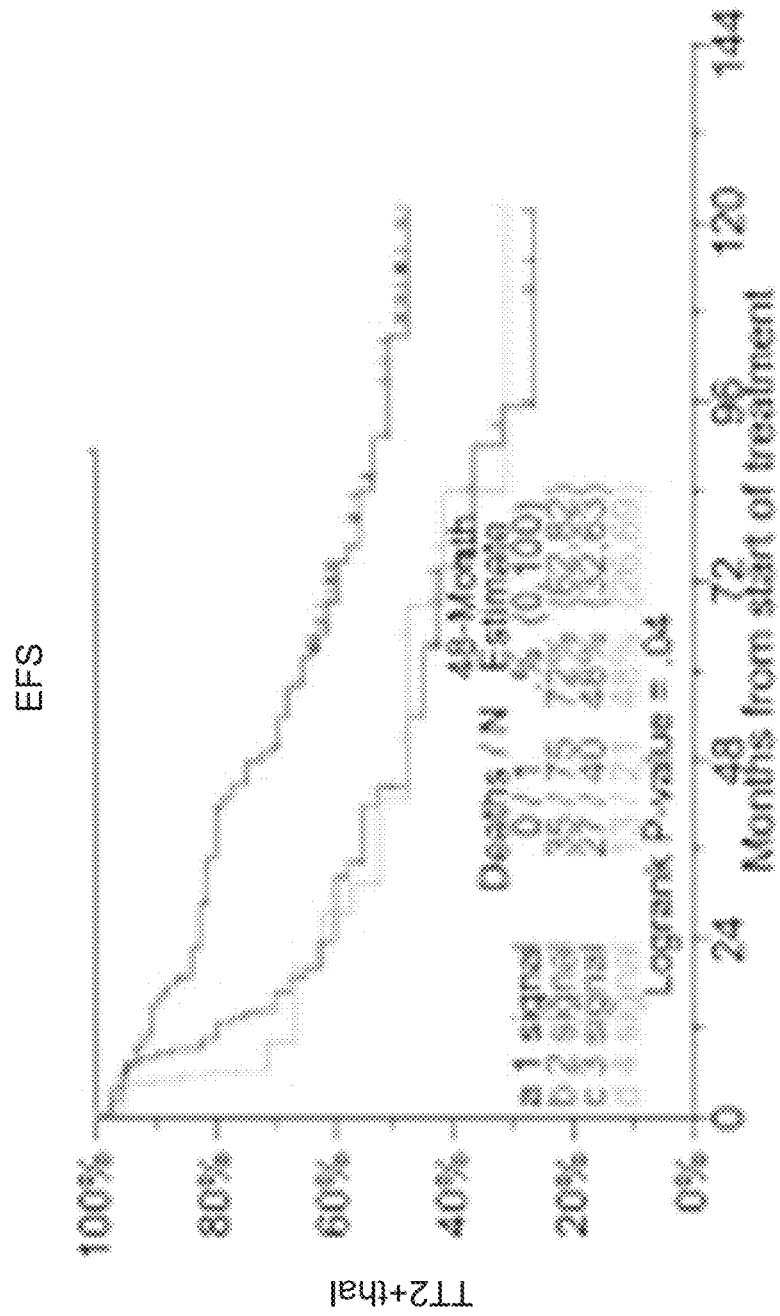
Figure 22F:
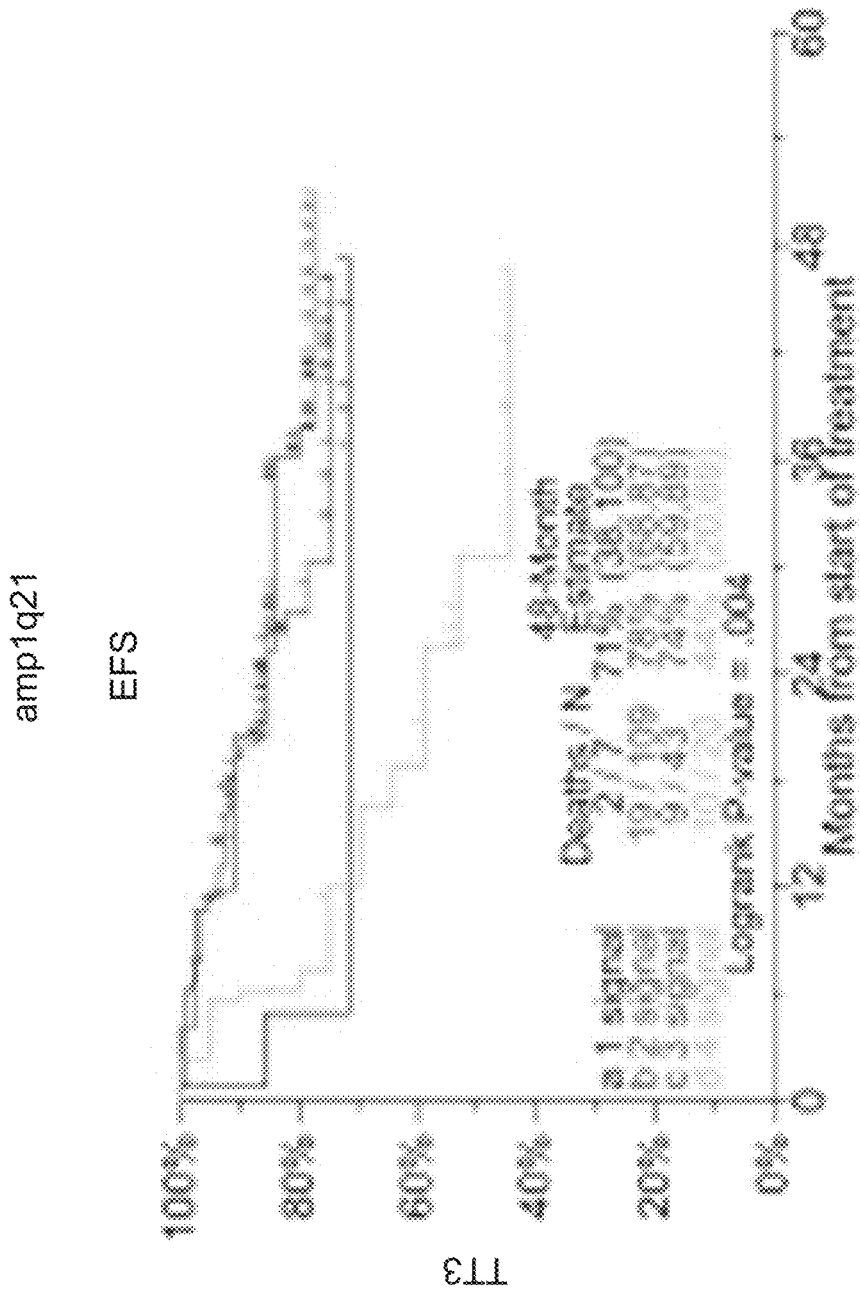
Figure 23A:
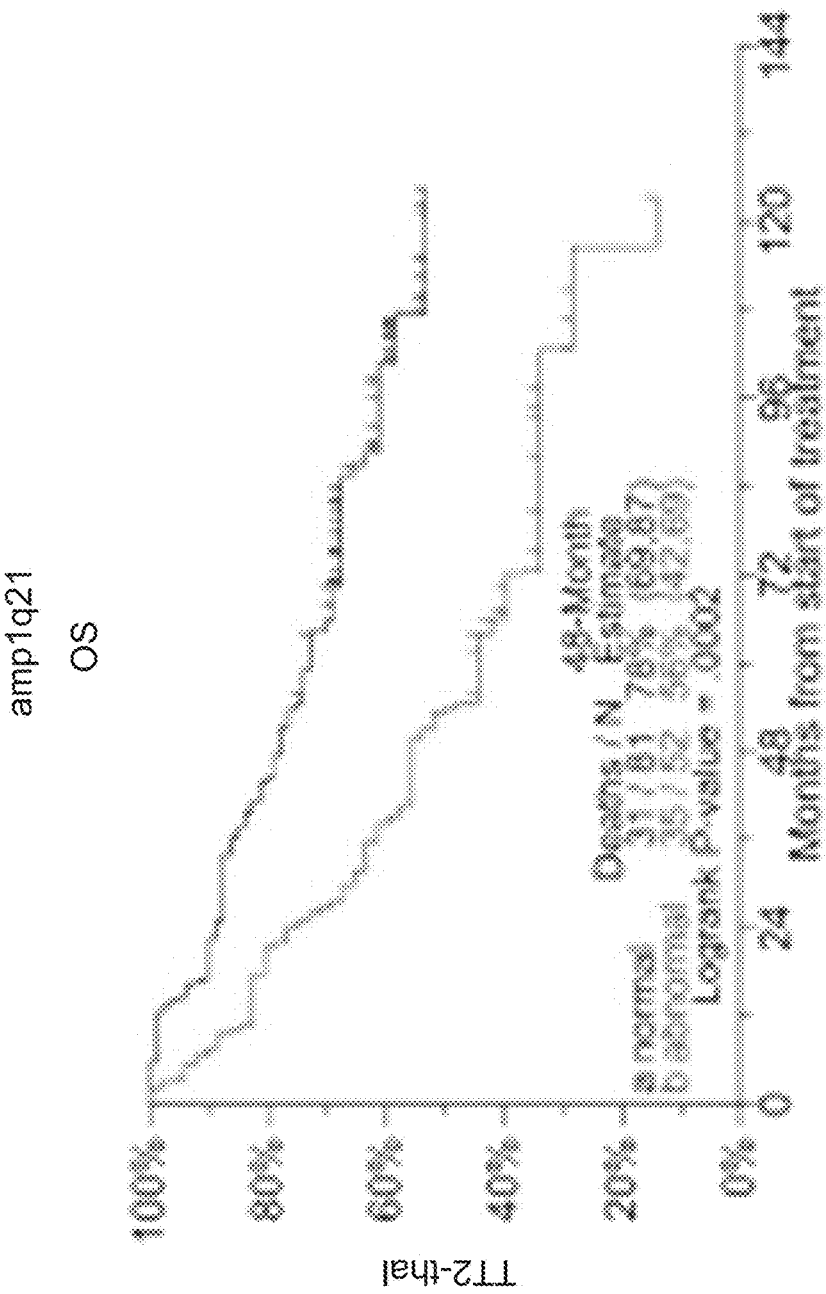
FIG. 23A-F show the Kaplan-Meier analysis of survival outcomes of 1q21 (CKS1b) abnormalities based on gene copy numbers of 2 and 1, 3 or greater.
Figure 23B:
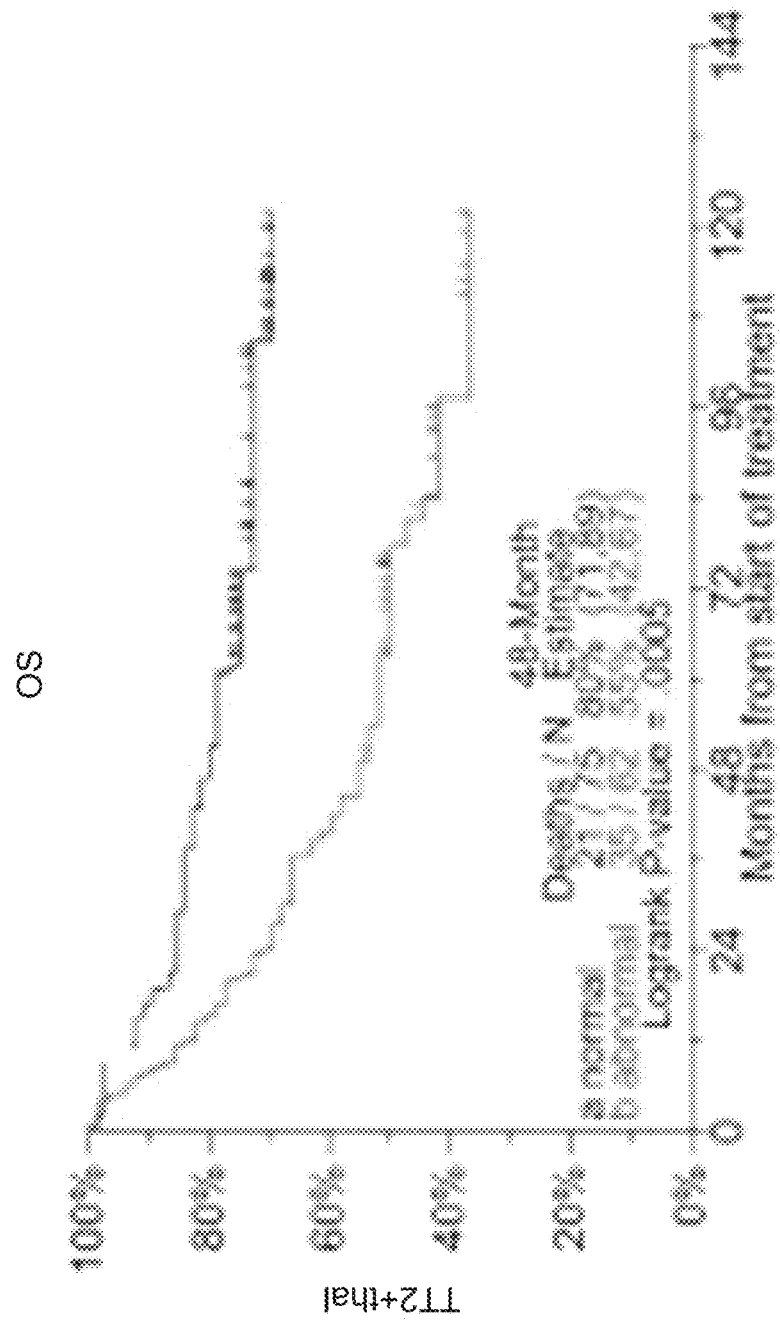
Figure 23C:
Figure 23D:
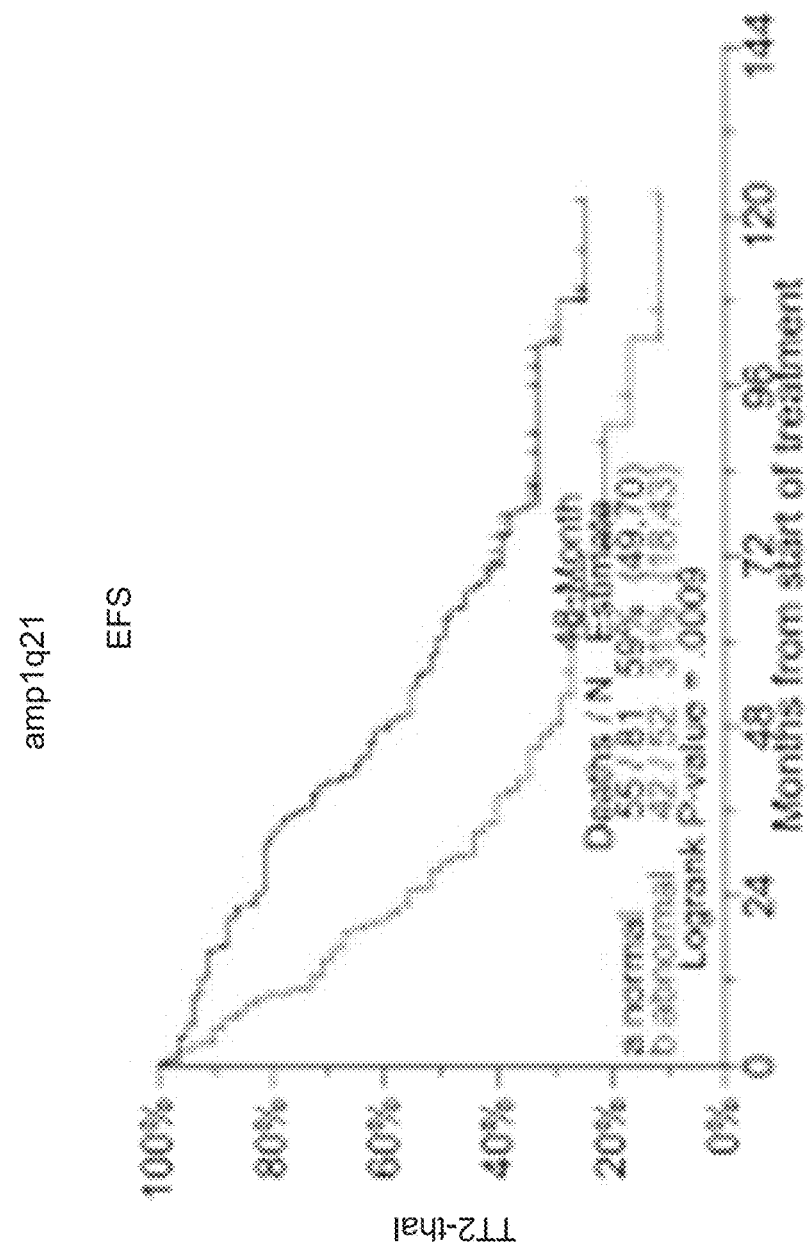
Figure 23E:
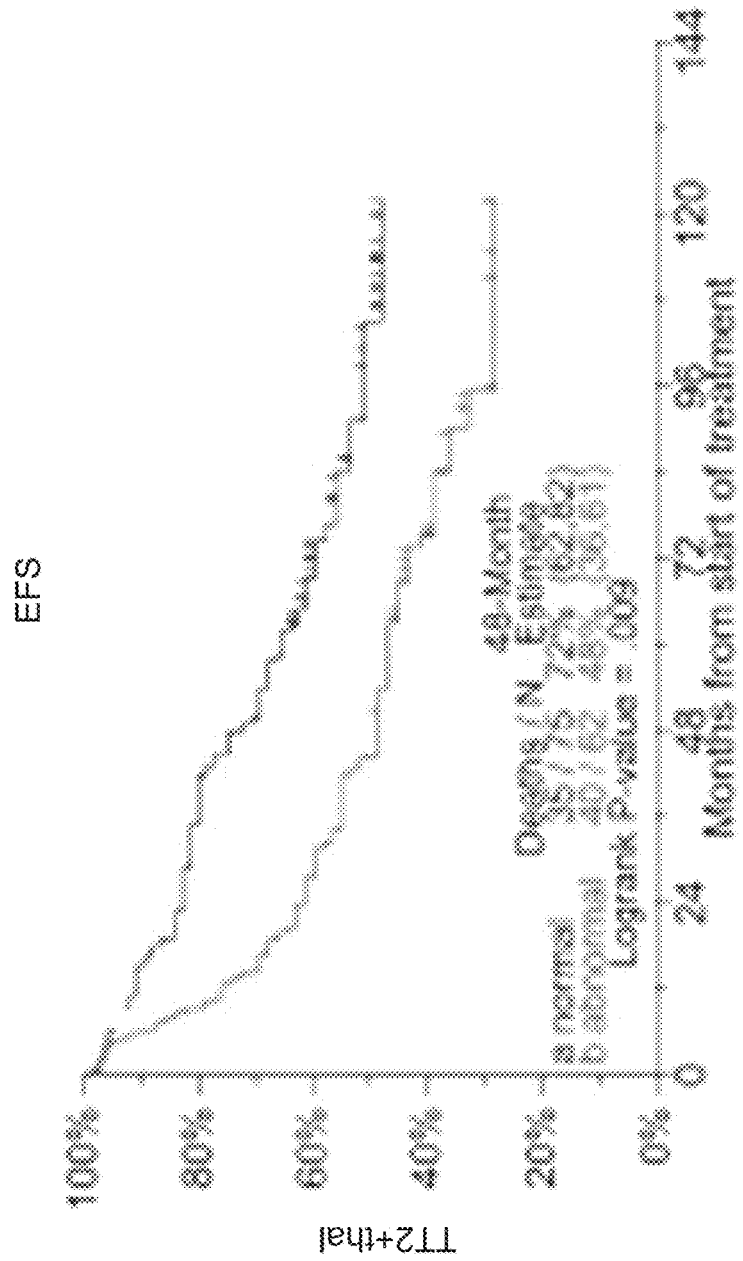
Figure 23F:
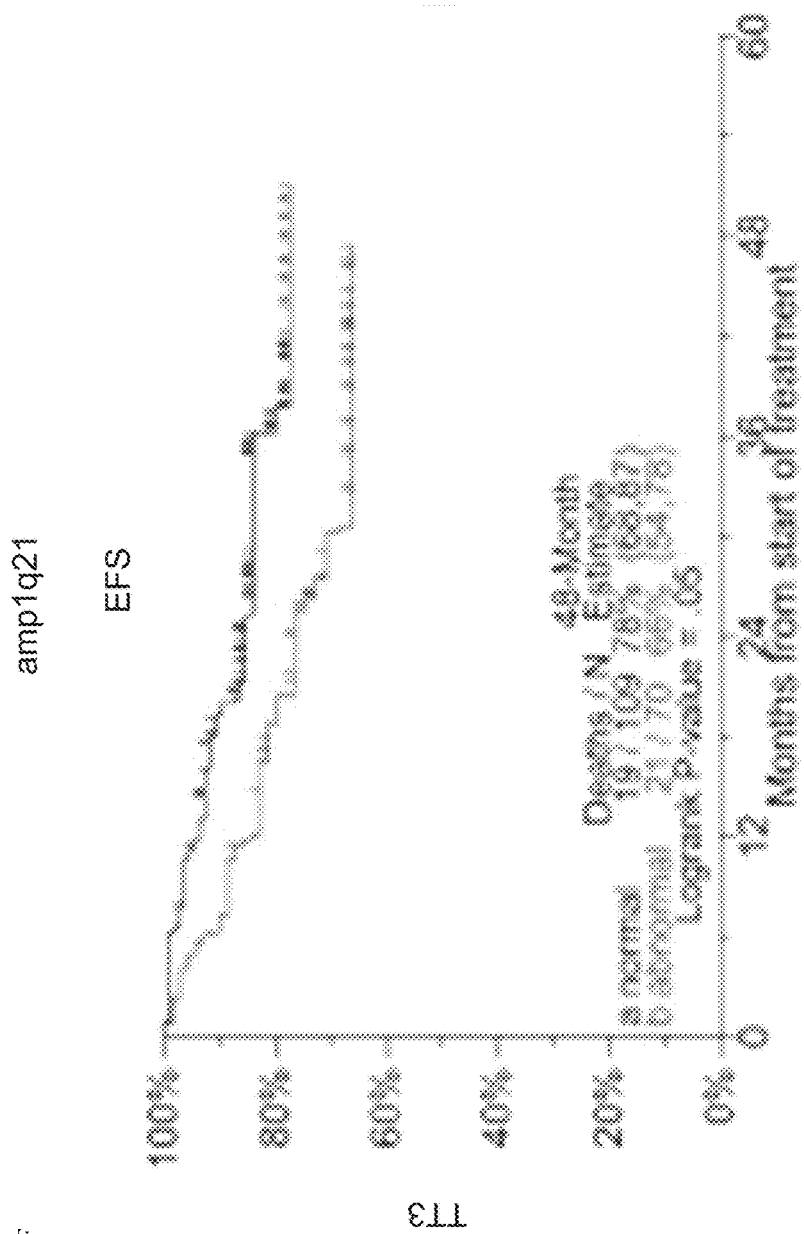
Figure 24A:
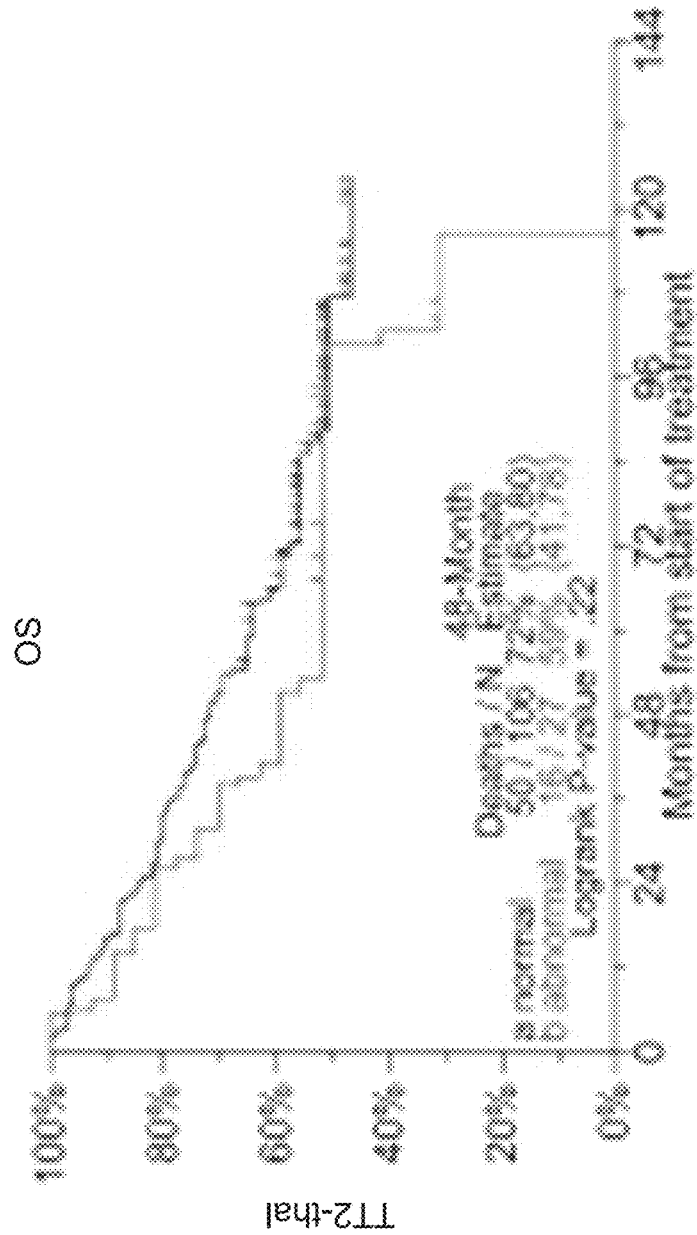
FIG. 24A-F show the Kaplan-Meier analysis of survival outcomes of 1p13 (AHCYL1) abnormalities based on gene copy numbers of 1 and 2 or greater.
Figure 24B:
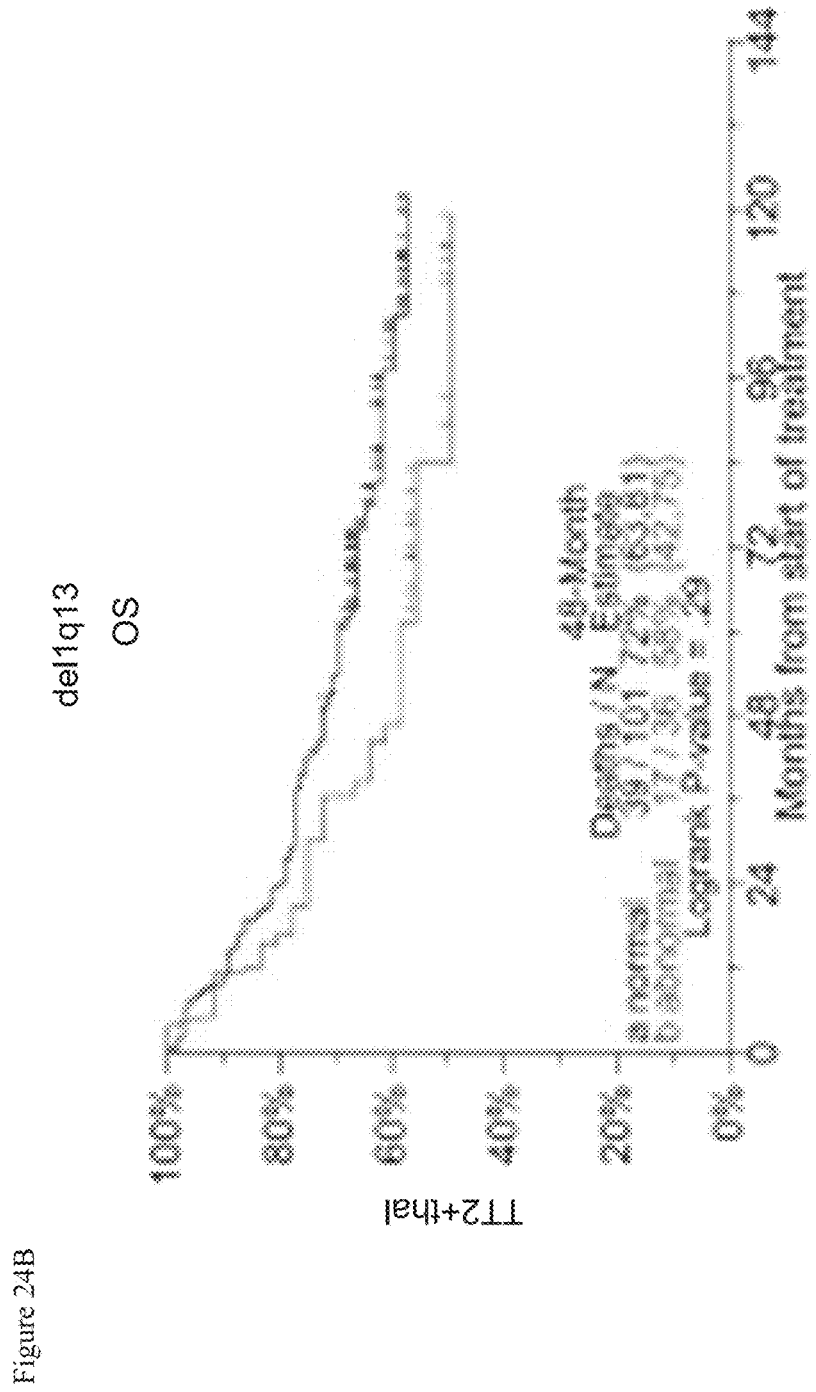
Figure 24C:
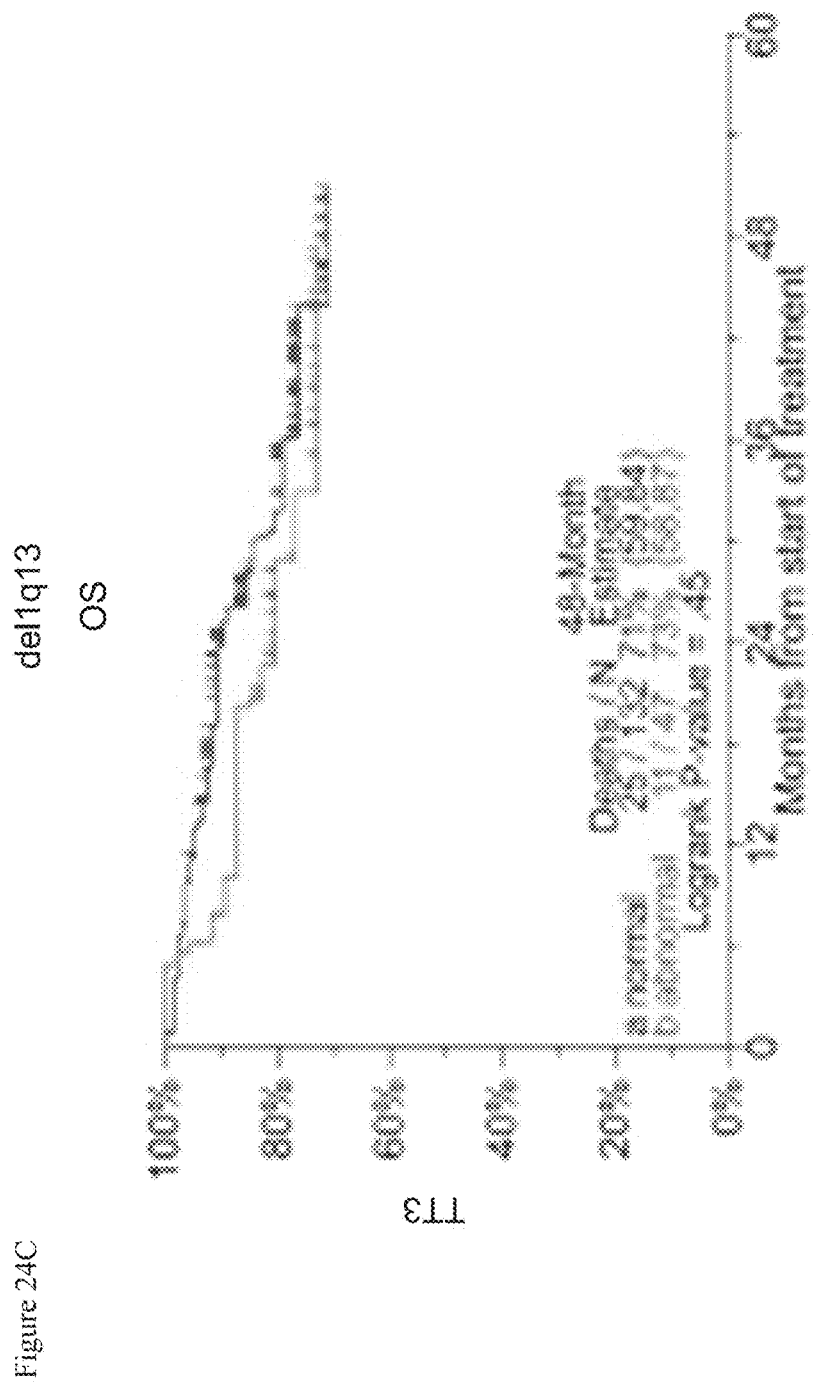
Figure 24D:
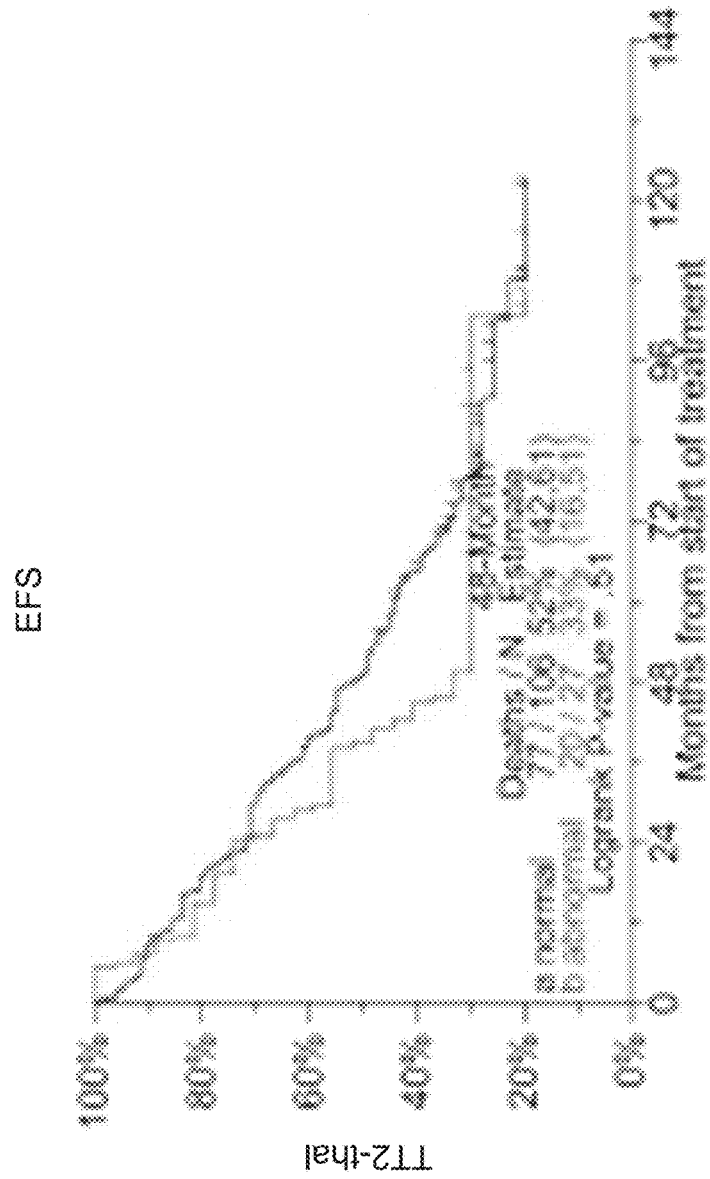
Figure 24E:
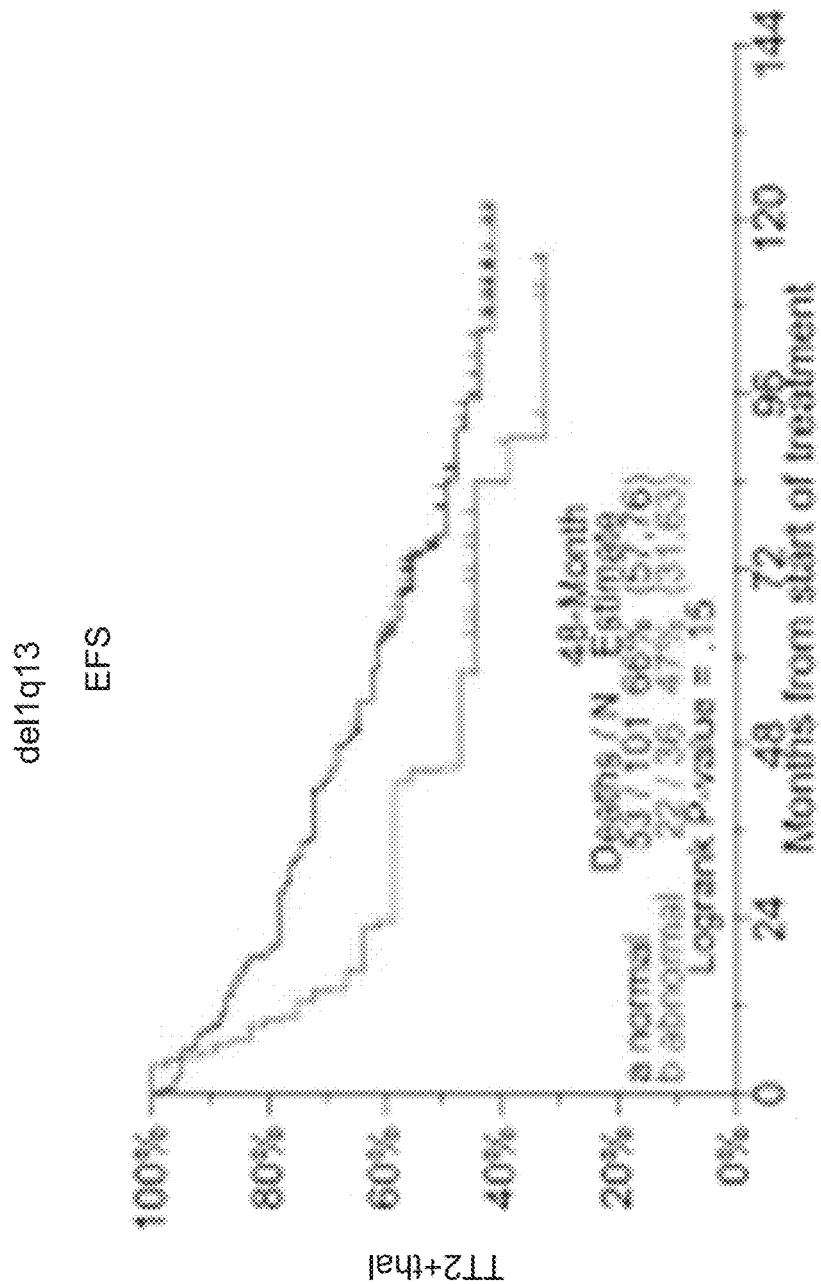
Figure 24F:
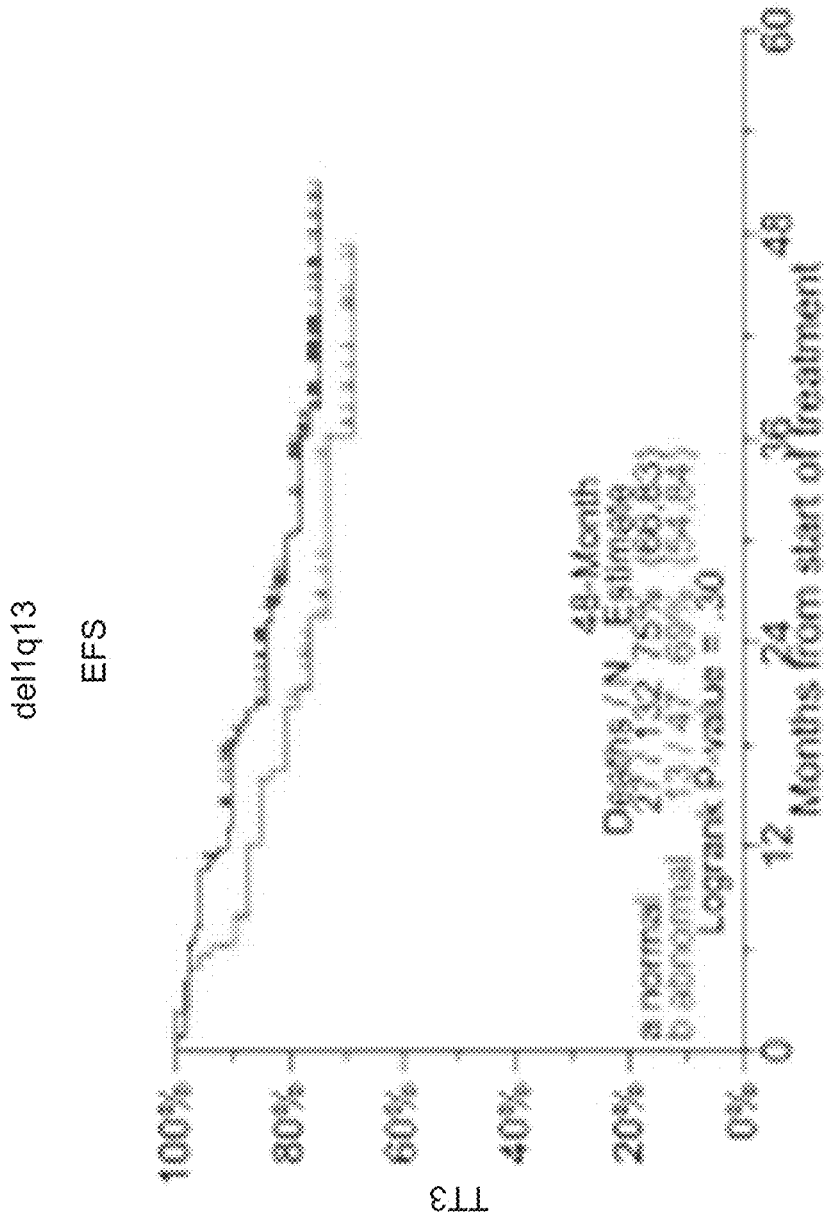
Figure 25A:
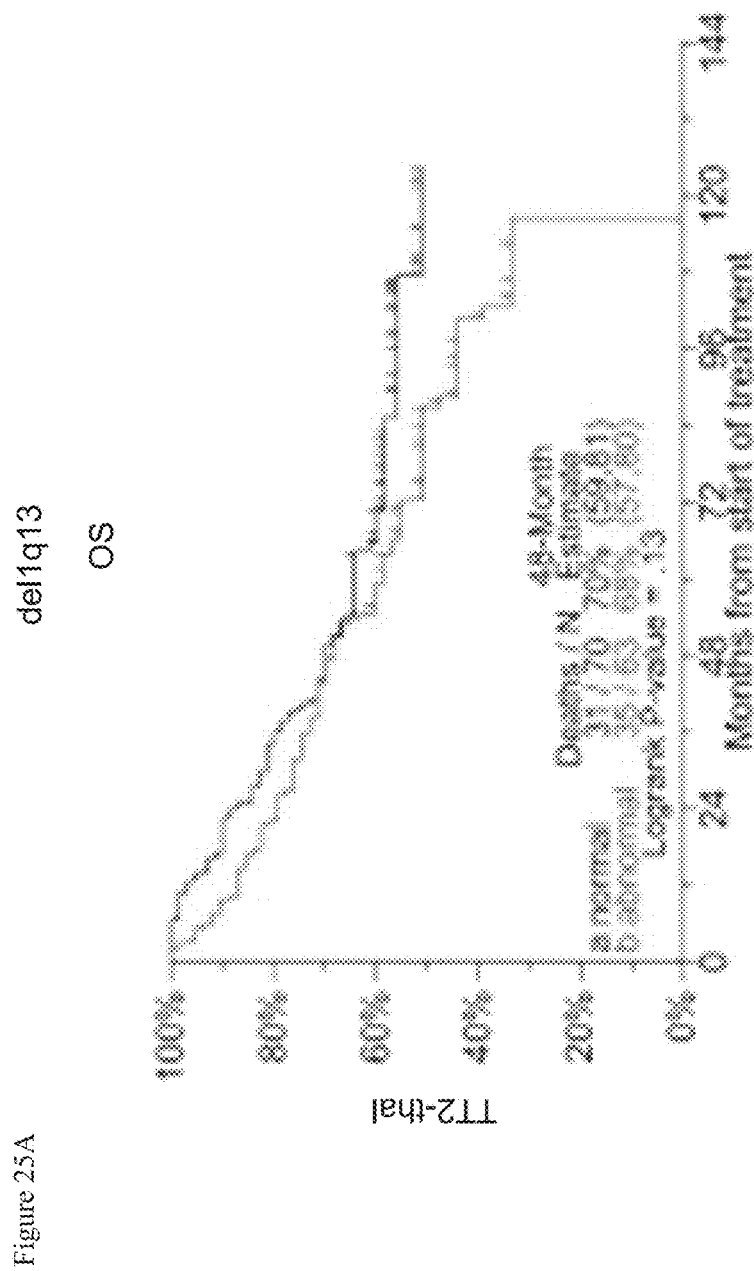
FIG. 25A-F show the Kaplan-Meier analysis of survival outcomes of 13q14 (D13S31) abnormalities based on gene copy numbers of 1 and 2 or greater.
Figure 25B:
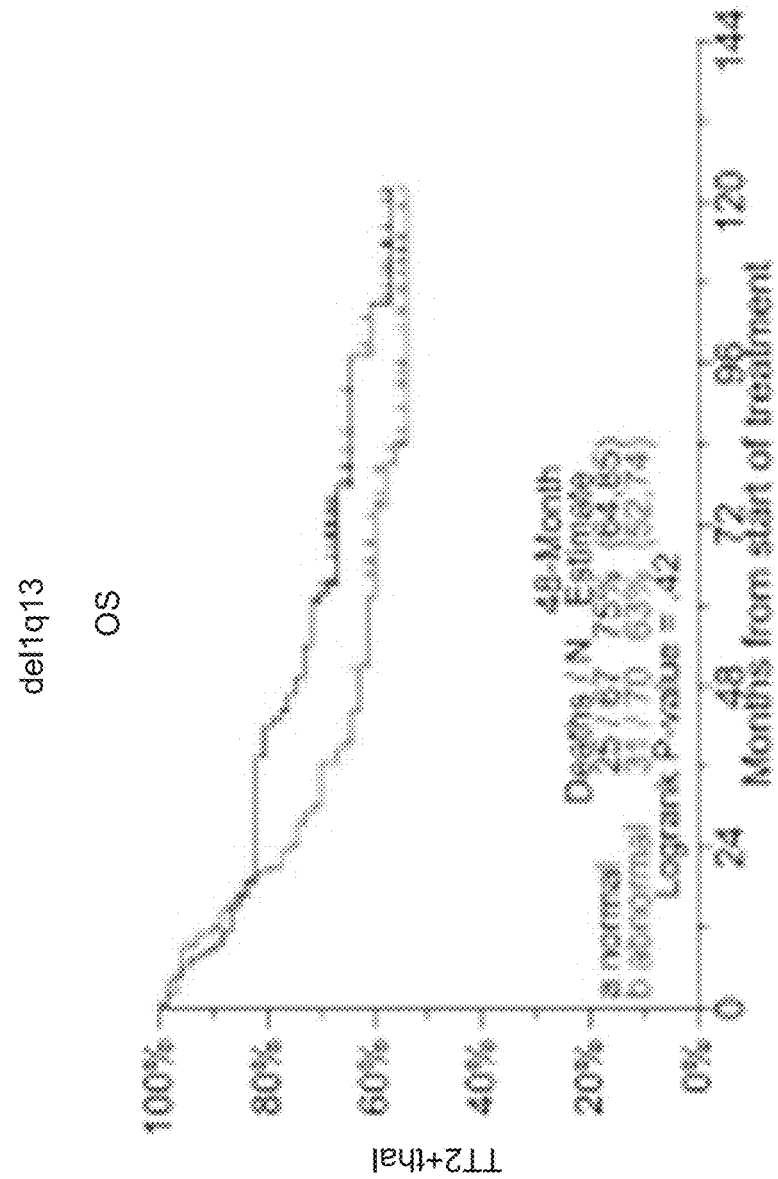
Figure 25C:
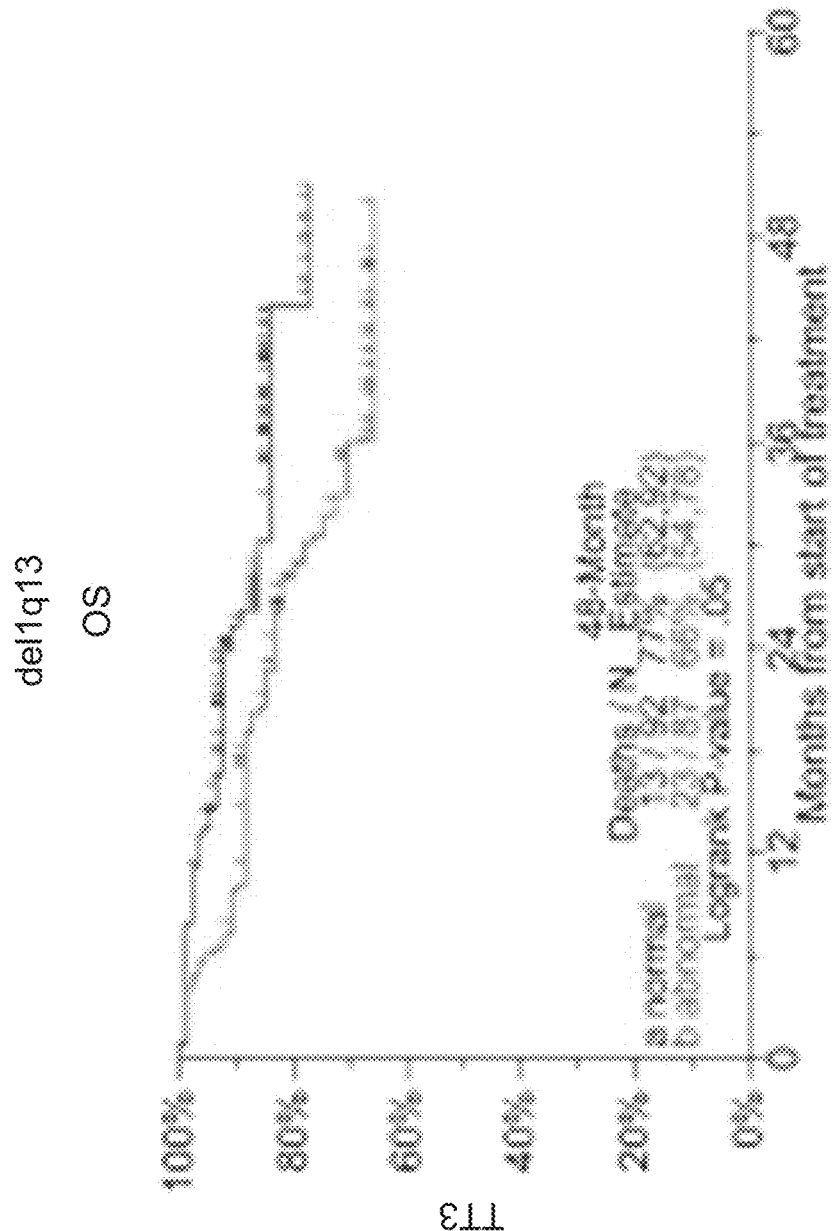
Figure 25D:
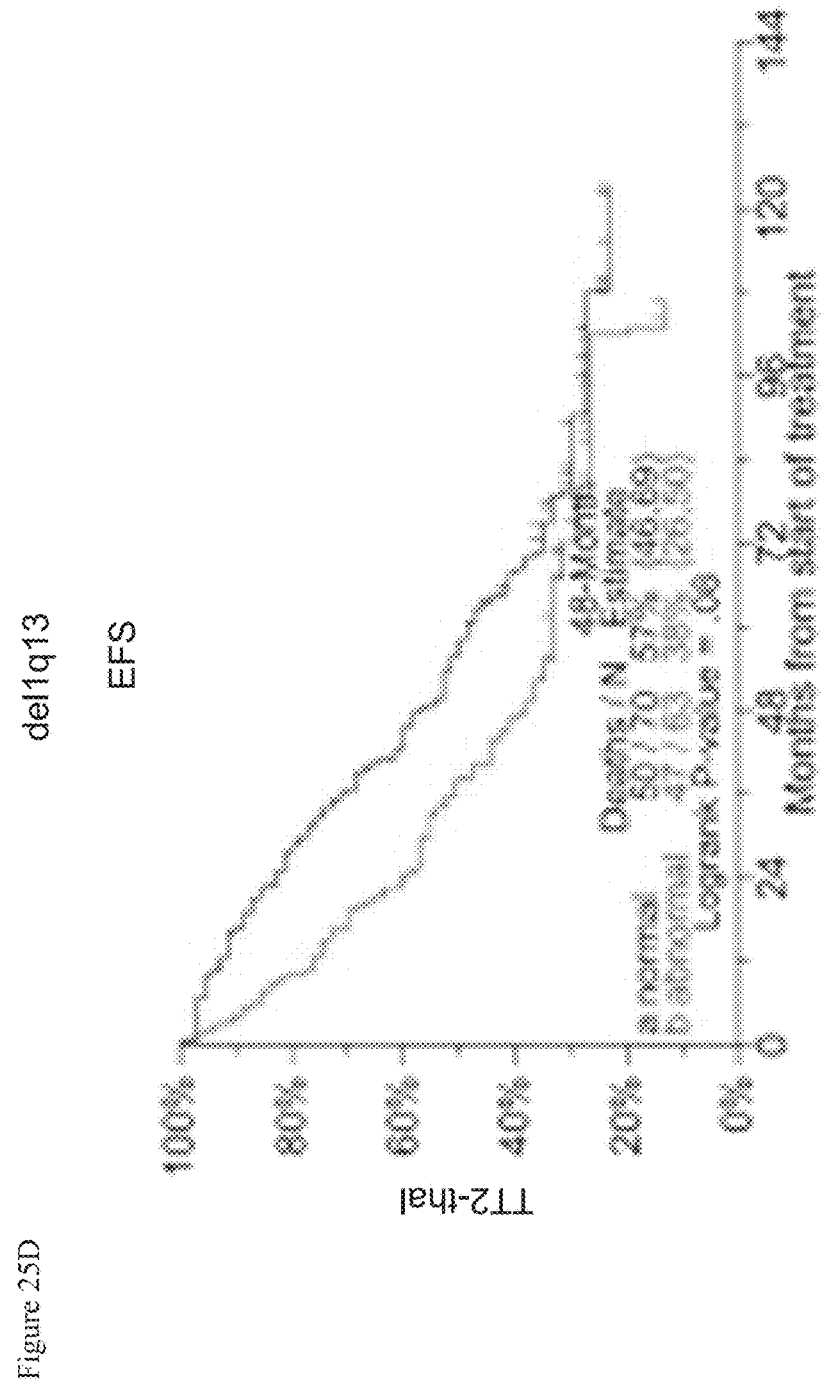
Figure 25E:
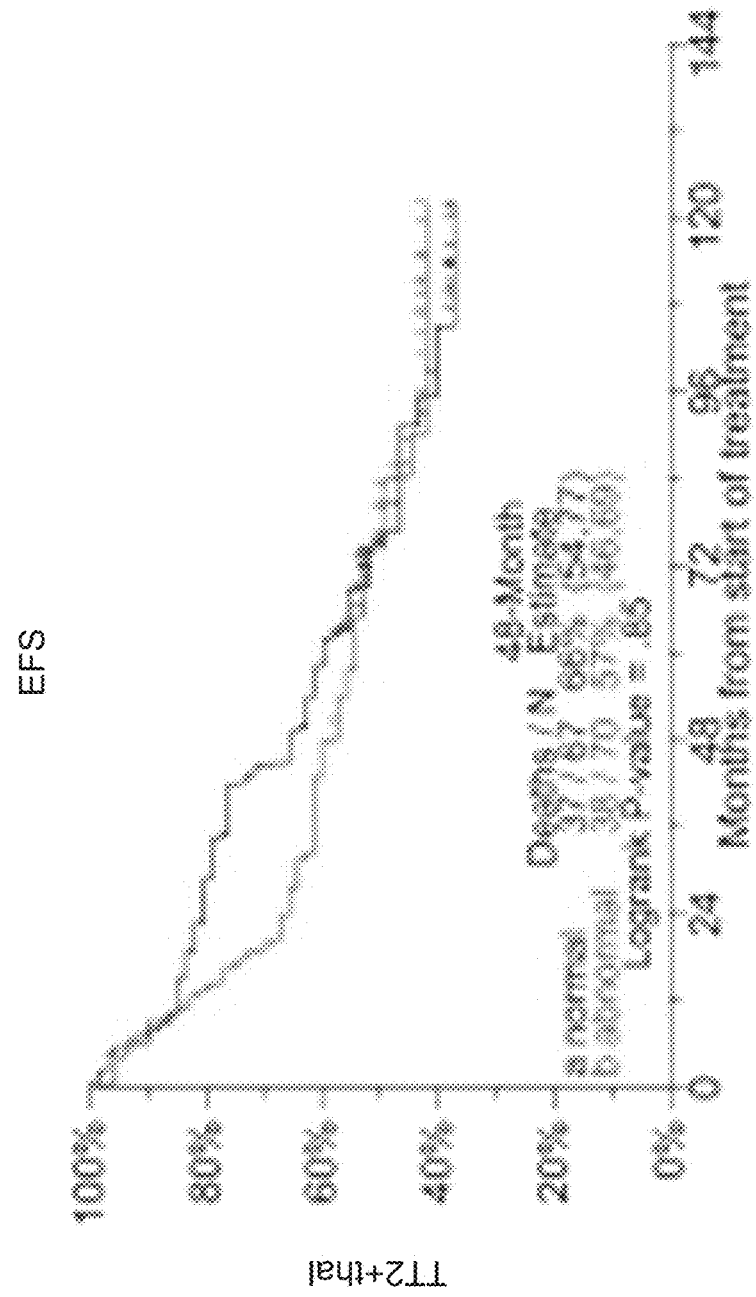
Figure 25F:
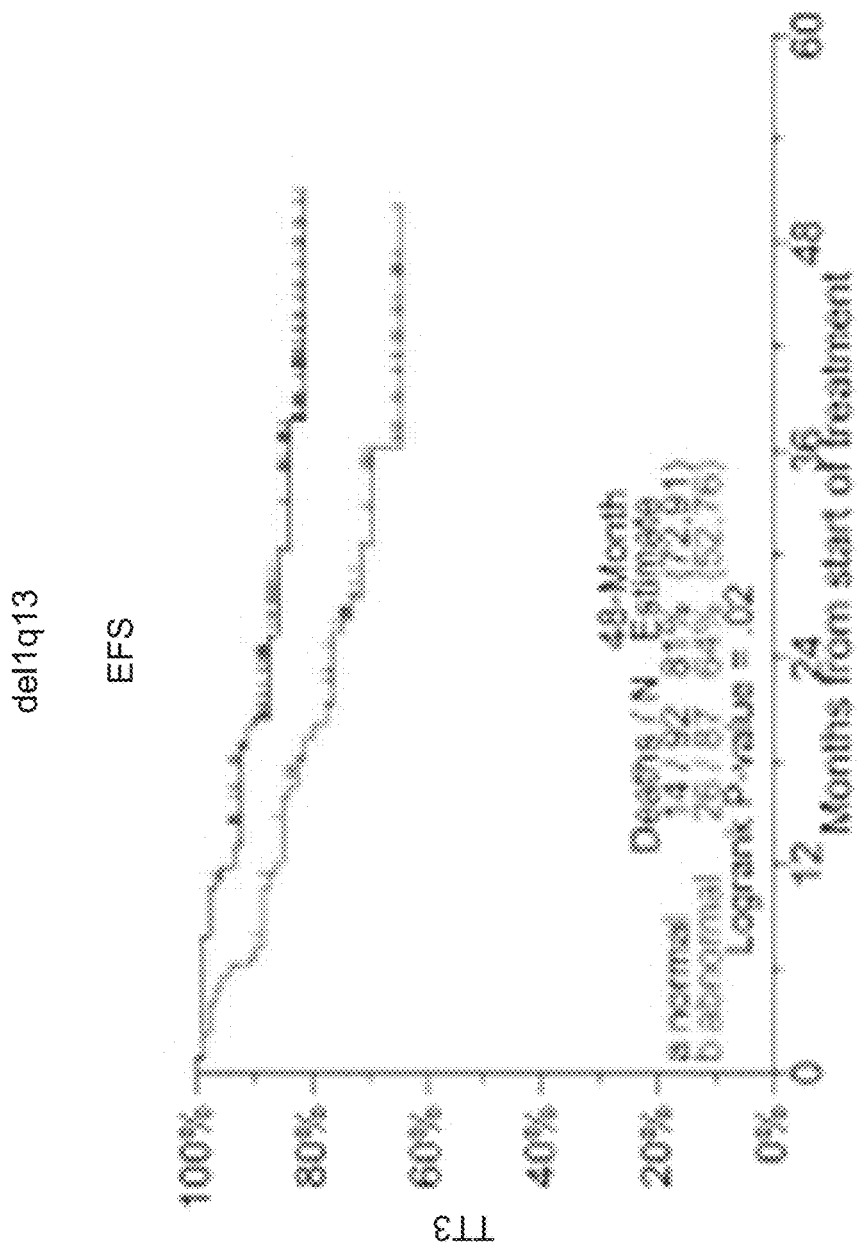
Figure 26A:
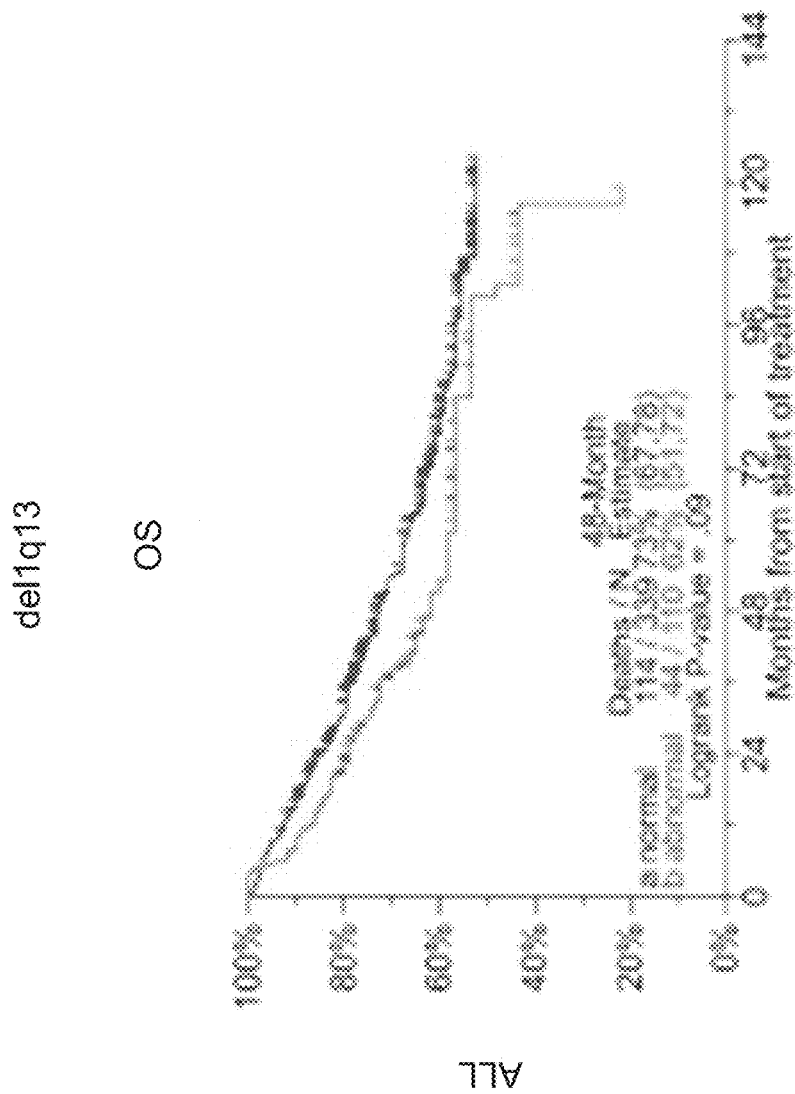
FIG. 26A-B show the Kaplan-Meier analysis of survival outcomes of 1p13 (AHCYL1) abnormalities based on gene copy numbers of 1 and 2 or greater.
Figure 26B:
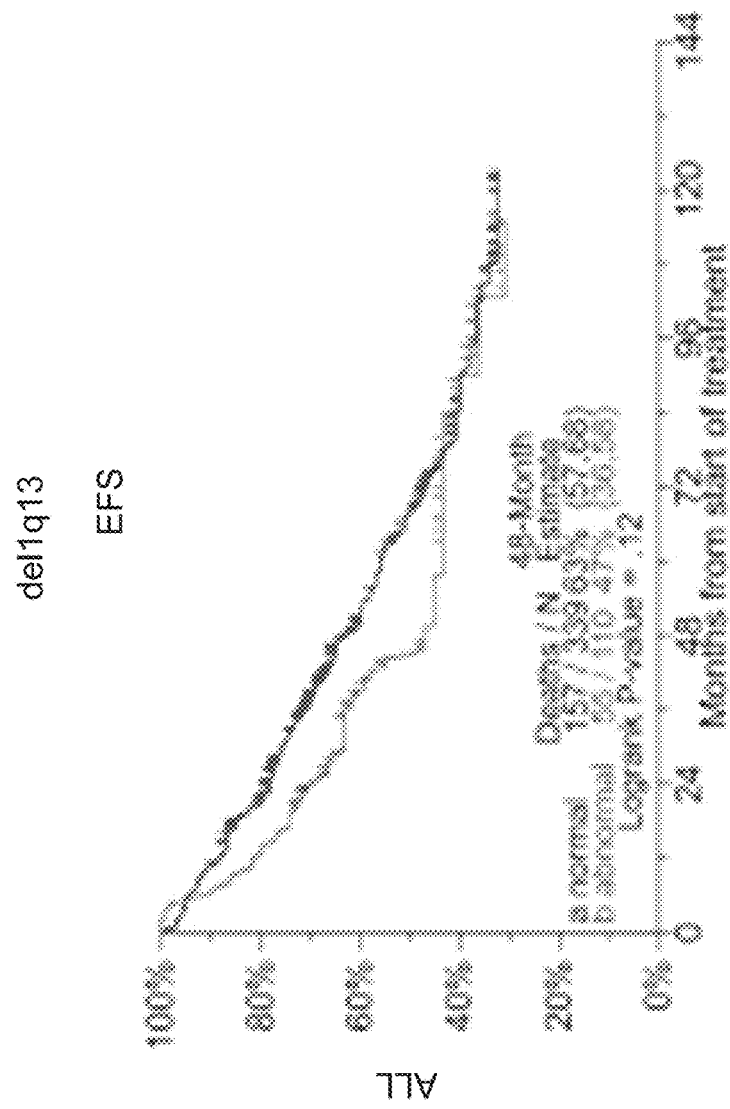
Figure 27A:
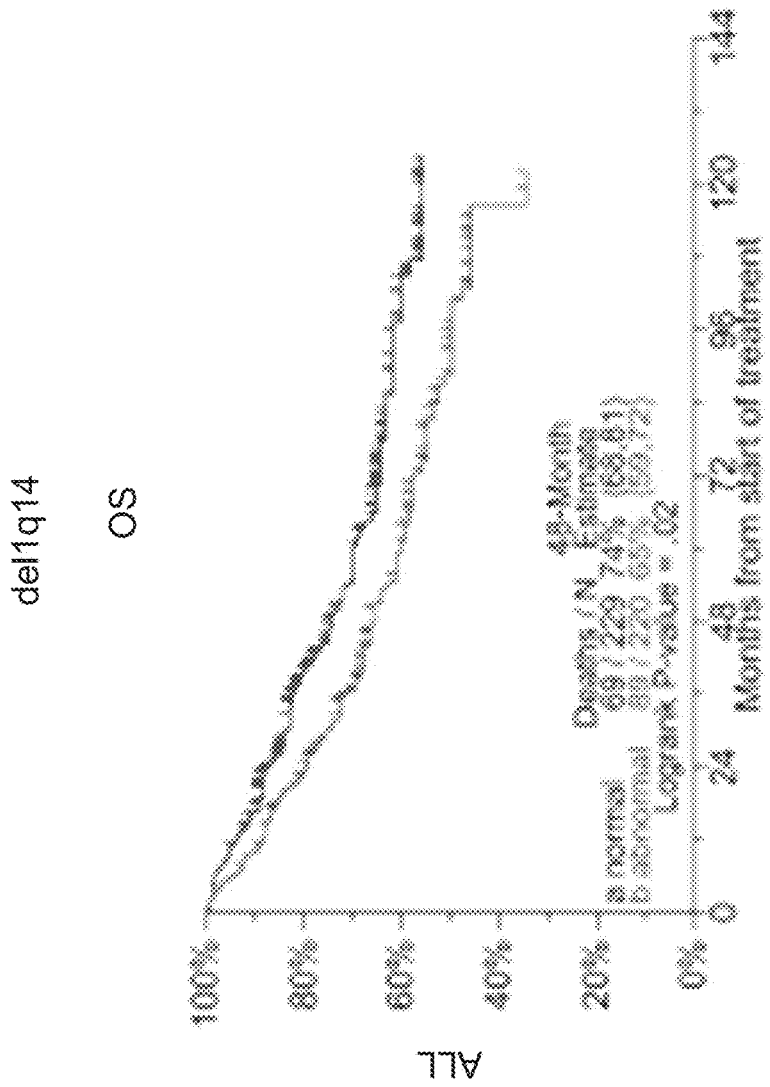
FIG. 27A-B show the Kaplan-Meier analysis of survival outcomes of 13q14 (D13S31) abnormalities based on gene copy numbers of 1 and 2 or greater.
Figure 27B:
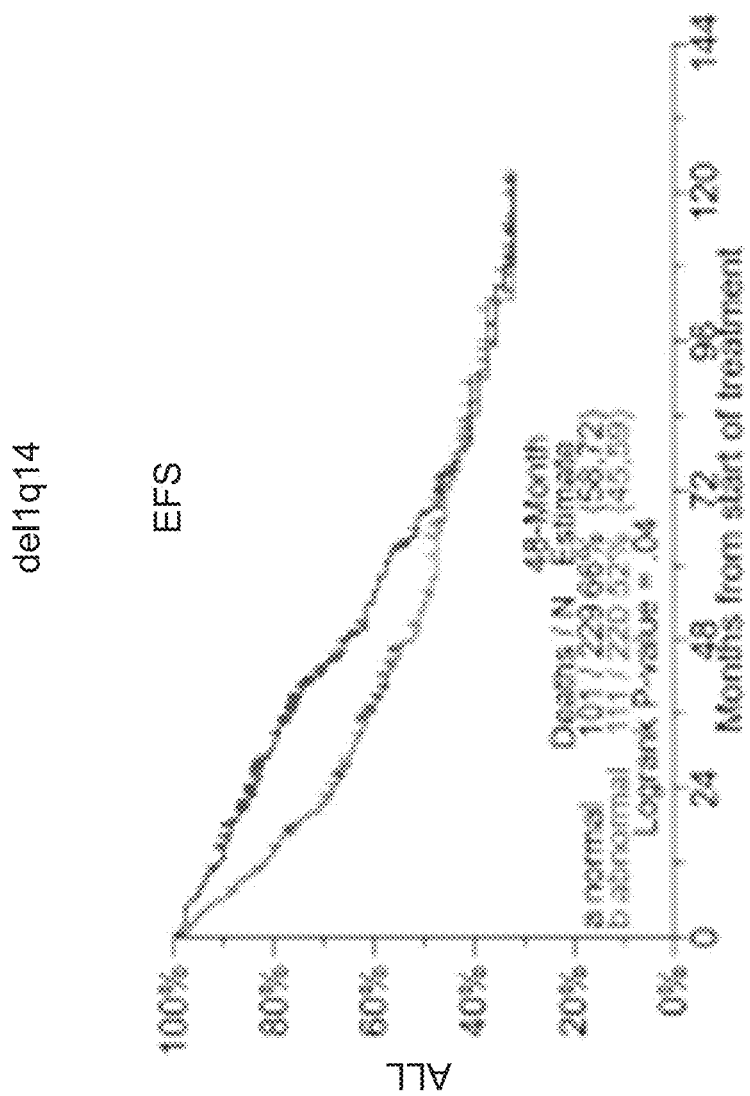
Figure 28A:
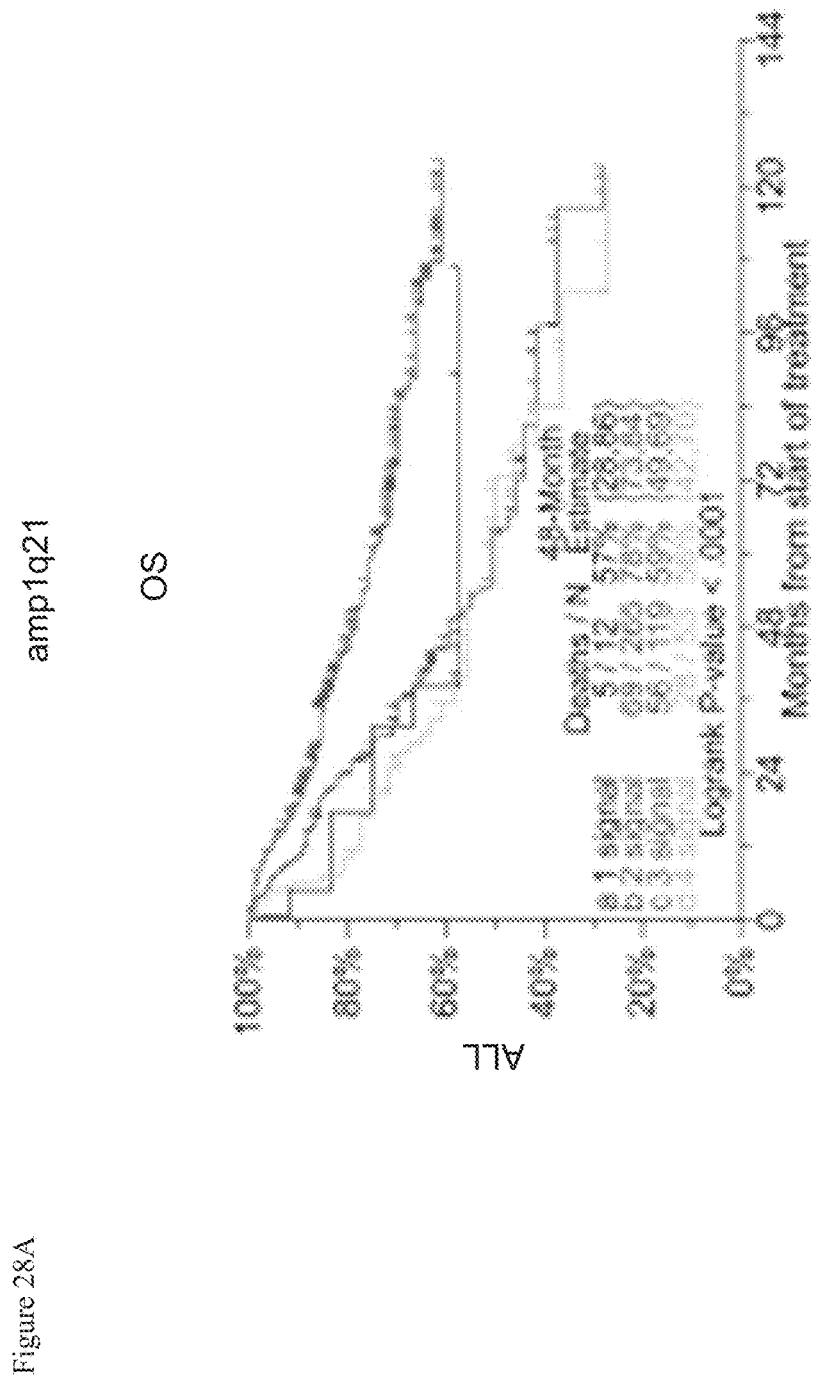
FIG. 28A-B show the Kaplan-Meier analysis of survival outcomes of 1q21 (CKS1b) abnormalities based on gene copy numbers of 1, 2, 3, or 4.
Figure 28B:
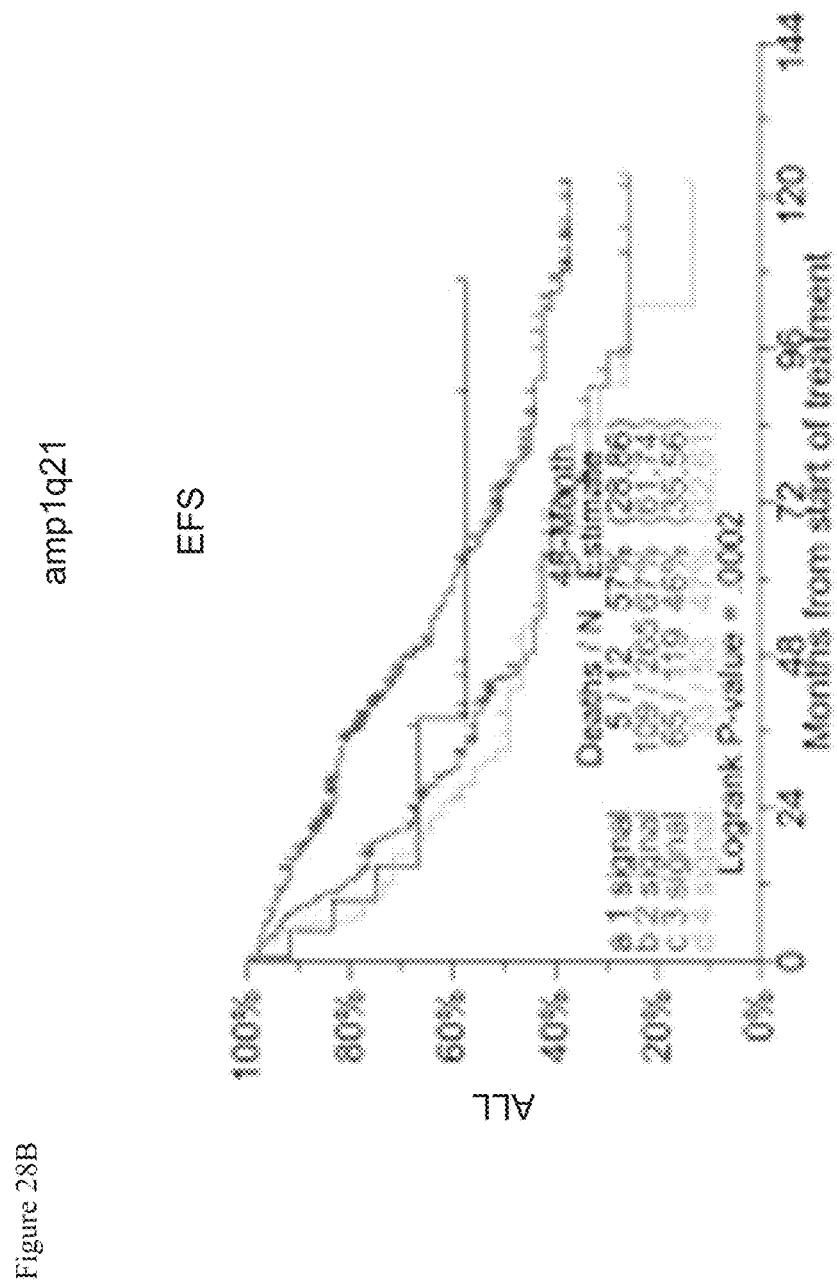
Figure 29A:
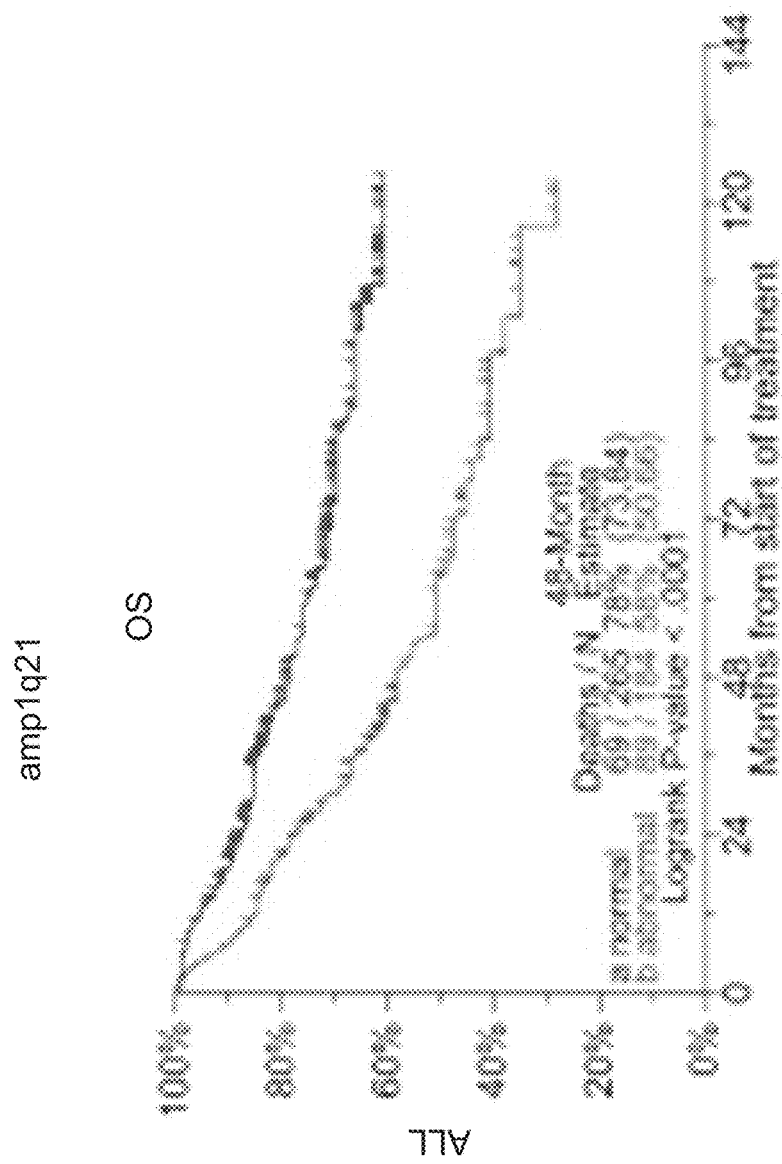
FIG. 29A-B show the Kaplan-Meier analysis of survival outcomes of 1q21 (CKS1b) abnormalities based on gene copy numbers of 2 and 1, 3 or greater.
Figure 29B:
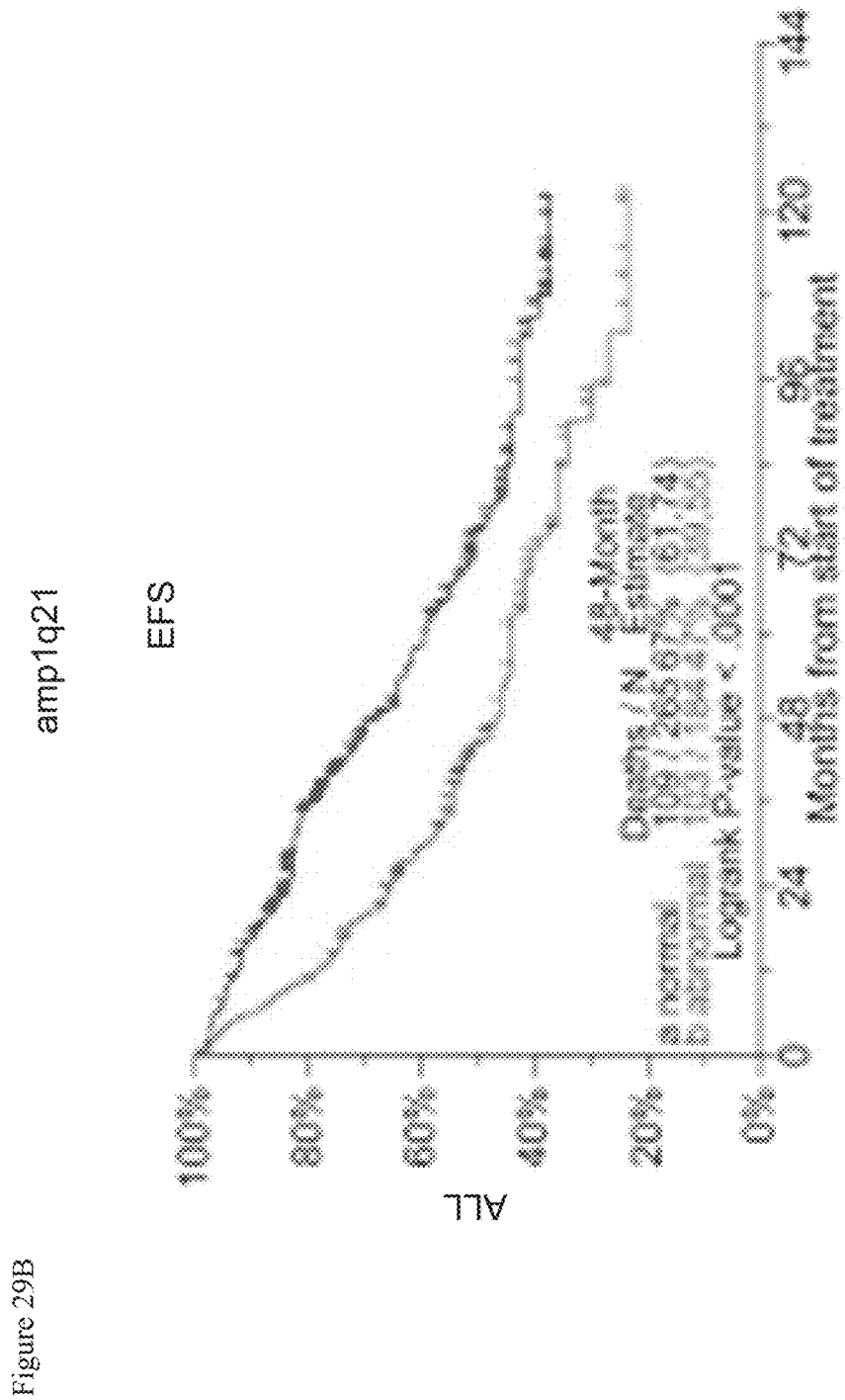

Three, four, or greater copies of 1q21 were seen 188 of 517 (37%) tested. Greater than 4 copies of 1q21, present in 62 of 517 (12%) cases, but not three copies of 1q21, was a significant adverse feature for OS in all cases combined (P=0.0009) and in TT3 (P=0.001). While there was a trend for cases with 3 or 4 copies of 1q21 to have an inferior OS than cases lacking this abnormality in TT2-thalidomide (P=0.19) (FIG. 12C) this trend was not evident in TT2+ thalidomide (P=0.89) (FIG. 12D). The lack of a difference in OS in the TT2 samples may be due to small sample size. Event-free survival is adversely affected in all cases combined, TT3 and TT2-thalidomide, but not in the TT2+ thalidomide arm. Event free survival results were comparable, with disease with greater than 4 copies of 1q21 exhibiting inferior survival when considering all cases, in TT3/TT3b (P=0.005) and TT2-thalidomide (P<0.0001), but not TT2+thalidomide (P=0.91) (FIG. 13A-D). Deletion of 1p13, present in 107 of 517 (21%) cases tested, was significant poor risk factor when considering OS (FIG. 14A-D) and EFS (FIG. 15A-D). Deletion of 1p13 was not adverse factor for OS and EFS in TT3. Remarkably, the presence of deletion of 1p13 was associated with a 3-year OS of 40% versus 80% in those lacking deletion treated with TT2+ thalidomide (P=0.01). The adverse prognostic impact of 1p13 loss on in the TT2+thalidomide arm was not evident in the TT2-thalidomide arm (P=0.52). The EFS associations were more pronounced. This was evident in of all cases (P=0.03). Although not significant, there is a clear trend for a negative impact of loss of 1p13 in TT3 (P=0.08). The negative impact of 1p13 deletion on EFS in the thalidomide arm was dramatic with median EFS of 12 months compared to 65 months for those not having 1p13 loss (P=0.04). Remarkably, the impact of 1p13 loss on outcome in the TT2-thalidomide arm was not evident, with median EFS for those with loss of 1p13 at 30 months versus 40 months for those without loss of 1p13 (P=0.69). Taken together, these data suggests that myeloma lacking 1p13 deletion benefits from the addition of thalidomide while the addition of thalidomide may have a negative impact on survival in those with disease harboring a loss of 1p13, and that bortezomib can partially overcome this negative interaction. Chromosome 13q14 deletion was found in 2457 of 517 (48%) of cases. A somewhat surprising finding was the clear lack of prognostic significance of chromosome 13q14 deletion in any of the analyses performed for OS or EFS in all trials (FIGS. 16A-D and 17A-D).

Prognostic and Predictive Implications of Combinations of Genetic Lesions

Figure 9A:
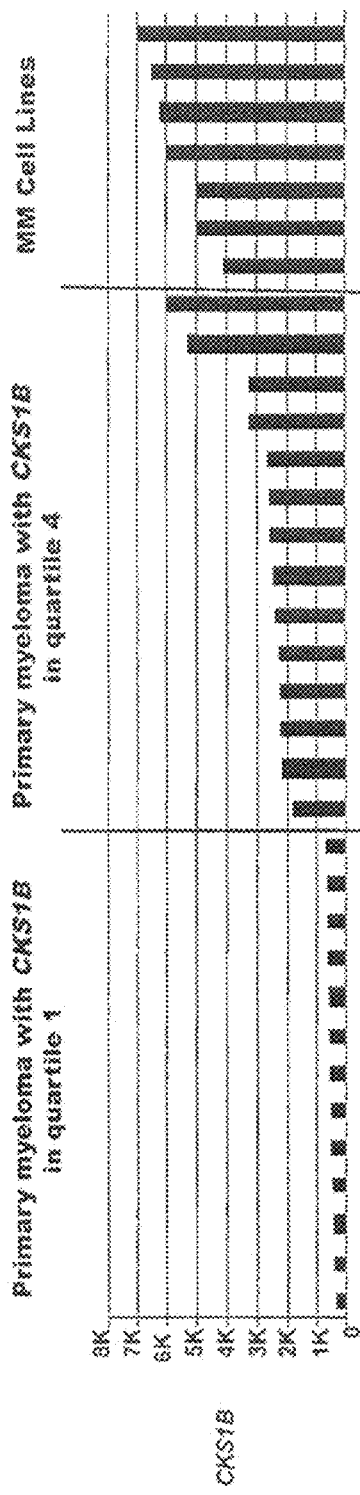
Figure 9B:
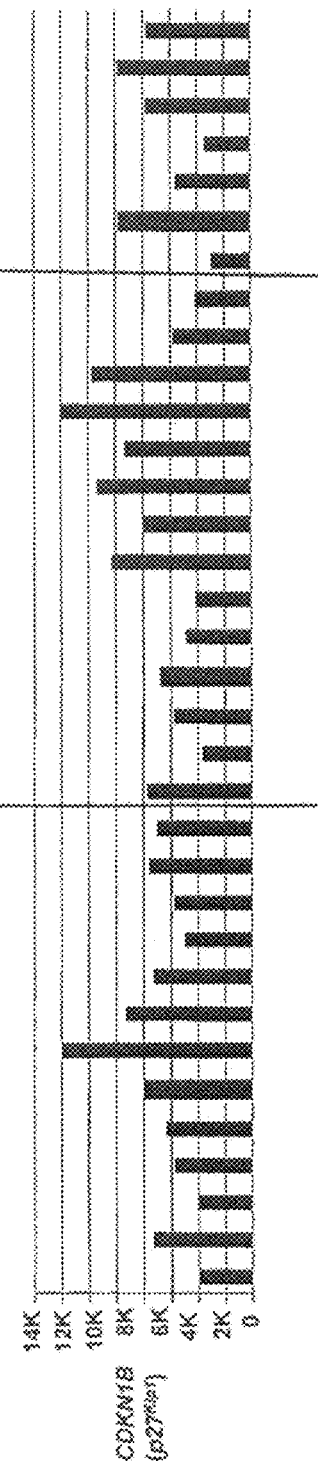

With strong evidence that the 70-gene high risk GEP signature, seen in approximately 14% of newly diagnosed disease, is driven by copy number-dependent elevated expression of genes mapping to 1q21 and reduced expression of genes mapping to chromosome 1p, disease with TRI-FISH-defined gain of 1q21 and loss of 1p13 was tested to see if there is an association with inferior survival. Disease with three or more copies of 1q21 and concomitant loss of one copy of 1p13 was seen in 38 of 517 (7%) of cases tested (FIG. 18A-D). The 3-year OS for all cases with three or more copies of 1q21 and 1 copy of 1p13 was approximately 40% compared to 80% in those with no more than one of these abnormalities (P<0.0001) (FIG. 18A-D). Present in 13 of 234 (5%) cases treated with TT3, this constellation was associated with a 3-year OS of 55% versus 83% in those with at most one of these abnormalities (P=0.005) (FIG. 18A-D). Of 61 patients treated on the TT2+thalidomide arm these two abnormalities were concurrent in 6 (10%). The 3-year OS for this group was 20% relative to 83% for cases have at most one of these abnormalities (P=0.0002) (FIG. 9). The number of cases in the TT2-thalidmide arm was too small to provide definitive results at this time. The 3-year EFS for all cases with three or more copies of 1q21 and 1 copy of 1p13 was 30% versus 70% for those with at most one abnormality (P<0.0001) (FIG. 19A-D). This value was 55% versus 80% in TT3 (P=0.03), 0% versus 60% in TT2-thalidomide (P=0.06) and 20% versus 70% in TT2-thalidomide (P=0.04). Taken together these data suggest that current therapies are not providing significant improvement in outcome for patients with disease harboring gains of 1q21 and loss of 1p13.

When considering all cases, 3 or 4 signals for 1q21 and 1 signal for 13q14 were observed in 124 of 517 (24%) tumors. This constellation of was associated with shorter EFS times than those with no abnormalities in these two chromosomes or abnormalities in only one chromosome (P=0.0003) (FIG. 20A-D). Present in 55 of 247 (22%) this genetic combination was not associated with an inferior EFS (P=0.13) in TT3 samples. Moreover, this combination was not an adverse prognostic factor in TT2+thalidomide (P=0.74), but represented a powerful poor risk feature in TT2-thalidomide (P<0.0001), with the 25% of cases with tumors having both abnormalities experiencing a median EFS of 24 months versus 48 months for those with one or none of these two genetic lesions. Although similar trends were observed for OS, the presence of both lesions was only significant when considering all cases (P=0.004) (FIG. 21A-D). There was a borderline significance for the TT2-thalidomide group (P=0.06), which may emerge as significant as more samples are tested.

Thus, in summary, fluorescence in situ hybridization (FISH) analysis for 1q21 amplification and deletion 13 represents a better method for risk assessment than any other that exists. Additionally, since FISH demonstrated that the strong correlation of expression of CKS1B with gene copy number and also that the risk of death increased with increase in gene copy number, FISH could be used to detect residual disease and predict recurrence and progression. Since Western blot analysis demonstrated that an increase in the levels of CKS1B protein, CKS1B or any pathway in which it works could be therapeutically targeted. Thus, the amplification of 1q21 could be a diagnostic, prognostic and potential target in cancer especially myeloma.

The following references are cited herein:
Attal M. et al. *N Engl J Med* 2003; 349:2495-502.
Barlogie B. et al. *Williams Hematology* 2001; 1279-1304.
Barlogie B. et al. *Blood* 2004; 103:20-32.
Bullinger L. et al. *N Engl J Med* 2004; 350:1605-16.
Fonseca R. et al. *Cancer Res* 2004; 64:1546-58.
Ganoth D. et al. *Nat Cell Biol.* 2001 3:321-4.
Gutierrez N. C. et al. *Blood.* 2004; 104:2661-6.
Hideshima T. et al. *Blood* 2004; 104:607-18.
Kuehl W. M. and Bergsagel P. L. *Nature Rev Cancer* 2002; 2:175-187.
Le Baccon P. *Genes Chromosomes Cancer.* 2001; 32:250-64.
McCoy J. et al. *Blood* 2003; 102; 2512a.
Morris M. C. et al. *Nature.* 2003; 423(6943):1009-13.
Nakayama K. et al. *Dev Cell.* 2004; 6:661-72.
Nilsson T. et al. *Br J Haematol.* 2003; 120:960-9.
O'Quigley J and Xu R. Explained variation in proportional hazards regression. In: Crowley J, ed. *Handbook of Statistics in Clinical Oncology.* New York, N.Y.: Marcel Dekker, 2001:397-410.
Pagano M. *Mol Cell.* 2004; 14:414-6.
Pagano M. and Benmaamar R. *Cancer Cell.* 2003; 4:251-6.
Peters J. M. *Mol Cell.* 2002; 95:931-43.
R Development Core Team. R: A language and environment for statistical computing. R Foundation for Statistical Computing, Vienna, Austria. 2004. ISBN 3-900051-07-0, www.R-project.org.
Rosenwald A. et al. *N Engl J Med* 2002; 346:1937-47.
Sawyer J. R. et al. *Genes Chromosomes Cancer* 2005; 42:95-106.
Sawyer J. R. et al. *Blood.* 91:1732-41, 1998.
Shaughnessy J. and Barlogie B. *Immunol Rev* 2003; 94:140-63.
Shaughnessy J. et al. *Blood* 2003; 101:3849-3856.
Shaughnessy J Jr. et al. *Br J Haematol.* 2003; 120:44-52.
Shaughnessy J. et al. *Blood* 2000; 96:1505-11.
Sherr C. J. and Roberts J. M. *Genes Dev.* 1999; 13:1501-12.
Shipp M. A. et al. *Nat Med* 2002; 8:68-74.
Slingerland J. and Pagano M. *J Cell Physiol* 2000; 183:10-17.
Spruck C. et al. *Mol Cell.* 2001; 7:639-50.
Storey and Tibshirani *Proc Natl Acad Sci.* 2003; 100(16): 9440-9445.
Tarte K. et al. *Blood* 2003; 102:592-600.
Tian E. et al. *N Eng J Med* 2003; 349:2483-94.
Valk P. J. et al. *N Engl J Med* 2004; 350:1617-28.
Yeoh E. J. et al. *Cancer Cell* 2002; 1:133-143.
Zhan, F. et al. *Blood* 2002; 99:1745-57.
Zhan F. et al. *Blood* 2003; 101:1128-1140.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A method of detecting high risk multiple myeloma in a human subject diagnosed with monoclonal gammopathy of undetermined significance (MGUS), comprising the steps of:
   determining gene expression levels of GNG10, PNPLA4, KIAA1754, AHCYL1, MCLC, EVI5, AD-020, PARG1, CTBS, FUCA1, RFP2, FLJ20489, LTBP1, TRIP13, AIM2, SELI, SLC19A1, LARS2, OPN3, ASPM, CCT2, UBE21, STK6, FLJ13052, FLJ12525, BIRC5, CKS1B, CKAPl, MGC57827, DKFZp7790175, PFN1, ILF3, IFI16, TBRG4, PAPDl, EIF2C2, MGC4308, ENOl, DSG2, EXOSC4, TAGLN2, RUVBL1, ALDOA, CPSF3, MGC15606, LGALS1, RAD18, SNX5, PSMD4, RAN, KIF14, CBX3, TMPO, DKFZP586L0724, WEEl, ROBO1, TCOF1, YWHAZ, and MPHOSPH1 in plasma cells isolated from the human patient, wherein the gene expression levels are determined by isolating RNA from the plasma cells and contacting the isolated RNA or a cDNA derived therefrom with a nucleic acid probe specific for each gene; and
   comparing the expression levels to expression levels for each gene in a control sample from a normal healthy individual and detecting high risk multiple myeloma on the basis of the comparison, wherein:
   reduced expression of GNG10, PNPLA4, KIAA1754, AHCYL1, MCLC, EVI5, AD-020, PARG1, CTBS, FUCA1, RFP2, FLJ20489, or LTBP1, relative to the control is associated with high risk multiple myeloma; and
   overexpression of TRIP13, AIM2, SELI, SLC19A1, LARS2, OPN3, ASPM, CCT2, UBE21, STK6, FLJ13052, FLJ12525, BIRC5, CKS1B, CKAPl, MGC57827, DKFZp7790175, PFN1, ILF3, IFI16, TBRG4, PAPDl, EIF2C2, MGC4308, ENOl, DSG2, EXOSC4, TAGLN2, RUVBL1, ALDOA, CPSF3, MGC15606, LGALS1, RAD18, SNX5, PSMD4, RAN, KIF14, CBX3, TMPO, DKFZP586L0724, WEEl, ROBO1, TCOF1, YWHAZ, or MPHOSPH1, relative to the control is associated with high risk multiple myeloma.

2. The method of claim 1, wherein the gene expression levels are determined by DNA microarray or RT-PCR.

3. The method of claim 1, wherein determining the gene expression levels comprises generating cDNA from the isolated RNA.

4. The method of claim 1, wherein the plasma cells are CD138-enriched plasma cells.

* * * * *